United States Patent
Drew et al.

(10) Patent No.: US 10,206,960 B2
(45) Date of Patent: *Feb. 19, 2019

(54) STABILISATION OF VIRAL PARTICLES

(75) Inventors: Jeffrey Drew, London (GB); David Woodward, London (GB); John Bainbridge, London (GB); Amanda Corteyn, London (GB)

(73) Assignee: Stabilitech Biopharma Ltd, West Sussex (GB)

(*) Notice: Subject to any disclaimer, the term of this patent is extended or adjusted under 35 U.S.C. 154(b) by 532 days.

This patent is subject to a terminal disclaimer.

(21) Appl. No.: 13/637,817

(22) PCT Filed: Mar. 31, 2011

(86) PCT No.: PCT/GB2011/000498
§ 371 (c)(1),
(2), (4) Date: Feb. 11, 2013

(87) PCT Pub. No.: WO2011/121306
PCT Pub. Date: Oct. 6, 2011

(65) Prior Publication Data
US 2013/0129685 A1 May 23, 2013

(30) Foreign Application Priority Data
Mar. 31, 2010 (EP) .................... 10250706
Mar. 31, 2010 (GB) .................... 1005497.1
(Continued)

(51) Int. Cl.
*C12N 7/00* (2006.01)
*A61K 35/76* (2015.01)
(Continued)

(52) U.S. Cl.
CPC ............ *A61K 35/76* (2013.01); *C12N 7/00* (2013.01); *A61K 9/19* (2013.01); *A61K 39/00* (2013.01);
(Continued)

(58) Field of Classification Search
None
See application file for complete search history.

(56) References Cited

U.S. PATENT DOCUMENTS 3,927,208 A  12/1975  Zygraich et al.
4,631,189 A  12/1986  Kendall et al.
(Continued)

FOREIGN PATENT DOCUMENTS

CA      2083407 A1    5/1993
CN    101670104 A     3/2010
(Continued)

OTHER PUBLICATIONS

Vasdevamurthy et al., "Enzyme stabilization using synthetic compensatory solutes," Biocatalysis and Biotransformation, 23(3/4): 285-291 (2005)).*
(Continued)

*Primary Examiner* — Michelle S Horning
(74) *Attorney, Agent, or Firm* — Clark & Elbing LLP; Susan M. Michaud

(57) ABSTRACT

A method for preserving viral particles comprising: (a) providing an aqueous solution of (i) viral particles, (ii) optionally one or more sugars, and (iii) a compound of formula (I) or a physiologically acceptable salt or ester thereof and/or a compound of formula (II) or a physiologically acceptable salt or ester thereof; and (b) drying the solution to form a composition incorporating said viral particles.

13 Claims, 36 Drawing Sheets

(30) Foreign Application Priority Data

| | | | |
|---|---|---|---|
| Mar. 31, 2010 | (GB) | ................................ | 1005520.0 |
| Mar. 31, 2010 | (GB) | ................................ | 1005521.8 |
| Sep. 8, 2010 | (GB) | ................................ | 1014962.3 |
| Oct. 19, 2010 | (GB) | ................................ | 1017647.7 |
| Oct. 19, 2010 | (GB) | ................................ | 1017648.5 |

(51) Int. Cl.
  *A61K 9/19* (2006.01)
  *A61K 47/18* (2017.01)
  *A61K 47/20* (2006.01)
  *A61K 47/26* (2006.01)
  *A61K 39/00* (2006.01)

(52) U.S. Cl.
  CPC ............ *A61K 47/183* (2013.01); *A61K 47/20* (2013.01); *A61K 47/26* (2013.01); *C12N 2710/10351* (2013.01)

(56) References Cited

U.S. PATENT DOCUMENTS

| | | | |
|---|---|---|---|
| 4,639,339 A | | 1/1987 | Murashige et al. |
| 4,808,700 A | | 2/1989 | Anderson et al. |
| 4,816,568 A | | 3/1989 | Hamilton, Jr. et al. |
| 4,950,596 A | | 8/1990 | Cheng et al. |
| 5,109,026 A | | 4/1992 | Hoskinson et al. |
| 5,169,758 A | | 12/1992 | Fischer et al. |
| 5,240,843 A | | 8/1993 | Gibson et al. |
| 5,580,856 A | | 12/1996 | Prestrelski et al. |
| 5,618,539 A | | 4/1997 | Dorval et al. |
| 5,691,163 A | | 11/1997 | Cameron et al. |
| 6,037,116 A | * | 3/2000 | Wiggins et al. ............... 435/1.1 |
| 6,127,181 A | | 10/2000 | Kadkade |
| 6,194,136 B1 | | 2/2001 | Livesey et al. |
| 6,248,588 B1 | | 6/2001 | Crespo et al. |
| 6,689,600 B1 | | 2/2004 | Wu et al. |
| 7,235,391 B2 | | 6/2007 | Wu et al. |
| 9,101,607 B2 | | 8/2015 | Drew et al. |
| 2004/0110267 A1 | | 6/2004 | Sundar |
| 2004/0253574 A1 | | 12/2004 | Schuler et al. |
| 2005/0048058 A1 | | 3/2005 | Yamazaki et al. |
| 2005/0239705 A1 | | 10/2005 | Dake et al. |
| 2006/0073182 A1 | | 4/2006 | Wong et al. |
| 2006/0154858 A1 | | 7/2006 | Mattson et al. |
| 2006/0228334 A1 | * | 10/2006 | Rosa-Calatrava et al. .. 424/93.2 |
| 2006/0247167 A1 | | 11/2006 | Schlein et al. |
| 2007/0253941 A1 | | 11/2007 | Naidu et al. |
| 2008/0107631 A1 | | 5/2008 | Wu et al. |
| 2008/0299168 A1 | * | 12/2008 | Dadey .................... A61K 9/0024 424/423 |
| 2009/0123436 A1 | | 5/2009 | Opperman |
| 2010/0029569 A1 | | 2/2010 | Bjorn et al. |
| 2010/0260796 A1 | * | 10/2010 | Belin-Poput et al. ...... 424/202.1 |
| 2011/0081363 A1 | * | 4/2011 | Whitney et al. ............ 424/184.1 |
| 2013/0071431 A1 | | 3/2013 | Drew et al. |
| 2013/0129685 A1 | | 5/2013 | Drew et al. |
| 2013/0156797 A1 | | 6/2013 | Drew et al. |
| 2013/0164296 A1 | | 6/2013 | Drew et al. |
| 2014/0294757 A1 | | 10/2014 | Drew et al. |
| 2017/0021008 A1 | | 1/2017 | Drew |

FOREIGN PATENT DOCUMENTS

| | | |
|---|---|---|
| EP | 0130619 A2 | 1/1985 |
| EP | 0156242 A2 | 10/1985 |
| EP | 0312114 A2 | 4/1989 |
| EP | 0376361 A2 | 7/1990 |
| EP | 0890362 A1 | 1/1999 |
| EP | 1946776 A1 | 7/2008 |
| EP | 1961761 A1 | 8/2008 |
| EP | 1133316 B1 | 1/2009 |
| JP | 60-193925 | 10/1985 |
| JP | 61189228 A | 8/1986 |
| JP | H2-422 A | 1/1990 |
| JP | H6-153926 A | 6/1994 |
| JP | H8-505286 A | 6/1996 |
| JP | 2003095956 A | 4/2003 |
| JP | 2003-261591 A | 9/2003 |
| JP | 2006-514538 A | 5/2006 |
| JP | 2007-524592 A | 8/2007 |
| JP | 2008-5846 A | 1/2008 |
| JP | 2008513438 A | 5/2008 |
| JP | 2009510136 A | 3/2009 |
| JP | 2009526856 A | 7/2009 |
| JP | 2011-516608 A | 5/2011 |
| WO | WO-89/11297 A1 | 11/1989 |
| WO | WO-90/05182 A1 | 5/1990 |
| WO | WO 9300807 A1 * | 1/1993 |
| WO | WO-94/04174 A1 | 3/1994 |
| WO | WO-95/10605 A1 | 4/1995 |
| WO | WO-95/11700 A1 | 5/1995 |
| WO | WO-97/04801 A1 | 2/1997 |
| WO | WO-97/15331 A1 | 5/1997 |
| WO | WO-99/27071 A1 | 6/1999 |
| WO | WO-00/29024 A1 | 5/2000 |
| WO | WO-01/29198 A1 | 4/2001 |
| WO | WO-01/93829 A2 | 12/2001 |
| WO | WO-02/101412 A2 | 12/2002 |
| WO | WO-03/035827 A2 | 5/2003 |
| WO | WO-2004/002534 A1 | 1/2004 |
| WO | WO-2004/007537 A2 | 1/2004 |
| WO | WO-2004/035818 A1 | 4/2004 |
| WO | WO-2004/105790 A1 | 12/2004 |
| WO | WO-2004/108753 A1 | 12/2004 |
| WO | WO-2005/042029 A2 | 5/2005 |
| WO | WO-2005/056808 A2 | 6/2005 |
| WO | WO-2005/062709 A2 | 7/2005 |
| WO | WO-2006/081587 A2 | 8/2006 |
| WO | WO-2006/085082 A1 | 8/2006 |
| WO | WO-2006/092668 A2 | 9/2006 |
| WO | WO-2006/094974 A2 | 9/2006 |
| WO | WO-2006/127150 A2 | 11/2006 |
| WO | WO-2007/035455 A2 | 3/2007 |
| WO | WO-2007/038926 A1 | 4/2007 |
| WO | WO-2007/056847 A1 | 5/2007 |
| WO | WO-2007/095337 A2 | 8/2007 |
| WO | WO-2007/138135 A1 | 12/2007 |
| WO | WO-2007/149287 A2 | 12/2007 |
| WO | WO-2008/051245 A2 | 5/2008 |
| WO | WO-2008/058035 A1 | 5/2008 |
| WO | WO-2008/114021 A1 | 9/2008 |
| WO | WO-2008/118691 A2 | 10/2008 |
| WO | WO-2008/150479 A2 | 12/2008 |
| WO | WO-2009/006097 A1 | 1/2009 |
| WO | WO-2009/015343 A2 | 1/2009 |
| WO | WO-2009/129101 A1 | 10/2009 |
| WO | WO-2010/035001 A1 | 4/2010 |
| WO | WO-2010/146598 A2 | 12/2010 |
| WO | WO-2011/109415 A2 | 9/2011 |
| WO | WO-2011/121301 A1 | 10/2011 |
| WO | WO-2011/121305 A2 | 10/2011 |
| WO | WO-2011/121306 A1 | 10/2011 |
| WO | WO-2013/050780 A1 | 4/2013 |

OTHER PUBLICATIONS

Lloyd et al., "A Comparison of Glycine, Sarcosine, N,N-Dimethylglycine, Glycinebetaine and N-Modified Betaines as Liposome Cryoprotectants," J. Pharm. Pharmacol. 44: 507-511 (1992).*

Abdul-Fattah et al. The effect of annealing on the stability of amorphous solids: chemical stability of freeze-dried moxalactam. J Pharm Sci. May 2007;96(5):1237-50. (Year: 2007).*

Andersson et al., "Protein stabilising effect of polyethyleneimine" J Biotech. 72(1-2):21-31 (1999).

Andersson et al., "Stabilizing effect of chemical additives against oxidation of lactate dehydrogenase," Biotechnol Appl Biochem. 32:145-53 (2000).

Arakawa et al., "Factors affecting short-term and long-term stabilities of proteins ," Adv Drug Deliv Rev. 10:1-28 (1993).

Arakawa et al., "Factors affecting short-term and long-term stabilities of proteins," Adv Drug Deliv Rev. 46(1-3):307-26 (2001).

(56) References Cited

OTHER PUBLICATIONS

Berge et al., "Preservation of enteroviruses by freeze-drying," Appl Microbiol. 22(5):850-3 (1971).
Braun et al., "Development of a freeze-stable formulation for vaccines containing aluminum salt adjuvants," Vaccine. 27(1):72-9 (2009).
Brown et al., "Assembly of hybrid bacteriophage Qbeta virus-like particles," Biochemistry. 48(47):11155-7 (2009).
Bryjak et al., "Storage stabilization and purification of enzyme by water-soluble synthetic polymers," Enzyme Microb Technol. 16:616-21 (1994).
Bryjak, "Storage stabilization of enzyme activity by poly(ethyleneimine)," Bioprocess Eng. 13:177-81 (1995).
Carpenter et al., "The mechanism of cryoprotection of proteins by solutes," Cryobiology. 25(3):244-55 (1988).
Chen et al., "Stabilization of recombinant human keratinocyte growth factor by osmolytes and salts," J Pharm Sci. 85(4):419-22 (1996).
Cleland et al., "Glycine betaine as a cryoprotectant for prokaryotes," J Microbiol Methods. 58(1):31-8 (2004).
"Composition of Medium 199," XP002596423 (2009). Retrieved from the Internet: <URL:http://www.fishersci.com/wps/downloads/segment/Scientific/pdf/cmbrex_medium_199.pdf>.
Cosquer et al., "Nanomolar levels of dimethylsulfoniopropionate, dimethylsulfonioacetate, and glycine betaine are sufficient to confer osmoprotection to *Escherichia coli*," Appl Environ Microbiol. 65(8):3304-11 (1999).
Costantino et al., "Effect of excipients on the stability and structure of lyophilized recombinant human growth hormone," J Pharma Sci. 87(11):1412-20 (1998).
Drew et al., "Stable vaccine technology," displayed in Vienna Oct. 3-5, 2010.
Foreman et al., "Effects of charged water-soluble polymers on the stability and activity of yeast alcohol dehydrogenase and subtilisin Carlsberg," Biotechnol Bioeng. 76(3):241-6 (2001).
Greiff et al., "Effects of freezing, storage at low temperatures, and drying by sublimation in vacuo on the activities of measles virus," Nature. 202:624-5 (1964).
Gupta et al., "Stabilization of respiratory syncytial virus (RSV) against thermal inactivation and freeze-thaw cycles for development and control of RSV vaccines and immune globulin," Vaccine. 14(15):1417-20 (1996).
Holtmann et al., "Thermoprotection of Bacillus subtilis by exogenously provided glycine betaine and structurally related compatible solutes: involvement of Opu transporters," J Bacteriol. 186(6):1683-93 (2004).
Hubálek, "Protectants used in the cryopreservation of microorganisms," Cryobiology. 46(3):205-29 (2003).
Izutsu, "Stabilization of therapeutic proteins by chemical and physical methods" in *Therapeutic Proteins*, Smales and James ed. Humana Press ISBN 1-58829-390-4, 287-292 (2005).
Land et al., "The Challenges of Antimicrobial Preservation of a Sugar-free Liquid Risedronate Sodium Formulation for US and EMEA Pediatric Use," Post No. M1187. Procter & Gamble Pharmaceuticals, 2009 AAPS Natual Meeting and Exposition, Los Angeles, CA (2009).
Larski et al., "Stabilization of Newcastle disease virus by dimethyl sulfoxide," Acta Virol. 16(4):349-52 (1972).
Lever et al., "Using high-performance liquid chromatography to measure the effects of protein-stabilizing cosolvents on a model protein and fluorescent probes," Anal Biochem. 367(1):122-33 (2007).
Liao et al., "Influence of the active pharmaceutical ingredient concentration on the physical state of mannitol—implications in freeze-drying," Pharm Res. 22(11):1978-85 (2005). Abstract provided.
Liao et al., "Protective mechanism of stabilizing excipients against dehydration in the freeze-drying of proteins," Pharm Res. 19(12):1854-61(2002).

Manual of Policies and Procedures, Center for Drug Evaluation and Research, "Applications for Parenteral Products in Plastic Immediate Containers," MAPP 6020.2 (2007).
McGann et al., "Cryoprotection by dimethyl sulfoxide and dimethyl sulfone," Cryobiology. 24(1):11-6 (1987).
Nishigushi et al., "Temperature- and concentration-dependence of compatibility of the organic osmolyte beta-dimethylsulfoniopropionate," Cryobiology. 29(1):118-24 (1992).
Paleg et al., "Proline and glycine betaine influence protein solvation," Plant Physiol. 75(4):974-8 (1984).
Peek et al., "A rapid, three-step process for the preformulation of a recombinant ricin toxin A-chain vaccine," J Pharm Sci. 96(1):44-60 (2007).
Rathore et al. "Current perspectives on stability of protein drug products during formulation, fill and finish operations." Biotechnol Prog. 24(3):504-14 (2008).
Reichert et al., "Development trends for monoclonal antibody cancer therapeutics," Nat Rev Drug Discov. 6(5):349-56 (2007).
Sigalov, "Cryopreservation and long-term storage of human low density lipoproteins," Eur J Clin Chem Clin Biochem. 33(2):73-81 (1995).
Singh et al., "The osmoprotectants glycine and its methyl derivatives prevent the thermal inactivation of protective antigen of Bacillus anthracis," Biochem Biophys Res Comm. 316(2):559-64 (2004).
Sjölander et al., "ISCOMs: an adjuvant with multiple functions," J Leukoc Biol. 64(6):713-23 (1998).
Suntanto, et al. "Home delivery of heat stable vaccines in Indonesia: outreach immunization with a prefilled single use injection device" Bull. World. Health. Organ. 77(2):119-126 (1999).
Tiyaboonchai et al., "Insulin containing polyethylenimine-dextran sulfate nanoparticles," Int J Pharm. 255(1-2):139-51 (2003).
Wallis et al., "Stabilization of enveloped viruses by dimethyl sulfoxide," J Virol. 2(9):953-4 (1968).
Wolff et al., "Protection of aluminum hydroxide during lyophilisation as an adjuvant for freeze-dried vaccines," Colloids and Surfaces A: Physicochem. Eng Aspects. 330:116-26 (2008).
Wolff et al., "Comparative stability study of lyophilised aluminium hydroxide aduvanted vaccine formulations containing a monoclonal antibody as a model antigen and methods used for their characterisation," Colloids and Surfaces A: Physicochem. Eng Aspects. 339:82-93 (2009).
Wolff et al.,"Development of a formulation protecting aluminum hydroxide adjuvant vaccines during lyophilisation," 6th World Meeting on Pharmaceutics, Biopharmaceutics and Pharmaceutical Technology, Barcelona, Apr. 7-10, 2008.
Yancey, "Organic osmolytes as compatible, metabolic and counteracting cytoprotectants in high osmolarity and other stresses," J Exp Biol. 208:2819-30 (2005).
Stabilitech: "Stabilitech Technology," Innovations in Health, Nov. 19, 2009 (Nov. 19, 2009), Retrieved from the Internet: URL:http://www.cliqproject.eu/pubfilebank/savefile.php?folderId=118&fileId=374&key=85299185d6a857ba99cf6bf36db4c46f [retrieved on May 4, 2011].
U.S. Appl. No. 13/637,828, Drew et al.
U.S. Appl. No. 13/637,913, Drew et al.
U.S. Appl. No. 14/349,481, Drew et al.
"Renaturation (Molecular Biology)," <http://what-when-how.com/molecular-biology/renaturation-molecular-biology/>, retrieved on Nov. 15, 2015 (2 pages).
Burke et al., "Formulation, stability, and delivery of live attenuated vaccines for human use," Crit Rev Ther Drug Carrier Syst. 16(1):1-83 (1999).
Chang et al., "Mechanisms of protein stabilization in the solid state," J Pharm Sci. 98(9):2886-908 (2009).
Communication pursuant to Article 94(3) EPC for European Application No. 12772389.8, dated Oct. 21, 2015 (7 pages).
Davidson et al. "Effect of sucrose/raffinose mass ratios on the stability of co-lyophilized protein during storage above the Tg" Pharm Res. 18(4):474-9 (2001).
Izutsu et al., "Stabilization of protein structure in freeze-dried amorphous organic acid buffer salts," Chem Pharm Bull (Tokyo). 57(11):1231-6 (2009).

(56) References Cited

OTHER PUBLICATIONS

Kim et al., "Counteracting effects of renal solutes on amyloid fibril formation by immunoglobulin light chains," J Biol Chem. 276(2):1626-33 (2001).

Maltesen et al., "Drying methods for protein pharmaceuticals," Drug Disc Today Technol. 5(2-3):e81-8 (2008).

Pikal et al., "The effects of formulation variables on the stability of freeze-dried human growth hormone," Pharm Res. 8(4):427-36 (1991).

Popova et al., "Cryoprotective effect of glycine betaine and glycerol is not based on a single mechanism," Cryo Letters. 22(5):293-8 (2001).

Roy et al., "Freeze-drying of proteins: some emerging concerns," Biotechnol Appl Biochem. 39(Pt 2):165-77 (2004).

Tang et al., "Measurement of the kinetics of protein unfolding in viscous systems and implications for protein stability in freeze-drying," Pharm Res. 22(7):1176-85 (2005).

Tang et al., "The effect of stabilizers and denaturants on the cold denaturation temperatures of proteins and implications for freeze-drying," Pharm Res. 22(7):1167-75 (2005).

Tesconi et al., "Freeze-drying above room temperature," J Pharm Sci. 88(5):501-6 (1999).

The class notes from Indiana University on viral structure, http://courses.bio.indiana.edu/M430-Taylor/structure.html, retrieved on Apr. 13, 2015 (5 pages).

Mateu, "Assembly, stability and dynamics of virus capsids," Arch Biochem Biophys. 531(1-2):65-79 (2013).

Publication by Lymphomation.org, <http://www.lymphomation.org/side-effect-HAMA.htm>, accessed Dec. 2, 2017 (2 pages).

Suzuki et al., "Mammalian lactoferrin receptors: structure and function," Cell Mol Life Sci. 62(22):2560-75 (2005).

Breteler, "The MSM Miracle," available <http://www.msm-info.com/>, Jul. 2001 (13 pages).

Ishimaru et al., "Pressure-inactivated FMDV: a potential vaccine," Vaccine. 22(17-18):2334-9 (2004).

Michaelis et al., "Dimethylglycine buffer," J Biol Chem. 115:221-2 (1936).
Santoro et al., "Increased thermal stability of proteins in the presence of naturally occurring osmolytes," Biochemistry. 31(23):5278-83 (1992).
Schiefner et al., "Structural basis for the binding of compatible solutes by ProX from the hyperthermophilic archaeon *Archaeoglobus fulgidus*," J Biol Chem. 279(46):48270-81 (2004).

* cited by examiner

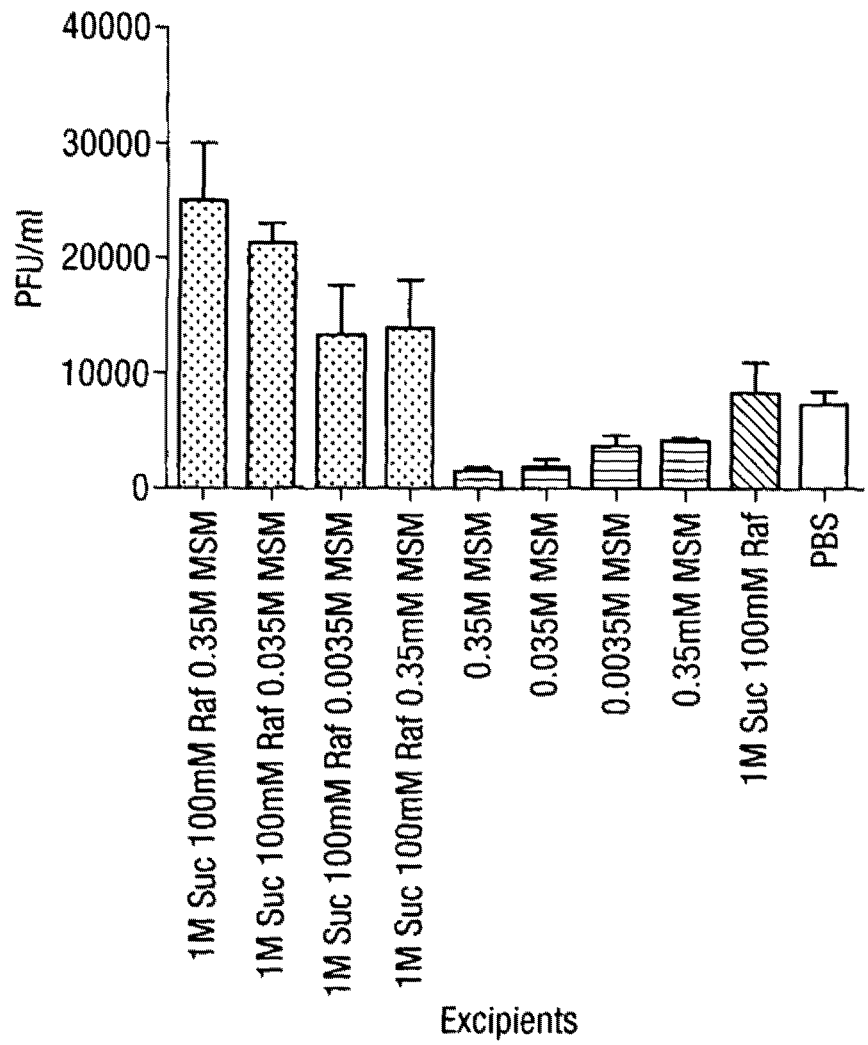

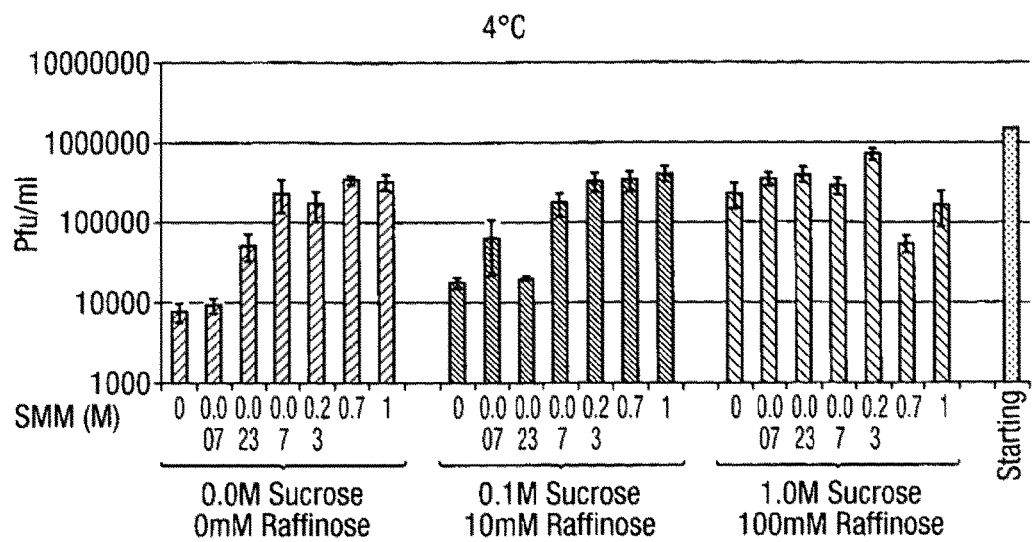
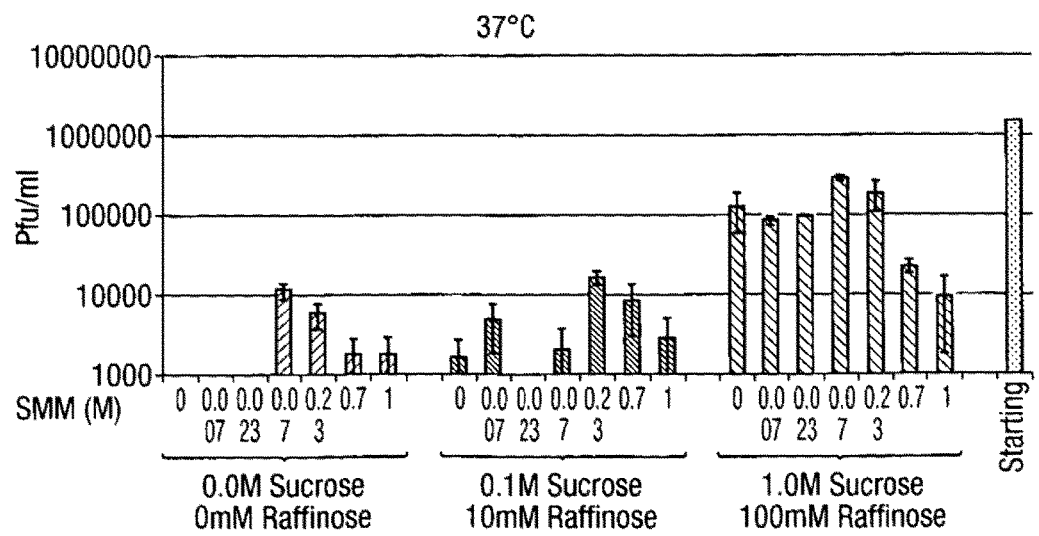

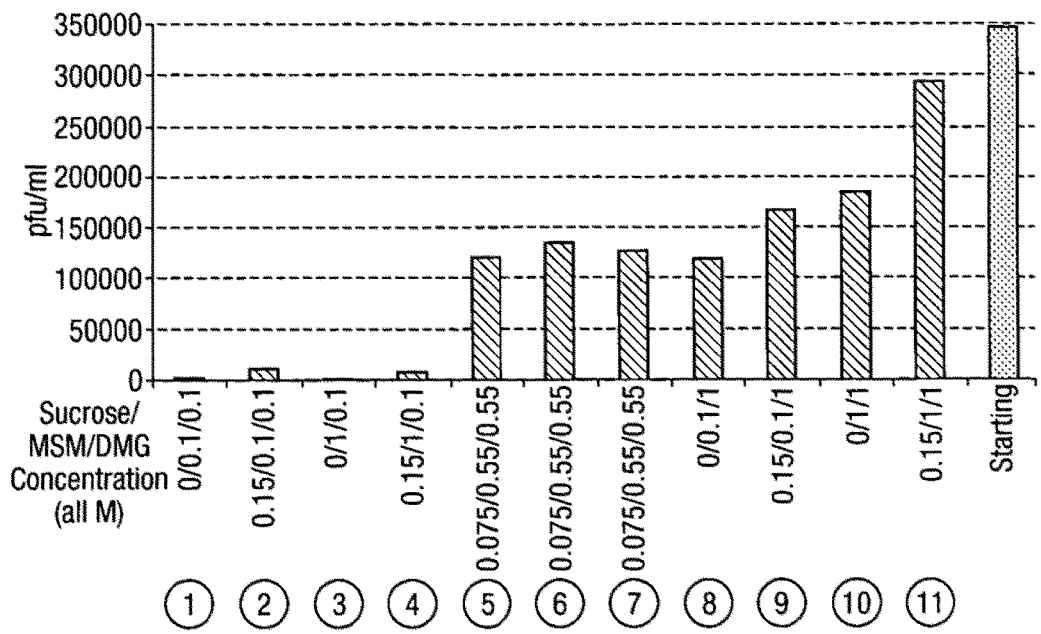
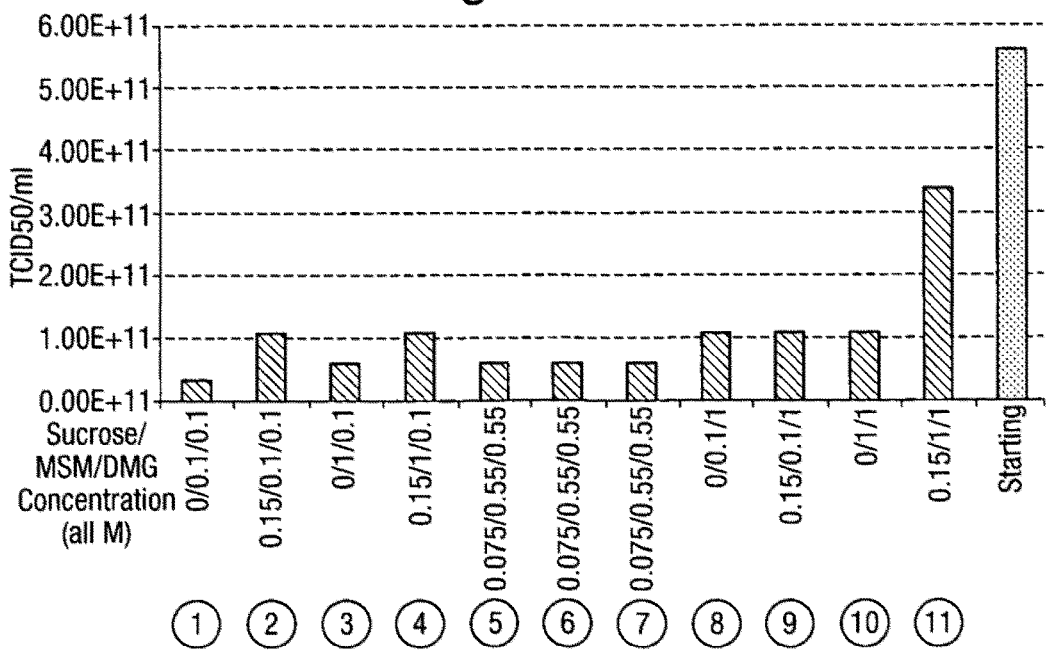

Fig. 17

Recipe Manager

File  Recipe  PrintScreen

Current Recipe: Read from Wizard 4        Read Complete

Recipe Number  4

| | Thermal Treatment | | |
|---|---|---|---|
| | Temp | Time | R/H |
| Step 1 | -40 | 120 | H |
| Step 2 | 0 | 0 | H |
| Step 3 | -99 | 0 | H |
| Step 4 | -99 | 0 | H |
| Step 5 | -99 | 0 | H |
| Step 6 | -99 | 0 | H |
| Step 7 | -99 | 0 | H |
| Step 8 | -99 | 0 | H |
| Step 9 | -99 | 0 | H |
| Step 10 | -99 | 0 | H |
| Step 11 | -99 | 0 | H |
| Step 12 | -99 | 0 | H |

| | Primary Drying | | |
|---|---|---|---|
| | Temp | Time | Vacuum | R/H |
| Step 1 | -45 | 15 | 300 | H |
| Step 2 | -34 | 30 | 300 | R |
| Step 3 | -34 | 1200 | 300 | H |
| Step 4 | -20 | 120 | 300 | H |
| Step 5 | -10 | 120 | 300 | H |
| Step 6 | 0 | 120 | 300 | H |
| Step 7 | 10 | 120 | 80 | H |
| Step 8 | 20 | 120 | 80 | H |
| Step 9 | 30 | 1255 | 80 | H |
| Step 10 | 30 | 905 | 80 | H |
| Step 11 | 4 | 1255 | 0 | H |
| Step 12 | -99 | 0 | 0 | H |
| Step 13 | -99 | 0 | 0 | H |
| Step 14 | -99 | 0 | 0 | H |
| Step 15 | -99 | 0 | 0 | H |
| Step 16 | -99 | 0 | 0 | H |

Post Ht  99  1000  1000

| Freeze | -45 |
|---|---|
| Extra Freeze | 0 |
| Condenser | -42 |
| Vacuum | 300 |

Secondary SP  35

F2 Synoptic
F3 PC Save
F4 Print
F7 Write
F8 Read

Fig. 28

Recipe Manager

File  Recipe  PrintScreen

Current Recipe: Read from Wizard 1    Read Complete

Recipe Number: 1

Thermal Treatment

| | Temp | Time | R/H |
|---|---|---|---|
| Step 1 | -40 | 120 | H |
| Step 2 | 0 | 0 | R |
| Step 3 | 0 | 0 | R |
| Step 4 | 0 | 0 | R |
| Step 5 | 0 | 0 | R |
| Step 6 | 0 | 0 | R |
| Step 7 | 0 | 0 | R |
| Step 8 | 0 | 0 | R |
| Step 9 | 0 | 0 | R |
| Step 10 | 0 | 0 | R |
| Step 11 | 0 | 0 | R |
| Step 12 | 0 | 0 | R |

Primary Drying

| | Temp | Time | Vacuum | R/H |
|---|---|---|---|---|
| Step 1 | -45 | 15 | 100 | H |
| Step 2 | -36 | 30 | 100 | R |
| Step 3 | -36 | 600 | 100 | H |
| Step 4 | -36 | 1200 | 100 | H |
| Step 5 | -36 | 5 | 100 | H |
| Step 6 | -10 | 120 | 100 | H |
| Step 7 | 0 | 120 | 80 | H |
| Step 8 | 10 | 120 | 80 | H |
| Step 9 | 20 | 120 | 80 | H |
| Step 10 | 25 | 1255 | 80 | H |
| Step 11 | 4 | 1255 | 80 | H |
| Step 12 | 4 | 1255 | 80 | H |
| Step 13 | 4 | 1255 | 80 | H |
| Step 14 | 4 | 1255 | 80 | H |
| Step 15 | 0 | 0 | 0 | H |
| Step 16 | 0 | 0 | 0 | H |

Post Ht: 35 | 1000 | 450

Freeze: -40
Extra Freeze: 0
Condenser: -42
Vacuum: 300

Secondary SP: 35

F2 Synoptic
F3 PC Save
F4 Print
F7 Write
F8 Read

Fig. 34

Recipe Manager

File  Recipe  PrintScreen

Current Recipe:   Read from Wizard 1    Read Complete

Recipe Number: 1

| | Thermal Treatment | | | Primary Drying | | | |
|---|---|---|---|---|---|---|---|
| | Temp | Time | R/H | Temp | Time | Vacuum | R/H |
| Step 1 | -40 | 120 | H | -45 | 15 | 100 | H |
| Step 2 | 0 | 0 | R | -36 | 30 | 100 | R |
| Step 3 | 0 | 0 | R | -36 | 600 | 100 | H |
| Step 4 | 0 | 0 | R | -36 | 1200 | 100 | H |
| Step 5 | 0 | 0 | R | -36 | 5 | 100 | H |
| Step 6 | 0 | 0 | R | -10 | 120 | 100 | H |
| Step 7 | 0 | 0 | R | 0 | 120 | 100 | H |
| Step 8 | 0 | 0 | R | 10 | 120 | 80 | H |
| Step 9 | 0 | 0 | R | 20 | 120 | 80 | H |
| Step 10 | 0 | 0 | R | 25 | 1255 | 80 | H |
| Step 11 | 0 | 0 | R | 4 | 1255 | 80 | H |
| Step 12 | 0 | 0 | R | 4 | 1255 | 80 | H |
| Step 13 | | | | 4 | 1255 | 80 | H |
| Step 14 | | | | 4 | 1255 | 80 | H |
| Step 15 | | | | 0 | 0 | 0 | H |
| Step 16 | | | | 0 | 0 | 0 | H |

Freeze      -40
Extra Freeze  0
Condenser   -42
Vacuum      300

Secondary SP  35

Post Ht   35   1000   450

F2 Synoptic
F3 PC Save
F4 Print
F7 Write
F8 Read

Fig. 39

Recipe Manager

File  Recipe  PrintScreen

Current Recipe: [    ]   Read from Wizard 1   Read Complete

Recipe Number [ 1 ]

Thermal Treatment

|        | Temp | Time | R/H |
|--------|------|------|-----|
| Step 1 | -40  | 120  | H   |
| Step 2 | 0    | 0    | R   |
| Step 3 | 0    | 0    | R   |
| Step 4 | 0    | 0    | R   |
| Step 5 | 0    | 0    | R   |
| Step 6 | 0    | 0    | R   |
| Step 7 | 0    | 0    | R   |
| Step 8 | 0    | 0    | R   |
| Step 9 | 0    | 0    | R   |
| Step 10| 0    | 0    | R   |
| Step 11| 0    | 0    | R   |
| Step 12| 0    | 0    | R   |

| Freeze        | -40 |
|---------------|-----|
| Extra Freeze  | 0   |
| Condenser     | -42 |
| Vacuum        | 300 |

Primary Drying

|         | Temp | Time | Vacuum | R/H |
|---------|------|------|--------|-----|
| Step 1  | -45  | 15   | 100    | H   |
| Step 2  | -36  | 30   | 100    | R   |
| Step 3  | -36  | 600  | 100    | H   |
| Step 4  | -36  | 1200 | 100    | H   |
| Step 5  | -36  | 5    | 100    | H   |
| Step 6  | -10  | 120  | 100    | H   |
| Step 7  | 0    | 120  | 80     | H   |
| Step 8  | 10   | 120  | 80     | H   |
| Step 9  | 20   | 120  | 80     | H   |
| Step 10 | 25   | 1255 | 80     | H   |
| Step 11 | 4    | 1255 | 80     | H   |
| Step 12 | 4    | 1255 | 80     | H   |
| Step 13 | 4    | 1255 | 80     | H   |
| Step 14 | 4    | 1255 | 0      | H   |
| Step 15 | 0    | 0    | 0      | H   |
| Step 16 | 0    | 0    | 0      | H   |

Post Ht  [ 35 ]  [ 1000 ]  [ 450 ]

Secondary SP [ 35 ]

F2 Synoptic
F3 PC Save
F4 Print
F7 Write
F8 Read

Fig. 44

Recipe Manager

File  Recipe  PrintScreen

Current Recipe:   Read from Wizard 6         Read Complete

Recipe Number  6

Thermal Treatmennt

| | Temp | Time | R/H |
|---|---|---|---|
| Step 1 | -40 | 45 | H |
| Step 2 | 0 | 0 | H |
| Step 3 | -99 | 0 | H |
| Step 4 | -99 | 0 | H |
| Step 5 | -99 | 0 | H |
| Step 6 | -99 | 0 | H |
| Step 7 | -99 | 0 | H |
| Step 8 | -99 | 0 | H |
| Step 9 | -99 | 0 | H |
| Step 10 | -99 | 0 | H |
| Step 11 | -99 | 0 | H |
| Step 12 | -99 | 0 | H |

Primary Drying

| | Temp | Time | Vacuum | R/H |
|---|---|---|---|---|
| Step 1 | -45 | 15 | 200 | H |
| Step 2 | -36 | 600 | 300 | H |
| Step 3 | -20 | 120 | 300 | R |
| Step 4 | -10 | 120 | 300 | R |
| Step 5 | 0 | 120 | 300 | R |
| Step 6 | 10 | 120 | 80 | R |
| Step 7 | 20 | 120 | 80 | R |
| Step 8 | 30 | 1255 | 80 | R |
| Step 9 | 4 | 1255 | 0 | R |
| Step 10 | 0 | 0 | 0 | H |
| Step 11 | -99 | 0 | 0 | H |
| Step 12 | -99 | 0 | 0 | H |
| Step 13 | -99 | 0 | 0 | H |
| Step 14 | -99 | 0 | 0 | H |
| Step 15 | -99 | 0 | 0 | H |
| Step 16 | -99 | 0 | 0 | H |

Post Ht   4   1000   1000

Freeze       -40
Extra Freeze   0
Condenser   -42
Vacuum     2000

Secondary SP   35

F2 Synoptic
F3 PC Save
F4 Print
F7 Write
F8 Read

STABILISATION OF VIRAL PARTICLES

CROSS REFERENCE TO RELATED APPLICATIONS

This application is the U.S. national stage filing under 35 U.S.C. § 371 of international application PCT/GB2011/000498, filed Mar. 31, 2011, which claims benefit of Great Britain Application Nos. 1005521.8, filed Mar. 31, 2010, 1005520.0, filed Mar. 31, 2010, 1005497.1, filed Mar. 31, 2010, 1014962.3, filed Sep. 8, 2010, 1017648.5, filed Oct. 19, 2010, 1017647.7, filed Oct. 19, 2010, and European Patent Application No. 10250706.8, filed Mar. 31, 2010.

FIELD OF THE INVENTION

The invention relates to the stabilisation of viral particles.

BACKGROUND TO THE INVENTION

Some biological molecules are sufficiently stable that they can be isolated, purified and then stored in solution at room temperature. However, this is not possible for many materials and techniques involving storage at low temperature, addition of stabilizers or cryoprotectants, freeze-drying, vacuum-drying and air-drying have been tried to ensure shelf preservation.

Despite the availability of these techniques, some biological materials still show unsatisfactory levels of stability during storage and some techniques lead to added cost and inconvenience. For example, refrigerated transportation and storage is expensive, and any breaks in temperature control can result in reduced efficacy of the biological molecule. Further, refrigerated transport is often not available for the transport of medicines in countries in the developing world.

Also, the stresses of freeze-drying or lyophilisation can be very damaging to some biological materials. Freeze drying of biopharmaceuticals involves freezing solutions or suspensions of thermosensitive biomaterials, followed by primary and secondary drying. The technique is based on sublimation of water at subzero temperature under vacuum without the solution melting. Freeze-drying represents a key step for manufacturing solid protein and vaccine pharmaceuticals. The rate of water vapour diffusion from the frozen biomaterial is very low and therefore the process is time-consuming. Additionally, both the freezing and drying stages introduce stresses that are capable of unfolding or denaturing proteins.

WO 90/05182 describes a method of protecting proteins against denaturation on drying. The method comprises the steps of mixing an aqueous solution of the protein with a soluble cationic polyelectrolyte and a cyclic polyol and removing water from the solution. Diethylaminoethyldextran (DEAE-dextran) and chitosan are the preferred cationic polyelectrolytes, although polyethyleneimine is also mentioned as suitable.

WO-A-2006/0850082 reports a desiccated or preserved product comprising a sugar, a charged material such as a histone protein and a desiccation- or thermosensitive biological component. The sugar forms an amorphous solid matrix. However, the histone may have immunological consequences if the preserved biological component is administered to a human or animal.

WO 2008/114021 describes a method for preserving viral particles. The method comprises drying an aqueous solution of one or more sugars, a polyethyleneimine and the viral particles to form an amorphous solid matrix comprising the viral particles. The aqueous solution contains the polyethyleneimine at a concentration of 15 μM or less based on the number-average molar mass ($M_n$) of the polyethyleneimine and the sugar concentration or, if more than one sugar is present, total sugar concentration is greater than 0.1M.

SUMMARY OF THE INVENTION

The present inventors have found that viral preparations are preserved stably by compounds of formula (I) and/or (II) as defined herein or physiologically acceptable salts or esters thereof and optionally one or more sugars during drying. Virus activity was preserved following subsequent heat challenge. Virus activity was also preserved during long-term stability tests. Virus activity may also be preserved in the aqueous solution prior to drying. The viruses were protected against damage caused by freezing, freeze-drying and thawing.

Accordingly, the present invention provides a method for preserving viral particles comprising:
(a) providing an aqueous solution of (i) viral particles, (ii) optionally one or more sugars, and (iii) a compound of formula (I) or a physiologically acceptable salt or ester thereof.

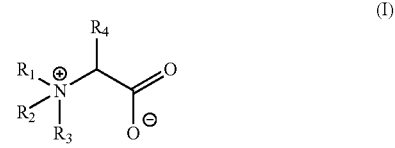

wherein:
$R_1$ represents hydrogen or $C_{1-6}$ alkyl; and
$R_4$ represents hydrogen; or
$R_1$ and $R_4$ together with the atoms to which they are attached form a pyrrolidine ring;
$R_2$ represents hydrogen, $C_{1-6}$ alkyl or —(CH$_2$)$_{2-5}$NHC(O)(CH$_2$)$_{5-15}$CH$_3$; and $R_3$ represents $C_{1-6}$ alkyl;
and/or
a compound of formula (II) or a physiologically acceptable salt or ester thereof

wherein:
X represents —S(O)$_2$— or —S$^+$(R$_c$)—;
$R_a$ and $R_b$ independently represent $C_{1-6}$ alkyl; and
$R_c$ represents $C_{1-6}$ alkyl substituted with a carboxylate anion and with an amine (—NH$_2$) moiety; and
(b) drying the solution to form a composition incorporating said viral particles.

The invention further provides:
a composition which comprises a compound of formula (I) or a physiologically acceptable salt or ester thereof and/or a compound of formula (II) or a physiologically acceptable salt or ester thereof and optionally one or more sugars and which incorporates viral particles;
a vaccine comprising a composition of the invention which incorporates non-infectious viral particles and optionally an adjuvant;
a method of preparing a vaccine which incorporates viral particles, which method comprises:

(a) providing an aqueous solution of (i) viral particles, (ii) a compound of formula (I) or a physiologically acceptable salt or ester thereof and/or a compound of formula (II) or a physiologically acceptable salt or ester thereof and (iii) optionally one or more sugars; and (b) optionally adding an adjuvant, buffer, antibiotic and/or additive to the admixture; and (c) drying the solution to form a composition or solid composition incorporating said viral particles;

a composition or dry powder which comprises viral particles or non-infectious viral particles and which is obtainable by a method of the invention;

a sealed vial or ampoule containing a composition of the invention;

use of a compound of formula (I) or a physiologically acceptable salt or ester thereof and/or a compound of formula (II) or a physiologically acceptable salt or ester thereof and, optionally, one or more sugars for preserving viral particles;

a method for preserving viral particles prior to drying comprising: (a) providing an aqueous solution of (i) viral particles, (ii) optionally one or more sugars, and (iii) a compound of formula (I) of the invention or a physiologically acceptable salt or ester thereof and/or a compound of formula (II) of the invention or a physiologically acceptable salt or ester thereof; and (b) storing the solution for up to five years in a sealed container;

a bulk aqueous solution of (i) viral particles, (ii) optionally one or more sugars, and (iii) a compound of formula (I) or a physiologically acceptable salt or ester thereof of the invention and/or a compound of formula (II) of the invention or a physiologically acceptable salt or ester thereof, which solution is provided in a sealed container and is stored prior to drying in a refrigerator or freezer;

use of a compound of formula (I) or a physiologically acceptable salt or ester thereof of the invention and/or a compound of formula (II) or a physiologically acceptable salt or ester thereof of the invention and, optionally, one or more sugars for preserving viral particles in an aqueous solution which comprises said viral particles, prior to drying; and use of a compound of formula (I) or a physiologically acceptable salt or ester thereof and/or a compound of formula (II) or a physiologically acceptable salt or ester thereof and, optionally, one or more sugars as a resuspension agent for a composition which is a dried or freeze-dried product comprising viral particles.

BRIEF DESCRIPTION OF THE FIGURES

FIG. 3 shows the results of the experiment of Example 2 that investigated the effect of sugars and MSM on preservation of adenovirus during freeze drying. The error bars shown are the standard error of the mean (n=3).

FIG. 6 shows bar graphs demonstrating the virus titres of reconstituted samples used in Example 4 following thermal challenge at 4° C. or 37° C. for 7 days. The starting titre of the input virus is also shown. The error bars represent standard error of the mean (n=3).

FIG. 14 shows the results obtained in Example 10 in which the ability of eleven formulations to stabilise adenovirus through freeze-drying and thermal challenge was assessed.

FIG. 15 shows the results obtained in Example 11 in which the ability of eleven formulations to stabilise MVA through freeze-drying and thermal challenge was assessed.

FIGS. 17 and 18 show the freeze-drying program used in Example 12 and temperature readings from sensors during that program.

FIG. 28 shows the freeze-drying program used in Example 13.

FIG. 33A is a contour plot where a cross marks the predicted optimum. FIG. 33B is an identical graph region highlighting region of the model where predicted recovered viral activity is greater than or equal to initial activity.

FIG. 34 shows the freeze-drying program used in Example 14.

FIG. 39 shows the lyophilisation conditions used in Example 15.

FIG. 44 shows the lyophilisation conditions used in Example 16.

DETAILED DESCRIPTION OF THE INVENTION

Summary

Figure 1:
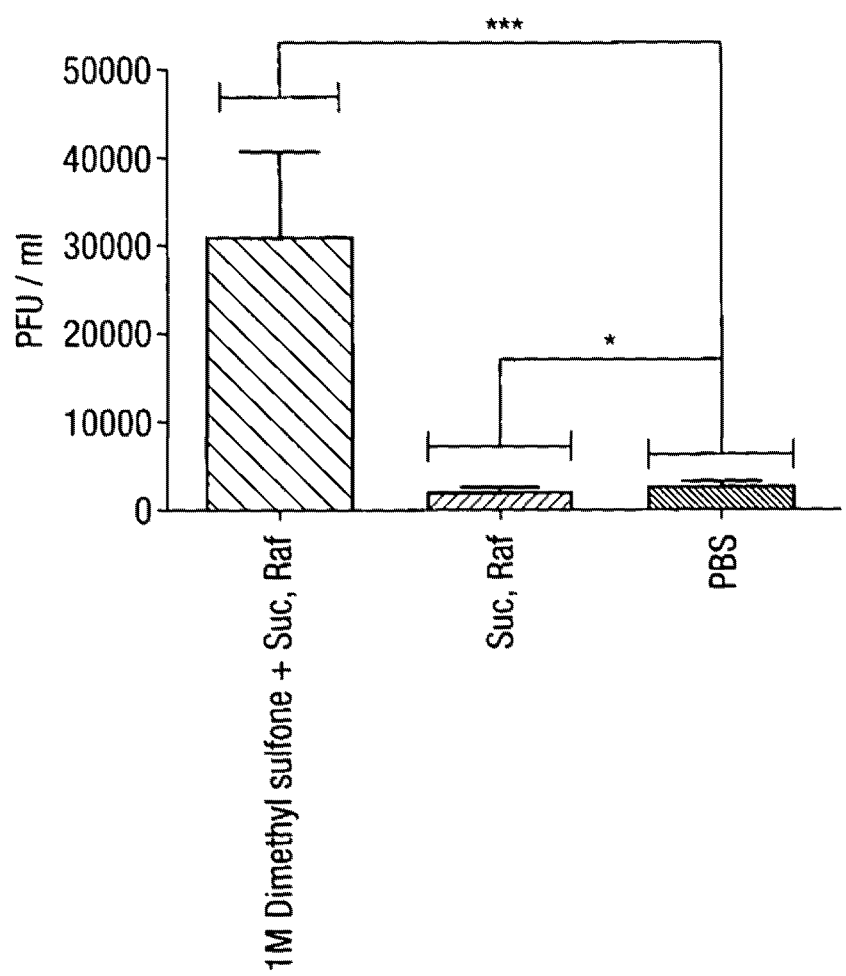
FIG. 1 shows the results obtained in Example 1. The ability of an excipient to help adenovirus withstand cycling between 37° C. and −20° C. was assessed. Dimethylsulfone (also called methylsulfonylmethane, MSM) was used as an excipient. p value summary: **=p<0.01, *=p<0.05. The error bars show the standard error of the mean (n=4).

The present invention relates to the preservation of viral particles by a compound of formula (I) or a physiologically acceptable salt or ester thereof and/or a compound of formula (II) or a physiologically acceptable salt or ester thereof and optionally one, two or more sugars. The viral particles are contacted with the compound of formula (I) or a physiologically acceptable salt or ester thereof and/or compound of formula (II) or a physiologically acceptable salt or ester thereof and optionally one or more sugars in an aqueous solution and the resulting solution in which the viral particles are present is then dried to form a composition incorporating the viral particles.

The viral particles may therefore be admixed with an aqueous solution ("preservation mixture") of the compound of formula (I) or a physiologically acceptable salt or ester thereof and/or compound of formula (II) or a physiologically acceptable salt or ester thereof and optionally one or more sugars. The resulting solution is then dried to form a composition incorporating the viral particles. The dried composition may take the form of a cake or powder. The cake can be milled to a powder if required.

The invention enables virus structure and function to be preserved during the drying step. Virus activity following drying can thus be maintained. The presence of a compound of formula (I) or a physiologically acceptable salt or ester thereof and/or a compound of formula (II) or a physiologically acceptable salt or ester thereof alone allows preservation of viral activity. Further improvements in preservation of viral activity can be achieved by use of one or more sugars in combination with a compound of formula (I) or a physiologically acceptable salt or ester thereof and/or a compound of formula (II) or a physiologically acceptable salt or ester thereof.

The preserved viral particles demonstrate improved thermal resistance allowing extension of shelf life, ease of storage and transport and obviating the need for a cold chain for distribution. The invention can thus provide protection as a cryoprotectant (protection against freeze damage), lyoprotectant (protection during freeze-drying) and/or a thermoprotectant (protection against temperatures higher or lower than 4° C.).

In addition, the viral particles are preserved in the aqueous solution prior to the drying step. This allows the aqueous solution to be stored after preparation, until such time as the drying step can be carried out, without undue loss of viral activity.

Viral Particles

The viral particles used in the present invention may be whole viruses such as live viruses, killed viruses, live attenuated viruses, inactivated viruses such as chemically inactivated viruses or virulent or non-virulent viruses. A live virus is capable of infecting and replicating within the host cell. A killed virus is inactivated and is unable to replicate within the host cell. The particles may be virus-like particles (VLPs) or nucleocapsids. The virus may be infectious to prokaryotic or eukaryotic cells. The virus may be a human or animal virus.

The viral particle may be, or may be derived from, a dsDNA virus, a ssDNA virus, a dsRNA virus, a (+)ssRNA virus, a (−)ssRNA virus, a ssRNA-RT virus or a dsDNA-RT virus. As an example but not intended to be limiting, the viral particle can be, or can be derived from, a virus of the following families:

- Adenoviridae such as a human adenovirus or non-human adenovirus, for example human adenovirus A, B, C, D, E or F including human Ad5, Ad2, Ad4, Ad6, Ad7, Ad11, Ad14, Ad24, Ad26, Ad35 and Ad36 serotypes;
- Caliciviridae such as the norwalk virus;
- Coronaviridae such as human coronavirus 299E or OC43 and SARS-coronavirus;
- Filoviridae such as ebola virus;
- Flaviviridae such as yellow fever virus, west nile virus, dengue virus, hepatitis C virus;
- Hepadnaviridae such as hepatitis B virus;
- Herpesviridae such as herpes simplex virus e.g. HSV1 or HSV2, human herpesvirus 1, 3, 4, 5 or 6;
- Orthomyxoviridae such as influenzavirus A, B, C including but not limited to influenza A virus serotypes H1N1, H2N2, H3N2, H5N1, H7N7, H1N2, H9H2, H7N2, $H_7N_3$ and N10N7;
- Papillomaviridae such as human papilloma virus;
- Paramyxoviridae such as human parainfluenza virus 1, measles virus and mumps virus;
- Parvoviridae such as adeno-associated virus;
- Picornaviridae such as human poliovirus, foot and mouth disease virus (including serotypes O, A, C, SAT-1, SAT-2, SAT-3 and Asia-1);
- Poxyiridae such as vaccinia virus, variola virus and avian poxvirus (fowlpox);
- Reoviridae such as bluetongue virus group;
- Retroviridae such as lentivirus including human immunodeficiency virus 0.1 and 2; and
- Togaviridae such as rubella virus.

In a preferred embodiment, the viral particle can be or can be derived from an Adenoviridae, Orthomyxoviridae, Paramyxoviridae, Parvoviridae, Picornaviridae or Poxyiridae virus. In a particularly preferred embodiment, the viral particle can be or can be derived from an adenovirus, vaccinia virus, influenza virus, or measles virus. The virus can be Modified Vaccinia Virus Ankara (MVA) or a viral particle derived from MVA.

Virus-like particles (VLPs) include viral proteins derived from the structural proteins of a virus, but lack viral nucleic acid. When overexpressed, these viral structural proteins spontaneously self-assemble into particles. VLPs are replication incompetent. In some embodiments, the VLPs are viral proteins embedded within a lipid bilayer. Examples of VLPs includes phage-derived VLPs, human papillomavirus (HPV) L1 major capsid protein VLPs, Norwalk virus capsid protein VLPs and VLPs assembled from influenza virus structural proteins such as M1 protein, HA hemagglutinin protein and N1 neuraminidase protein.

Viral particles can be prepared using standard techniques well known to those skilled in the art. For example, a virus may be prepared by infecting cultured host cells with the virus strain that is to be used, allowing infection to progress such that the virus replicates in the cultured cells and can be released by standard methods known in the art for harvesting and purifying viruses.

Compounds of Formula (I) or Physiologically Acceptable Salts or Esters Thereof and Compounds of Formula (II) or Physiologically Acceptable Salts or Esters Thereof The compounds of formula (I) and (II) may be present as a physiologically acceptable salt or ester thereof.

The salt is typically a salt with a physiologically acceptable acid and thus includes those formed with an inorganic acid such as hydrochloric or sulphuric acid or an organic acid such as citric, tartaric, malic, maleic, mandelic, fumaric or methanesulphonic acid. The hydrochloride salt is preferred.

The ester is typically a $C_{1-6}$ alkyl ester, preferably a $C_{1-4}$ alkyl ester. The ester may therefore be the methyl, ethyl, propyl, isopropyl, butyl, isobutyl or tert-butyl ester. The ethyl ester is preferred.

As used herein, a $C_{1-6}$ alkyl group is preferably a $C_{1-4}$ alkyl group. Preferred alkyl groups are selected from methyl, ethyl, propyl, isopropyl, butyl, isobutyl and tert-butyl. Methyl and ethyl are particularly preferred.

For the avoidance of doubt, the definitions of compounds of formula (I) and formula (II) also include compounds in which the carboxylate anion is protonated to give —COOH and the ammonium or sulfonium cation is associated with a pharmaceutically acceptable anion. Further, for the avoidance of doubt, the compounds defined above may be used in any tautomeric or enantiomeric form.

Compounds of Formula (I)

Typically, $R_1$ represents hydrogen or $C_{1-6}$ alkyl and $R_4$ represents hydrogen. Typically, $R_2$ represents hydrogen or $C_{1-6}$ alkyl. Preferably, $R_1$ represents hydrogen or $C_{1-6}$ alkyl, $R_4$ represents hydrogen and $R_2$ represents hydrogen or $C_{1-6}$ alkyl. More preferably $R_1$ represents hydrogen or $C_{1-6}$ alkyl, $R_4$ represents hydrogen and $R_2$ represents $C_{1-6}$ alkyl.

Preferably, the compound of formula (I) is an N—$C_{1-6}$ alkyl-, N,N-di($C_{1-6}$ alkyl)- or N,N,N-tri($C_{1-6}$ alkyl)-glycine or physiologically acceptable salt or ester thereof, more preferably an N,N-di($C_{1-6}$ alkyl)- or N,N,N-tri($C_{1-6}$ alkyl)-glycine or physiologically acceptable salt or ester thereof. The alkyl group is typically a $C_{1-4}$ alkyl group. Preferred alkyl groups are selected from methyl, ethyl, propyl, isopropyl, butyl, isobutyl and tert-butyl. Methyl and ethyl are particularly preferred.

Preferred compounds of formula (I) are N-methylglycine, N,N-dimethylglycine or N,N,N-trimethylglycine or physiologically acceptable salts or esters thereof. N-Methylglycine is also called sarcosine. N,N-Dimethylglycine is also termed dimethylglycine (DMG) or 2-(dimethylamino)-acetic acid. N,N,N-trimethylglycine is termed trimethylglycine (TMG).

Alternatively, the compound of formula (I) is typically a glycine derivative of formula (IA) or a physiologically acceptable salt or ester thereof:

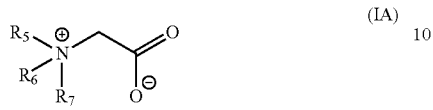

wherein $R_5$ and $R_6$ independently represent $C_{1-6}$ alkyl, for example $C_{1-4}$ alkyl such as methyl or ethyl; and $R_7$ represents $C_{1-6}$ alkyl, for example $C_{1-4}$ alkyl such as methyl or ethyl, or —$(CH_2)_{2-5}NHC(O)(CH_2)_{5-15}CH_3$. Preferred compounds of formula (IA) are trimethylglycine (TMG) and cocamidopropyl betaine (CAPB) or physiologically acceptable salts or esters thereof. Trimethyglycine is preferred.

Alternatively, the compound of formula (I) is typically a proline derivative of formula (IB) or a physiologically acceptable salt or ester thereof:

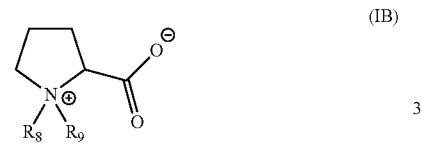

wherein $R_8$ and $R_9$ independently represent $C_{1-6}$ alkyl, for example $C_{1-4}$ alkyl such as methyl or ethyl. Preferably the compound of formula (IB) is an S-proline derivative. Preferably $R_8$ and $R_9$ both represent methyl; this compound is known as proline betaine. S-proline betaine or physiologically acceptable salt or ester thereof is particularly preferred:

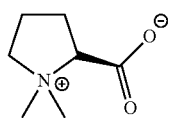

Compounds of formula (IA) or physiologically acceptable salts or esters thereof are preferred.

Preferably, the compound of formula (I) is N,N-dimethylglycine or N,N,N-trimethylglycine or physiologically acceptable salt or ester thereof. Most preferably, the compound of formula (I) is N,N-dimethylglycine or physiologically acceptable salt or ester thereof.

Compounds of Formula (II)

Typically, the carboxylate and amine substituents of $R_c$ are attached to the same carbon atom of the $R_c$ alkyl moiety. Typically $R_c$ is a $C_{2-4}$ or $C_{2-3}$ alkyl moiety.

The compound of formula (II) is typically a sulfone compound of formula (IIA) or a physiologically acceptable salt or ester thereof:

wherein $R_c$ and $R_d$ independently represent $C_{1-6}$ alkyl, for example $C_{1-4}$ alkyl. Preferred alkyl groups are selected from methyl, ethyl, propyl, isopropyl, butyl, isobutyl and tert-butyl. Methyl and ethyl are particularly preferred. A preferred sulfone compound is methylsulfonylmethane (MSM), which is also known as dimethylsulfone ($DMSO_2$).

The compound of formula (II) is typically a compound of formula (IIB) or a physiologically acceptable salt or ester thereof:

$$\underset{R_f}{\overset{R_e}{\underset{|}{S^{\oplus}}}}R_g \quad \text{(IIB)}$$

wherein $R_e$ and $R_f$ independently represent $C_{1-6}$ alkyl, for example $C_{1-4}$ alkyl such as methyl or ethyl, and $R_g$ represents $C_{1-6}$ alkyl, for example $C_{1-4}$ alkyl such as methyl or ethyl, substituted with a carboxylate anion and with an amine (—$NH_2$) moiety. Preferably the carboxylate and amine substituents are attached to the same carbon atom. A preferred compound of formula (IIB) is S-methyl-L-methionine (SMM) or a physiologically acceptable salt or ester thereof.

Sugars

Sugars suitable for use in the present invention include reducing sugars such as glucose, fructose, glyceraldehydes, lactose, arabinose and maltose; and preferably non-reducing sugars such as sucrose and raffinose, more preferably sucrose. The sugar may be a monosaccharide, disaccharide, trisaccharide, or other oligosaccharides. The term "sugar" includes sugar alcohols. In one embodiment, therefore, use of a non-reducing sugar or a sugar alcohol is preferred.

Monosaccharides such as galactose and mannose; disaccharides such as sucrose, lactose and maltose; trisaccharides such as raffinose; and tetrasaccharides such as stachyose are envisaged. Trehalose, umbelliferose, verbascose, isomaltose, cellobiose, maltulose, turanose, melezitose and melibiose are also suitable for use in the present invention. A suitable sugar alcohol is mannitol. When mannitol is used, cakes of improved appearance can be obtained on freeze-drying.

The presence of sugar may act to improve stability. The addition of sugar may also provide other benefits such as an altered lyophilisation cake and improved solubility for faster reconstitution. Generally one or more sugars is present when freeze-drying is used. When one sugar is used, the sugar is preferably sucrose or mannitol, more preferably mannitol.

Preservation of viral activity is particularly effective when two or more sugars are used in the preservation mixture. Two, three or four sugars may be used. Preferably, the aqueous solution is a solution of sucrose and raffinose. Sucrose is a disaccharide of glucose and fructose. Raffinose is a trisaccharide composed of galactose, fructose and glucose.

Preservation Procedure

In the present invention, an aqueous solution comprising the viral particles, optionally one or more sugars and a compound of formula (I) or a physiologically acceptable salt or ester thereof and/or a compound of formula (II) or a physiologically acceptable salt or ester thereof is dried. Any suitable aqueous solution may be used. The solution may be buffered. The solution may be a HEPES, phosphate-buffered, Tris-buffered or pure water solution.

The solution may have a pH of from 2 to about 12 and may be buffered. The solution may be buffered with HEPES buffer, phosphate-buffer, Tris-buffer, sodium citrate buffer, bicine buffer (i.e. N,N-bis(2-hydroxyethyl)glycine buffer) or MOPS buffer (i.e. 3-(N-morpholino) propanesulfonic acid buffer). The solution may or may not contain NaCl. The solution may thus be a saline sodium citrate (SSC) buffered solution.

Generally a preparation of the viral particles is admixed with the preservation mixture, i.e. with an aqueous solution of a compound of formula (I) or a physiologically acceptable salt or ester thereof and/or a compound of formula (II) or a physiologically acceptable salt or ester thereof and optionally one, two or more sugars. The preservation mixture may itself be buffered. It may be a HEPES, phosphate-buffered, Tris-buffered or pure water solution.

Alternatively, the aqueous solution may typically consist, or consist essentially, of viral particles, a compound of formula (I) or a physiologically acceptable salt or ester thereof and/or a compound of formula (II) or a physiologically acceptable salt or ester thereof, and optionally one or more sugars.

The concentrations of the compound of formula (I) or a physiologically acceptable salt or ester thereof and/or a compound of formula (II) or a physiologically acceptable salt or ester thereof and of each optional sugar can be determined by routine experimentation. Optimised concentrations which result in the best stability can thus be selected. The compound of formula (I) or a physiologically acceptable salt or ester thereof and/or a compound of formula (II) or a physiologically acceptable salt or ester thereof compound may act synergistically to improve stability.

The concentration of sugar when present in the aqueous solution for drying is at least 0.01M, typically up to saturation. Generally the sugar concentration when present is at least 0.1M, at least 0.2M or at least 0.5M up to saturation e.g. saturation at room temperature or up to 3M, 2.5M or 2M. The sugar concentration may therefore range from, for example, 0.1M to 3M or 0.2M to 2M. Preferably a sugar is present. Alternatively, the sugar concentration or the total sugar concentration if more than one sugar is present may therefore range from 0.08M to 3M, from 0.15M to 2M or from 0.2M to 1M. A suitable range is from 0.05 to 1M.

When more than one sugar is present, preferably one of those sugars is sucrose. The sucrose may be present at a concentration of from 0.05M, 0.1M, 0.25M or 0.5M up to saturation e.g. saturation at room temperature or up to 3M, 2.5M or 2M.

The ratio of the molar concentration of sucrose relative to the molar concentration of the other sugar(s) is typically from 1:1 to 20:1 such as from 5:1 to 15:1. In the case when two sugars are present and in particular when sucrose and raffinose are present, therefore, the ratio of molar concentrations of sucrose is typically from 1:1 to 20:1 such as from 5:1 to 15:1 and preferably about 10:1.

The concentration of each compound of formula (I) or physiologically acceptable salt or ester thereof or compound of formula (II) or physiologically acceptable salt or ester thereof in the aqueous solution for drying is generally in the range of from 0.001M to 2.5M and more especially from 0.01M to 2.5M. For example, the concentration range may be from 0.1M to 2.5M.

Alternatively, for example when the compound of formula (I) is DMG or a salt or ester, the concentration of each compound of formula (I) or physiologically acceptable salt or ester thereof or compound of formula (II) or physiologically acceptable salt or ester thereof in the aqueous solution for drying is generally in the range of 0.1 mM to 3M or from 1 mM to 2M. The concentration may be from 1 mM to 1.5M or from 5 mM to 1M or from 0.07M to 0.7M. Preferred concentrations are from 7 mM to 1.5M or from 0.07M to 1.2M. Another further preferred range is 0.5 to 1.5M, particularly when the compound of formula (I) is an N-alkylated glycine derivative such as DMG.

The particular concentration of compound of formula (I) or physiologically acceptable salt or ester thereof or compound of formula (II) or physiologically acceptable salt or ester thereof that is employed will depend on several factors including the type of viral particle to be preserved; the particular compound being used; whether one, two more sugars are present and the identity of the sugar(s); and the drying procedure and conditions. Thus:

The concentration of a compound of formula (II) in which X represents —S(O)$_2$— or a compound of formula (IIA), such as MSM, or a physiologically acceptable salt or ester thereof is preferably from 0.2 mM to 1M such as from 0.35 mM to 1M, from 3.5 mM to 0.5M, from 0.035M to 0.5M or from 0.035M to 0.25M.

The concentration of a compound of formula (I) or a compound of formula (IA) or formula (IB), such as TMG, or a physiologically acceptable salt or ester thereof is preferably used at a concentration from 0.01M to 2M such as from 0.07M to 2M, from 0.2M to 1.5M, from 0.23M to 1.5M or from 0.07M to 0.7M.

The concentration of a compound of formula (II) in which X represents —S$^+$(R$_c$)— or a compound of formula (IIB), such as S-methyl-L-methionine, or a physiologically acceptable salt or ester thereof is preferably from 0.005M to 2M such as from 0.007M to 2M, from 0.02M to 2M, from 0.023M to 1.5M or from 0.07M to 1M.

The concentration of a compound of formula (I), such as N,N-dimethylglycine (DMG) or a physiologically acceptable salt or ester thereof, when no sugar is present are from 5 mM to 1.5M or from 70 mM to 1.5M or to 1.2M or from 7 mM to 1M. More preferred concentrations are from 0.023M to 0.7M or 1M, or from 0.07M to 0.7M or 1M, such as about 0.7M The concentration of a compound of formula (I), such as N,N-dimethylglycine (DMG) or a physiologically acceptable salt or ester thereof, when one or more sugars are present are generally lower and in the range of from 1 mM to 1M or 1.5M or from 5 mM to 1M. More preferred concentrations are from 0.007M to 0.7M or 1M such as about 0.007M. A particularly preferred range is 0.5 to 1.5M.

When a compound of formula (I) or physiologically acceptable salt or ester thereof and a compound of formula (II) or physiologically acceptable salt or ester thereof are present, and preferably when an N-alkylated glycine derivative or salt or ester thereof and a sulfone compound of formula (IIA) or (IIC) are present, the compounds can be present in amounts that result in synergy. For example:

The concentration of the N-alkylated glycine derivative or salt or ester thereof in the aqueous solution for drying is generally in the range of 0.1 mM to 3M or from 1 mM to 2M. The concentration may be from 1 mM to 1.5M or from 5 mM to 1M. Preferred concentrations are from 0.1M to 1.5M or from 0.5M to 1.25M.

The concentration of the sulfone compound of formula (IIA) or (IIC) in the aqueous solution for drying is generally in the range of 0.1 mM to 3M, from 1 mM to 2M or from 0.2 mM to 1M. The concentration may be from 0.1M to 1.5M or from 0.5M to 1.25M.

Typically, drying is achieved by freeze drying, vacuum drying, fluid bed drying or spray-drying. Freeze-drying is preferred. By reducing the water in the material and sealing the material in a vial, the material can be easily stored, shipped and later reconstituted to its original form. The drying conditions can be suitably optimized via routine experimentation.

On drying, a composition is formed which incorporates the viral particles. A matrix incorporating the viral particles is produced. The composition is typically an amorphous solid. A solid matrix, generally an amorphous solid matrix, is thus generally formed. By "amorphous" is meant non-structured and having no observable regular or repeated organization of molecules (i.e. non-crystalline).

The sugar or sugars when present provide the amorphous matrix in the dried composition. The compound of formula (I) or a physiologically acceptable salt or ester thereof and/or a compound of formula (II) or physiologically acceptable salt or ester thereof is dispersed in the sugar matrix. The compound of formula (I) or a physiologically acceptable salt or ester thereof and/or compound of formula (II) or physiologically acceptable salt or ester thereof is thus incorporated within the sugar matrix. The viral particles are incorporated within the sugar matrix too. The drying procedure can thus be effected e.g. by freeze-drying to form an amorphous cake within which the viral particles are incorporated.

The drying step is generally performed as soon as the aqueous solution has been prepared or shortly afterwards. Alternatively, the aqueous solution is typically stored prior to the drying step. The viral particle in the aqueous solution is preserved by the compound of formula (I) or a physiologically acceptable salt or ester thereof and/or a compound of formula (II) or physiologically acceptable salt or ester thereof and, optionally, one or more sugars during storage.

The aqueous solution, or bulk intermediate solution, is generally stored for up to 5 years, for example up to 4 years, 3 years, 2 years or 1 year. Preferably the solution is stored for up to 6 months, more preferably up to 3 months or up to 2 months, for example 1 day to 1 month or 1 day to 1 week. Prior to drying, the solution is typically stored in a refrigerator or in a freezer. The temperature of a refrigerator is typically 2 to 8° C., preferably 4 to 6° C., or for example about 4° C. The temperature of a freezer is typically −10 to −80° C., preferably −10 to −30° C., for example about −20° C.

The solution is typically stored in a sealed container, preferably a sealed inert plastic container, such as a bag or a bottle. The container is typically sterile. The volume of the bulk intermediate solution is typically 0.1 to 100 liters, preferably 0.5 to 100 liters, for example 0.5 to 50 liters, 1 to 20 liters or 5 to 10 liters. The container typically has a volume of 0.1 to 100 liters, preferably 0.5 to 100 liters, for example 0.5 to 50 liters, 1 to 20 liters or 5 to 10 liters.

If the stored bulk intermediate solution is to be freeze-dried, it is typically poured into a freeze-drying tray prior to the drying step.

Stable storage of the solution increases the flexibility of the manufacturing process. Thus, the solution can be easily stored, shipped and later dried.

Freeze-Drying

Freeze-drying is a dehydration process typically used to preserve perishable material or make the material more convenient for transport. Freeze-drying represents a key step for manufacturing solid protein and vaccine pharmaceuticals. However, biological materials are subject to both freezing and drying stresses during the procedure, which are capable of unfolding or denaturing proteins. Furthermore, the rate of water vapour diffusion from the frozen biological material is very low and therefore the process is time-consuming. The preservation technique of the present invention enables biological materials to be protected against the desiccation and/or thermal stresses of the freeze-drying procedure.

There are three main stages to this technique namely freezing, primary drying and secondary drying. Freezing is typically performed using a freeze-drying machine. In this step, it is important to cool the biological material below its eutectic point, (Teu) in the case of simple crystalline products or glass transition temperature (Tg') in the case of amorphous products, i.e. below the lowest temperature at which the solid and liquid phase of the material can coexist. This ensures that sublimation rather than melting will occur in the following primary drying stage.

During primary drying the pressure is controlled by the application of appropriate levels of vacuum whilst enough heat is supplied to enable the water to sublimate. At least 50%, typically 60 to 70%, of the water in the material is sublimated at this stage. Primary drying may be slow as too much heat could degrade or alter the structure of the biological material. A cold condenser chamber and/or condenser plates provide surfaces on which the water vapour is trapped by resolidification.

In the secondary drying process, water of hydration is removed by the further application of heat. Typically, the pressure is also lowered to encourage further drying. After completion of the freeze-drying process, the vacuum can either be broken with an inert gas such as nitrogen prior to sealing or the material can be sealed under vacuum.

Vacuum Drying

In certain embodiments, drying is carried out using vacuum desiccation at around 1300 Pa. However vacuum desiccation is not essential to the invention and in other embodiments, the preservation mixture contacted with the viral particle is spun (i.e. rotary desiccation) or freeze-dried (as further described below). Advantageously, the method of the invention further comprises subjecting the preservation mixture containing the viral particle to a vacuum. Conveniently, the vacuum is applied at a pressure of 20,000 Pa or less, preferably 10,000 Pa or less. Advantageously, the vacuum is applied for a period of at least 10 hours, preferably 16 hours or more. As known to those skilled in the art, the period of vacuum application will depend on the size of the sample, the machinery used and other parameters.

Spray-Drying and Spray Freeze-Drying

In another embodiment, drying is achieved by spray-drying or spray freeze-drying the viral particles admixed with the preservation mixture of the invention. These techniques are well known to those skilled in the art and involve a method of drying a liquid feed through a gas e.g. air, oxygen-free gas or nitrogen or, in the case of spray freeze-drying, liquid nitrogen. The liquid feed is atomized into a spray of droplets. The droplets are then dried by contact with the gas in a drying chamber or with the liquid nitrogen.

Fluid Bed Drying

In a further embodiment, drying is achieved by fluid bed drying the viral particles admixed with the preservation mixture of the invention. This technique is well known to those skilled in the art and typically involves passing a gas (e.g. air) through a product layer under controlled velocity conditions to create a fluidized state. The technique can involve the stages of drying, cooling, agglomeration, granulation and coating of particulate product materials. Heat may be supplied by the fluidization gas and/or by other heating surfaces (e.g. panels or tubes) immersed in the fluidized layer. Cooling can be achieved using a cold gas and/or cooling surfaces immersed in the fluidized layer. The steps of agglomeration and granulation are well known to those skilled in the art and can be performed in various ways depending on the product properties to be achieved. Coating of particulate products such as powders, granules or tablets can be achieved by spraying a liquid on the fluidized particles under controlled conditions.

Dried Composition

A composition having a low residual moisture content can be obtained. A level of residual moisture content is achieved which offers long term preservation at greater than refrigeration temperatures e.g. within the range from 4° C. to 56° C. or more, or lower than refrigeration temperatures e.g. within the range from 0 to −70° C. or below. The dried composition may thus have residual moisture content of 10% or less, 5% or less, 2% or less or 1% or less by weight. Preferably the residual moisture content is 0.5% or more 1% or more. Typically a dried composition has residual moisture content of from 0.5 to 10% by weight and preferably from 1 to 5% by weight.

The composition can be obtained in a dry powder form. A cake resulting from e.g. freeze-drying can be milled into powder form. A solid composition according to the invention thus may take the form of free-flowing particles. The solid composition is typically provided as a powder in a sealed vial, ampoule or syringe. If for inhalation, the powder can be provided in a dry powder inhaler. The solid matrix can alternatively be provided as a patch. A powder may be compressed into tablet form.

The composition may typically consist, or consist essentially, of viral particles, a compound of formula (I) or a physiologically acceptable salt or ester thereof and/or a compound of formula (II) or a physiologically acceptable salt or ester thereof, and optionally one or more sugars.

Drying onto a Solid Support

However, in a further embodiment of the method of the invention, the admixture comprising viral particles is dried onto a solid support. The solid support may comprise a bead, test tube, matrix, plastic support, microtitre dish, microchip (for example, silicon, silicon-glass or gold chip), or membrane. In another embodiment, there is provided a solid support onto which a viral particle preserved according to the methods of the present invention is dried or attached.

Measuring Viral Particle Preservation

Preservation in relation to viral particles refers to resistance of the viral particle to physical or chemical degradation and/or loss of biological activity such as nucleic acid or protein degradation, loss of transfection efficiency, loss of ability to stimulate a cellular or humoral immune response, loss of viral infectivity, loss of immunogenicity, loss of virus titre, loss of host cell response or loss of vaccine potency, under exposure to conditions of desiccation, freezing, temperatures below 0° C. or below −25° C., freeze-drying, room temperature, temperatures above 0° C., above 25° C. or above 30° C. Preferably, preservation according to the present invention comprises cryoprotection (protection against freeze damage), lyoprotection (protection during freeze-drying) and/or thermoprotection (protection against temperatures higher or lower than 4° C.).

Methods of assaying for viral activity such as infectivity and/or immunogenicity are well known to those skilled in the art and include but are not limited to growth of a virus in a cell culture, detection of virus-specific antibody in blood, ability to elicit T and/or B cell responses, detection of viral antigens, detection of virus encoded DNA or RNA, or observation of virus particles using a microscope.

Further, the presence of a virus gives rise to morphological changes in the host cell, which can be measured to give an indication of viral activity. Detectable changes such as these in the host cell due to viral infection are known as cytopathic effect. Cytopathic effects may consist of cell rounding, disorientation, swelling or shrinking, death and detachment from the surface. Many viruses induce apoptosis (programmed cell death) in infected cells, measurable by techniques such as the TUNEL (Terminal uridine deoxy-nucleotidyl transferase dUTP nick end labelling) assay and other techniques well known to those skilled in the art.

Viruses may also affect the regulation of expression of the host cell genes and these genes can be analysed to give an indication of whether viral activity is present or not. Such techniques may involve the addition of reagents to the cell culture to complete an enzymatic or chemical reaction with a viral expression product. Furthermore, the viral genome may be modified in order to enhance detection of viral infectivity. For example, the viral genome may be genetically modified to express a marker that can be readily detected by phase contrast microscopy, fluorescence microscopy or by radioimaging. The marker may be an expressed fluorescent protein such as GFP (Green Fluorescent Protein) or an expressed enzyme that may be involved in a colourimetric or radiolabelling reaction. The marker could also be a gene product that interrupts or inhibits a particular function of the cells being tested.

An assay for plaque-forming units can be used to measure viral infectivity and to indicate viral titre. In this assay, suitable host cells are grown on a flat surface until they form a monolayer of cells covering a plastic bottle or dish. The selection of a particular host cell will depend on the type of virus. Examples of suitable host cells include but are not limited to CHO, BHK, MDCK, 10T1/2, WEHI cells, COS, BSC 1, BSC 40, BMT 10, VERO, WI38, MRCS, A549, HT1080, 293, B-50, 3T3, NIH3T3, HepG2, Saos-2, Huh7, HEK293 and HeLa cells. The monolayer of host cells is then infected with the viral particles. The liquid medium is replaced with a semi-solid one so that any virus particles produced, as the result of an infection cannot move far from the site of their production. A plaque is produced when a virus particle infects a cell, replicates, and then kills that cell. A plaque refers to an area of cells in the monolayer which display a cytopathic effect, e.g. appearing round and darker than other cells under the microscope, or as white spots when visualized by eye; the plaque center may lack cells due to virus-induced lysis. The newly replicated virus infects surrounding cells and they too are killed. This process may be repeated several times. The cells are then stained with a dye such as methylene blue, which stains only living cells. The dead cells in the plaque do not stain and appear as unstained areas on a coloured background.

Each plaque is the result of infection of one cell by one virus followed by replication and spreading of that virus. However, viruses that do not kill cells may not produce plaques. A plaque refers to an area of cells in a monolayer which display a cytopathic effect, e.g. appearing round and darker than other cells under the microscope, or as white spots when visualized by eye; the plaque center may lack cells due to virus-induced lysis. An indication of viral titre is given by measuring "plaque forming units" (PFU). Levels of viral infectivity can be measured in a sample of biological material preserved according to the present invention and compared to control samples such as freshly harvested virus or samples subjected to desiccation and/or thermal variation without addition of the preservation mixture of the present invention.

Some types of viral particles of the invention, such as viral proteins, VLPs, or some inactivated viruses do not have the ability to form plaques in the plaque assay. In this case, preservation can be measured by other methods such as methods for determining immunogenicity which are well known to those skilled in the art. For example, in vivo and in vitro assays for measuring antibody or cell-mediated host immune responses are known in the art and suitable for use in the present invention. For example, an antibody based immune response may be measured by comparing the amount, avidity and isotype distribution of serum antibodies in an animal model, before and after immunization using the preserved viral particle of the invention.

Uses of the Preserved Viral Particles of the Invention

Vaccines

The preserved viral particles of the present invention may find use as a vaccine. For example, preserved viral particles such as whole killed virus, live attenuated virus, chemically inactivated virus, VLPs or live viral vectors are suitable for use as a vaccine. As a vaccine the preserved viral particles of the invention may be used as antigens or to encode antigens such as viral proteins for the treatment or prevention of a number of conditions including but not limited to viral infection, sequelae of viral infection including but not limited to viral-induced toxicity, cancer and allergies. Such antigens contain one or more epitopes that will stimulate a host's immune system to generate a humoral and/or cellular antigen-specific response.

The preserved vaccine of the invention may be used to prevent or treat infection by viruses such as human papilloma viruses (HPV), HIV, HSV2/HSV1, influenza virus (types A, B and C), para influenza virus, polio virus, RSV virus, rhinoviruses, rotaviruses, hepaptitis A virus, norwalk virus, enteroviruses, astroviruses, measles virus, mumps virus, varicella-zoster virus, cytomegalovirus, epstein-barr virus, adenoviruses, rubella virus, human T-cell lymphoma type I virus (HTLV-I), hepatitis B virus (HBV), hepatitis C virus (HCV), hepatitis D virus, poxvirus and vaccinia virus. The vaccine may further be used to provide a suitable immune response against numerous veterinary diseases, such as foot and mouth disease (including serotypes O, A, C, SAT-1, SAT-2, SAT-3 and Asia-1), coronavirus, bluetongue, feline leukaemia virus, avian influenza, hendra and nipah virus, pestivirus, canine parvovirus and bovine viral diarrhoea virus. In one embodiment, the vaccine is a subunit, conjugate or multivalent vaccine. For example, the preserved vaccine of the invention may be used to treat infection by two or more different types of virus such as measles, mumps and rubella (e.g. MMR vaccine).

The vaccine compositions of the present invention comprise viral particles admixed with the preservation mixture of the invention containing one or more sugars and a sulfoxide, sulfone, sulfonium, thetin or betaine compound. The vaccine composition may further comprise appropriate buffers and additives such as antibiotics, adjuvants or other molecules that enhance presentation of vaccine antigens to specific cells of the immune system.

A variety of adjuvants well known in the art can be used in order to increase potency of the vaccine and/or modulate humoral and cellular immune responses. Suitable adjuvants include, but are not limited to, mineral salts (e.g., aluminium hydroxide ("alum"), aluminium phosphate, calcium phosphate), particulate adjuvants (e.g., virosomes, ISCOMS (structured complex of saponins and lipids)), microbial derivatives (e.g., MPL (monophosphoryl lipid A), CpG motifs, modified toxins including TLR adjuvants such as flagellin), plant derivatives (e.g., saponins (QS-21)) and endogenous immunostimulatory adjuvants (e.g., cytokines and any other substances that act as immunostimulating agents to enhance the effectiveness of the vaccine).

The vaccine composition of the present invention can be in a freeze-dried (lyophilised) form in order to provide for appropriate storage and maximize the shelf-life of the preparation. This will allow for stock piling of vaccine for prolonged periods of time and help maintain immunogenicity, potency and efficacy. The preservation mixture of the present invention is particularly suited to preserve viral substances against desiccation and thermal stresses encountered during freeze-drying/lyophilisation protocols. Therefore, the preservation mixture is suitable for adding to the virus or viral particle soon after harvesting and before subjection of the sample to the freeze-drying procedure.

To measure the preservation of a vaccine prepared in accordance with the present invention, the potency of the vaccine can be measured using techniques well known to those skilled in the art. For example, the generation of a cellular or humoral immune response can be tested in an appropriate animal model by monitoring the generation of antibodies or immune cell responses to the vaccine. The ability of vaccine samples prepared in accordance with the method of the present invention to trigger an immune response may be compared with vaccines not subjected to the same preservation technique.

Viral Vectors

A virus or viral vector preserved according to the method of the present invention can be used to transfer a heterologous gene or other nucleic acid sequence to target cells. Suitably, the heterologous sequence (i.e. transgene) encodes a protein or gene product which is capable of being expressed in the target cell. Suitable transgenes include desirable reporter genes, therapeutic genes and genes encoding immunogenic polypeptides (for use as vaccines). Gene therapy, an approach for treatment or prevention of diseases associated with defective gene expression, involves the insertion of a therapeutic gene into cells, followed by expression and production of the required proteins. This approach enables replacement of damaged genes or inhibition of expression of undesired genes. In particular, the preserved virus or viral vector may be used in gene therapy to transfer a therapeutic transgene or gene encoding immunogenic polypeptides to a patient.

In a preferred embodiment, the preserved viral particle is a live viral vector. By "live viral vector" is meant a live viral vector that is non-pathogenic or of low pathogenicity for the target species and in which has been inserted one or more genes encoding antigens that stimulate an immune response protective against other viruses or microorganisms, a reporter gene or a therapeutic protein. In particular, nucleic acid is introduced into the viral vector in such a way that it is still able to replicate thereby expressing a polypeptide encoded by the inserted nucleic acid sequence and in the case of a vaccine, eliciting an immune response in the infected host animal. In one embodiment, the live viral vector is an attenuated live viral vector i.e. is modified to be less virulent (disease-causing) than wildtype virus.

The basis of using recombinant viruses as potential vaccines involves the incorporation of specific genes from a pathogenic organism into the genome of a nonpathogenic or attenuated virus. The recombinant virus can then infect specific eukaryotic cells either in vivo or in vitro, and cause them to express the recombinant protein.

Live viral vector vaccines derived by the insertion of genes encoding sequences from disease organisms may be preferred over live attenuated vaccines, inactivated vaccines, subunit or DNA approaches. One of the most important safety to features of live viral vectors is that the recipients may be immunized against specific antigens from pathogenic organisms without exposure to the disease agent itself. Safety is further regulated by the selection of a viral vector that is either attenuated for the host or unable to replicate in the host although still able to express the heterologous antigen of interest. A vaccine strain that has a history of safety in the target species offers an additional safety feature. Several systems have been developed in which the vector is deleted of essential genes and preparation of the vaccine is carried out in cell systems that provide the missing function.

A variety of vectors such as retroviral, lentiviral, herpes virus, poxvirus, adenoviral and adeno-associated viral vectors can be used for the delivery of heterologous genes to target cells. The heterologous gene of interest may be inserted into the viral vector. The viral vectors of the invention may comprise for example a virus vector provided with an origin of replication, optionally a promoter for the expression of the heterologous gene and optionally a regulator of the promoter. For example, adenoviruses useful in the practice of the present invention can have deletions in the E1 and/or E3 and for E4 region, or can otherwise be maximized for receiving heterologous DNA.

The viral vector may comprise a constitutive promoter such as a cytomegalovirus (CMV) promoter, SV40 large T antigen promoter, mouse mammary tumour virus LTR promoter, adenovirus major late promoter (MLP), the mouse mammary tumour virus LTR promoter, the SV40 early promoter, adenovirus promoters such as the adenovirus major late promoter (Ad MLP), HSV promoters (such as the HSV IE promoters), HPV promoters such as the HPV upstream regulatory region (URR) or rous sarcoma virus promoter together with other viral nucleic acid sequences operably linked to the heterologous gene of interest. Tissue-specific or inducible promoters can also be used to control expression of the heterologous gene of interest. Promoters may also be selected to be compatible with the host cell for which expression is designed.

The viral vector may also comprise other transcriptional modulator elements such as enhancers. Enhancers are broadly defined as a cis-acting agent, which when operably linked to a promoter/gene sequence, will increase transcription of that gene sequence. Enhancers can function from positions that are much further away from a sequence of interest than other expression control elements (e.g. promoters) and may operate when positioned in either orientation relative to the sequence of interest. Enhancers have been identified from a number of viral sources, including polyoma virus, BK virus, cytomegalovirus (CMV), adenovirus, simian virus 40 (SV40), Moloney sarcoma virus, bovine papilloma virus and Rous sarcoma virus. Examples of suitable enhancers include the SV40 early gene enhancer, the enhancer/promoter derived from the long terminal repeat (LTR) of the Rous Sarcoma Virus, and elements derived from human or murine CMV, for example, elements included in the CMV intron A sequence.

The viral vector containing a heterologous gene of interest may then be preserved according to the method of the invention before storage, subjecting to further preservation techniques such as lyophilisation, or administration to a patient or host cell.

Nucleic acids encoding for polypeptides known to display antiviral activity, immunomodulatory molecules such as cytokines (e.g. TNF-alpha, interleukins such as IL-6, and IL-2, interferons, colony stimulating factors such as GM-CSF), adjuvants and co-stimulatory and accessory molecules may be included in the viral vector of the invention. Alternatively, such polypeptides may be provided separately, for example in the preservation mixture of the invention or may be administrated simultaneously, sequentially or separately with viral vectors of the invention.

Preferably, the preserved viral vector of the invention may be introduced into suitable host cells using a variety of viral techniques that are known in the art, such as for example infection with recombinant viral vectors such as retroviruses, herpes simplex virus and adenoviruses. Preferably, administration of the preserved viral vector of the invention containing a gene of interest is mediated by viral infection of a target cell.

A number of viral based systems have been developed for transfecting mammalian cells.

For example, a selected recombinant nucleic acid molecule can be inserted into a vector and packaged as retroviral particles using techniques known in the art. The recombinant virus can then be isolated and delivered to cells of the subject either in vivo or ex vivo. Retroviral vectors may be based upon the Moloney murine leukaemia virus (Mo-MLV). In a retroviral vector, one or more of the viral genes (gag, pol & env) are generally replaced with the gene of interest.

A number of adenovirus vectors are known. Adenovirus subgroup C serotypes 2 and 5 are commonly used as vectors. The wild type adenovirus genome is approximately 35 kb of which up to 30 kb can be replaced with foreign DNA.

There are four early transcriptional units (E1, E2, E3 & E4), which have regulatory functions, and a late transcript, which codes for structural proteins. Adenovirus vectors may have the E1 and/or E3 gene inactivated. The missing gene(s) may then be supplied in trans either by a helper virus, plasmid or integrated into a helper cell genome. Adenovirus vectors may use an E2a temperature sensitive mutant or an E4 deletion. Minimal adenovirus vectors may contain only the inverted terminal repeats (ITRs) & a packaging sequence around the transgene, all the necessary viral genes being provided in trans by a helper virus. Suitable adenoviral vectors thus include Ad5 vectors and simian adenovirus vectors.

Viral vectors may also be derived from the pox family of viruses, including vaccinia viruses and avian poxvirus such as fowlpox vaccines. For example, modified vaccinia virus Ankara (MVA) is a strain of vaccinia virus which does not replicate in most cell types, including normal human tissues. A recombinant MVA vector may therefore be used to deliver the polypeptide of the invention.

Addition types of virus such as adeno-associated virus (AAV) and herpes simplex virus (HSV) may also be used to develop suitable vector systems Excipient In the present invention, an excipient for the preservation of viral particles is also provided. The excipient comprises (a) optionally one or more sugars such as sucrose, raffinose, stachyose, trehalose, or a sugar alcohol or any combination thereof; and (b) a compound of formula (I) or a physiologically acceptable salt or ester thereof and/or a compound of formula (II) or a physiologically acceptable salt or ester thereof. Preferably one or more sugars is present. Preferably the excipient consists, or consists essentially of these components.

By "excipient" is meant an inactive substance used as a carrier for the viral particles of the invention (for example when the viral particles are used as a vaccine). Typically, the viral particles (e.g. for use as a vaccine) are dissolved into or mixed with the excipient, which acts as a preservative of the viral particle and/or in some contexts aids administration and absorption into the body. As well as the preservation mixture of the present invention, an excipient may also comprise other preservatives such as antioxidants, lubricants and binders well known in the art, as long as those ingredients do not significantly reduce the effectiveness of the preservation mixture of the present invention.

Assaying on a Solid Support

Preserved viral particles stored on a solid support may be used for diagnostic purposes or to monitor a vaccination regime. For example, a patient sample such as bodily fluid (blood, urine, saliva, phlegm, gastric juices etc) may be preserved according to the methods described herein by drying an admixture comprising the patient sample and preservation mixture of the present invention onto a solid support. Preserved patient samples may then be tested for the presence of viral antigens/epitopes in the sample using anti-viral antibodies (for example using ELISA). Alternatively, viral particles of interest may be preserved according to the methods described herein by drying an admixture comprising the viral particles and preservation mixture of the present invention onto a solid support. Patient samples may be tested for the presence of anti-viral antibodies by contacting the patient sample with a solid support onto which the viral particles of interest are attached. The formation of antigen-antibody complexes can elicit a measurable signal. The presence and/or amount of viral particle antigen-antibody complexes in a sample may be used to indicate the presence of a viral infection or progress of a vaccination regime in a patient.

Administration

Preserved vaccines or viral particles according to the present invention may be administered, in some instances after reconstitution of a dried or freeze-dried product, to a subject in vivo using a variety of known routes and techniques. For example, the preserved vaccines can be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. Preserved vaccines may be administered topically to skin or mucosal tissue, such as nasally, intratrachealy, intestinal, sublingually, rectally or vaginally, or provided as a finely divided spray suitable for respiratory or pulmonary administration.

In one embodiment, the method of the invention further comprises the step of processing the mixture into a formulation suitable for administration as a liquid injection. Preferably, the method further comprises the step of processing the mixture into a formulation suitable for administration via ingestion or via the pulmonary route.

The preserved product is administered to a subject in an amount that is compatible with the dosage formulation and that will be prophylactically and/or therapeutically effective. The administration of the preserved product or vaccine of the invention may be for either "prophylactic" or "therapeutic" purpose. As used herein, the term "therapeutic" or "treatment" includes any of the following: the prevention of infection or reinfection; the reduction or elimination of symptoms; and the reduction or complete elimination of a pathogen. Treatment may be effected prophylactically (prior to infection) or therapeutically (following infection).

The compound of formula (I) or physiologically acceptable salt or ester thereof and/or compound of formula (II) or physiologically acceptable salt or ester thereof and, optionally, one or more sugars, typically acts as a resuspension agent for a dried or freeze-dried product comprising viral particles, preferably a product of the invention, for example when it is converted into liquid form (aqueous solution) prior to administration to a patient.

The following Examples illustrate the invention. The following materials, equipment and techniques were employed unless stated otherwise in the Examples:

Materials

HEK-293 cells (ECACC 85120602)
Dimethylglycine DMG (Sigma D1156, Lot 077K1856)
Dimethylsulfone (MSM) (Sigma M81705, Lot 0001452516)
Sucrose (Sigma 16104, Lot 70040)
Raffinose (Sigma R0250, Lot 039K0016)
PBS (Sigma D8662, Lot 118K2339)
Water (Sigma W3500, Lots 8M0411 and RNBB1139)
Hydranal Methanol (Fluka 37817, Lot 8331D)
Hydranal Composite (Fluka 34805, Lot 8287A)
5 ml glass vials (Adelphi Tubes VCD005)
14 mm freeze drying stoppers (Adelphi Tubes FDIA14WG/B)
14 mm caps (Adelphi Tubes CWPP14)
Adenovirus GFP (Vector Biolabs cat. 1060)
Measles virus strains 3A and 1A (a kind gift provided by P. Christian at NIBSC)
Dulbecco's Modified Eagles Medium (DMEM) (Sigma D5796, Lot RNBB1139)
Foetal Bovine Serum (FBS) (Sigma F7524, Lot 109K3395)
Penicillin Streptomycin (PS) (Sigma P4458, Lot 0409M00393)
Saline Sodium Citrate (SSC) (Sigma S6639, Lot 020M8404)
BHK-21 cell line (ECCAC CB2857)
HEK 293 (ECACC 85120602)
MVA (ATCC-VR-1508)
2 ml glass vials (Adelphi Tubes VCDIN2R)
13 mm freeze drying stoppers (Adelphi Tubes FDW13)
Crimps (Adelphi Tubes COTW13)

Equipment

Advantage Freeze Dryer (VirTis)
HERASAFE™ class II cabinet (Thermo Fisher)
VirTis Advantage freeze dryer (Biopharma Process Systems)
Binder $CO_2$ Incubator (Binder)
Binder APT line TM MK thermocycling test chamber (Binder)
Thermo Scientific MAXQ™ 4450 Incubator (Thermofisher)
.
KERN EW220-3NM balance (VWR)
Elcold −45° C. freezer (VWR)
Form a 900 series −80° C. freezer (Thermofisher)
Karl Fisher Volumetric Titrator (Mettler Toldeo)
DMIL LED Inverted Microscope (Leica, EQP#062)
ATL-84-1 Atlion Balance (Acculab, EQP#088)
IP250 37° C. Incubator (LTE, EQP#016)

Freeze Drying Protocol

Samples were freeze dried by the VirTis Advantage freeze dryer, using the pre-programmed protocol lasting for approximately 3 days. Samples were frozen at −40° C. for 1 hour before a vacuum was applied, initially at 200 milliTorre with a Thermo SAVANT™ VLP pump (Thermofisher, UK). Shelf temperature and vacuum were adjusted throughout the process and the condenser was maintained at −80° C. Step 8 was extended until the samples were stoppered before releasing the vacuum. The drying cycle used is shown below:

| Step | Shelf temp (° C.) | Time (mins) | Ramp/Hold | Vacuum (milliTorre) |
|---|---|---|---|---|
| 1 | −45 | 15 | H | — |
| 2 | −32 | 600 | R | 200 |
| 3 | −20 | 120 | R | 200 |
| 4 | −10 | 120 | R | 200 |
| 5 | 0 | 120 | R | 200 |
| 6 | 10 | 120 | R | 200 |
| 7 | 20 | 120 | R | 200 |
| 8 | 20 | 1250 | H | 400 |

Figure 2A:
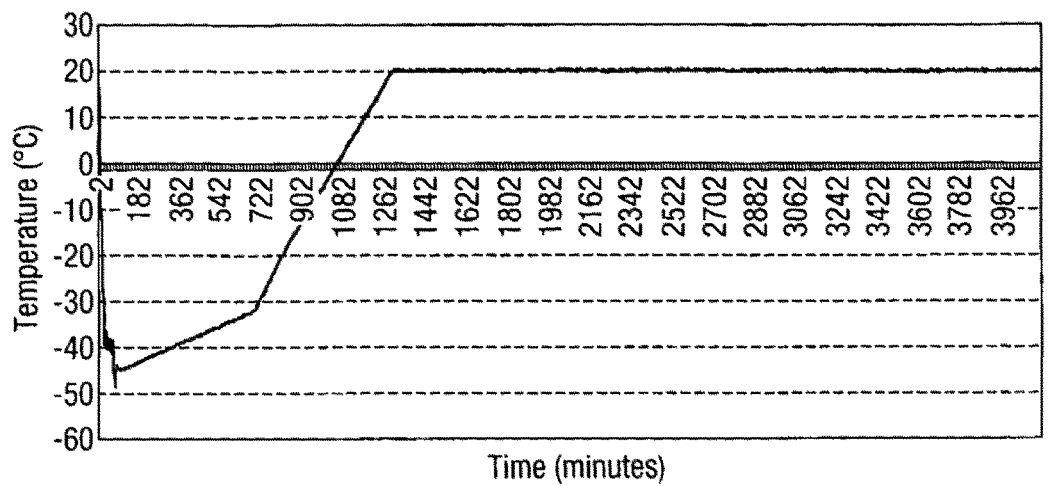
FIG. 2A shows the temperature set for the shelf temperature of the VirTis Advantage freeze dryer used in various of the Examples.
Figure 2B:
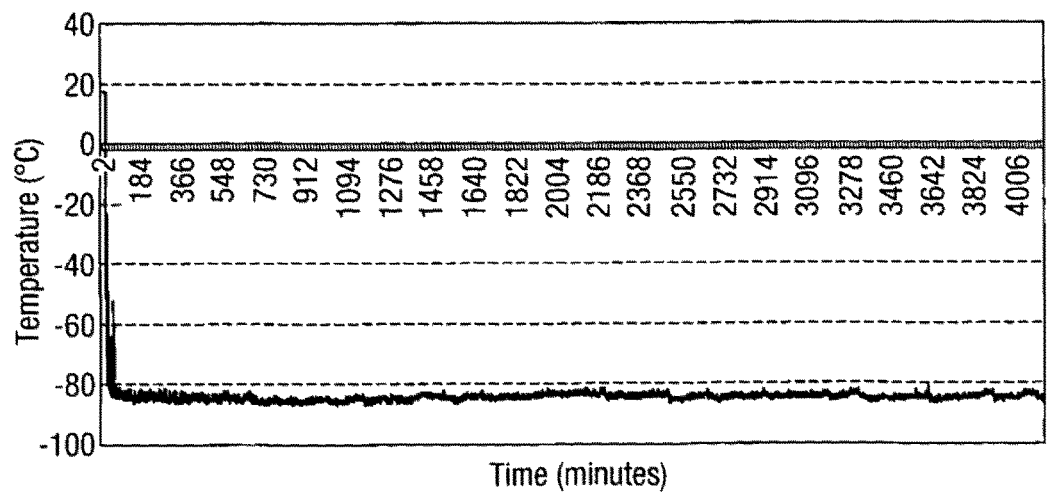
FIG. 2B shows the condenser temperature of the VirTis Advantage freeze dryer used in various of the Examples.

In the primary drying phase the shelf temperature is raised to −32° C. from −45° C. The secondary drying phase included a ramp to 20° C. until the drying was completed. The condenser temperature was set to stay at a constant −80° C. Probes recorded shelf temperatures and condenser temperatures (see FIGS. 2A and 2B).

Statistical Analysis

A one way ANOVA test followed by a turkey pair wise comparison was performed to analyse significance between different excipients using PRISM Graphpad software version 4.00. The p value summaries are *=p<0.10; =p<0.05; *=p<0.005.

In some Examples the following values were calculated:
$R^2$=coefficient of determination. A measure of goodness of fit. $R^2$<0.5=low model significance.

$Q^2$=estimate of prediction precision. A measure of goodness of prediction. $Q^2$ should be >0.1 for a significant model. $Q^2$ should be >0.5 for a good model. $R^2$-$Q^2$<0.2 to 0.3

Model validity (MV)="a test of diverse model problems". Model validity<0.25=indicator of statistically significant model problems e.g. outliers, incorrect model/transformation.

Reproducibility (Rep)=measure of variation between replicates compared to over all variability. Reproducibility>0.5 implies significance.

Example 1

Freeze Drying

Each type of excipient (see Table 1 below) was made up as a stock and 250 µl added to appropriately labelled 5 ml glass vials. 50 µl of adenovirus was then added to each vial. After vortexing, vials were loaded onto the VirTis Advantage freeze drier and freeze dried according to the protocol given in the general experimental techniques section above.

TABLE 1

| Final Concentrations of excipient mixes | | |
|---|---|---|
| PBS | Suc (1M) Raf (100 mM) | Suc (1M) Raf (100 mM), Dimethyl sulfone (1M) |

Thermal Challenge

Following freeze drying, samples were incubated in a Binder APT line TM MK temperature test chamber. Samples were cycled through a temperature of 37° C. for 12 hours, a one hour ramp to −20° C., 10 hours at −20° C. followed by a one hour ramp to 37° C. Each cycle amounted to 24 hours and was repeated for a 2 week period before carrying out an adenovirus assay as described below.

Adenovirus Assay (GFP)

96 flat bottomed cell culture dishes (Jencons, UK) were seeded with HEK 293 cells (ECACC 85120602) at $10^5$ cells per ml (100 µl per well) and maintained at 37° C. with 5% $CO_2$. After achieving 90% confluence, vials containing the adenovirus plus excipient were reconstituted in 300 µl PBS. A 1 in 10 dilution step was then taken by taking 20 µl from the reconstituted vial and adding to 180 µl of Dulbecco's Modified Eagle Medium (DMEM). A further 1 in 100 dilution (of the original sample) was performed by taking 20 µl of the 1 in 10 dilution and adding it to 180 µl of DMEM. 100 µl of each of the resultant dilution (1 in 10 and 1 in 100) was then added to wells of the plate containing HEK 293 cells. Additionally, a further sample of adenovirus, from the same source and with the same titre (on storage at −80° C.) used in the excipient treatments, was thawed and used to produce a 1 in 10 dilution series (in DMEM). Dilutions ranging from 1 in 10 to 1 in $10^6$ were also added to individual wells containing HEK 293s. At 48 hours post inoculation, the number of GFP (Green Fluorescent Protein) cells per well were counted using fluorescent microscopy, and this was subsequently converted to pfu/ml of the treated samples taking into account the volume applied and dilution of the inoculum.

Results and Discussion

This experiment was designed to assess the effect of cooling and heating on viral recovery in the presence of excipients during storage. The results demonstrate poor recovery in excipients containing sugars only or PBS (FIG. 1). In excipients containing sugars plus dimethylsulfone, recovery was significantly higher.

Additionally, excipients containing dimethylsulfone showed little deterioration following heat and freeze challenge compared to control samples. The results indicate that thermoprotection during the FD process is essential as inadequate excipients such as sugars alone or PBS fail to produce any significant virus titre following FD. However when excipients containing dimethyl sulfone are used in conjunction with sugars, virus titre remains close to that of the original titre even during freeze thaw cycles.

Example 2

Each type of excipient plus virus (see Table 2) was made up as a stock in PBS and 250 µl added to appropriately labelled 5 ml glass vials. All vials were prepared in triplicate. 50 µl of adenovirus was added to each vial. After vortexing, rubber bungs were partially inserted and vials were loaded onto the VirTis advantage and freeze-dried (FD) according to the freeze drying protocol given in the general experimental techniques section above. Following freeze drying, samples were assessed for virus titre using the adenovirus assay described in Example 1.

TABLE 2

| Composition of excipients | Final Concentration of excipients |
|---|---|
| Suc/Raf + MSM | 1M Suc 100 mM Raf 0.35M MSM |
| Suc/Raf + MSM | 1M Suc 100 mM Raf 0.035M MSM |
| Suc/Raf + MSM | 1M Suc 100 mM Raf 0.0035M MSM |
| Suc/Raf + MSM | 1M Suc 100 mM Raf 0.35 mM MSM |
| Suc/Raf + MSM | 1M Suc 100 mM Raf 0.035 mM MSM |
| MSM | 0.35M MSM |
| MSM | 0.035M MSM |
| MSM | 0.0035M MSM |
| MSM | 0.35 mM MSM |
| Suc/Raf | 1M Suc 100 mM Raf |
| PBS | PBS |

The results are shown in FIG. 3. PBS, Sugars only and MSM only excipients gave poor recovery. Recovery of virus significantly increased when the excipient included MSM as well as sugars. The results showed a synergistic effect between MSM and sugars, whereas MSM used in isolation provided to be a poor stabilising excipient.

Residual Moisture Protocol

Some vials were taken for residual moisture measurement (see Table 3 below).

Assessment of residual moisture was carried out using a volumetric Karl Fisher titrator. The titrator (Mettler Toledo) works on the principle that one mole of $I_2$ is consumed for each mole of $H_2O$. The titrator was validated using a 10 mg/ml water standard (Sigma, UK).

Titration was carried out by weighing vials containing the dried excipient mixture using a balance (Kern, Germany). 1 ml of liquid (hydranal methanol rapid and hydranol methanol composite, Fluka) from the chamber is transferred from the titration chamber to the glass vial using a 5 ml syringe and needle. Once the excipient has dissolved the liquid is then taken back up into the syringe and the liquid injected into the titration chamber. The vial was reweighed and the difference in weight (the weight of the excipient) was inputted into the titrator. The titrator then calculated the residual moisture.

Measurements indicate that the presence of MSM may assist in the drying of the cake during secondary drying.

TABLE 3

Residual moisture as a percentage of freeze dried excipient mixture

|  | Suc (1M) Raf (100 mM) | Suc (1M) Raf (100 mM), MSM (0.35M) |
|---|---|---|
| Mean percentage moisture | 6.5% | 4.6% |

Example 3

A mixture of excipient plus virus was prepared and processed as described in Example 2. The excipient contained TMG and optionally sugars. The final concentration of each component in the excipient before drying is shown in Table 4 below. All vials were prepared in triplicate.

TABLE 4

|  | TMG (M) | Sucrose (M) | Raffinose (mM) | Virus |
|---|---|---|---|---|
| Test | 0.7 | 1 | 100 | Y |
|  | 0.2 | 1 | 100 | Y |
|  | 0.07 | 1 | 100 | Y |
| Excipient alone | 0.7 | 0 | 0 | Y |
|  | 0.2 | 0 | 0 | Y |
|  | 0.07 | 0 | 0 | Y |
| Assay controls | 0.7 | 1 | 100 | N |
|  | 0.7 | 0 | 0 | N |

Figure 4:
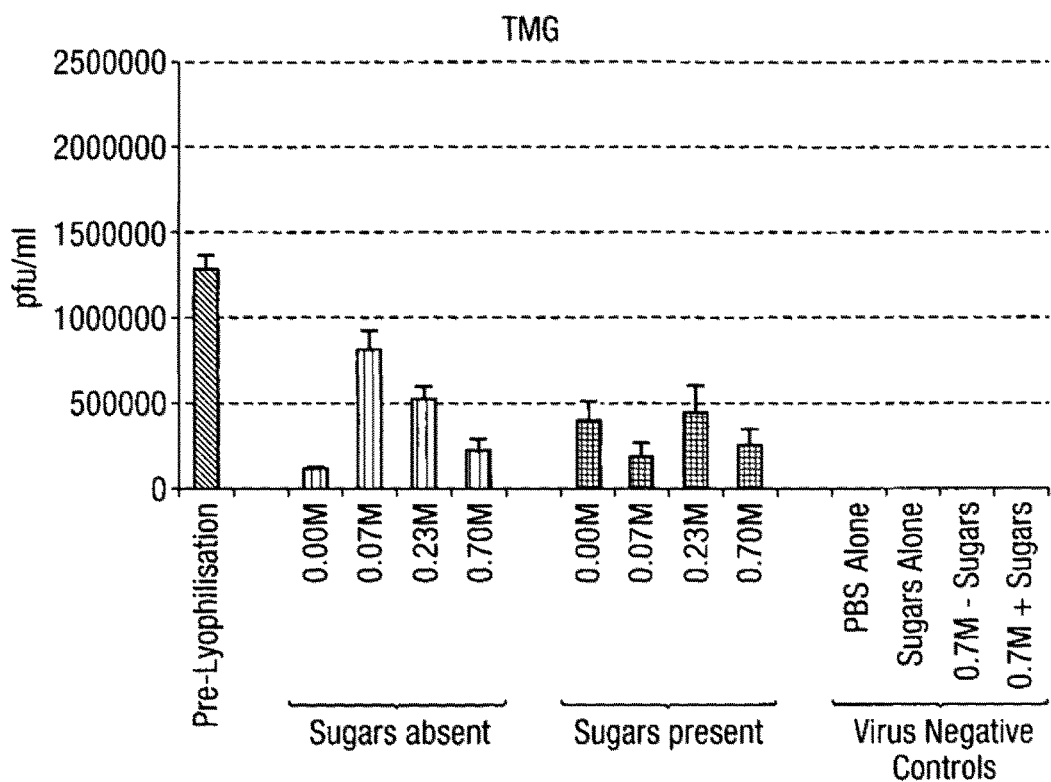
FIG. 4 shows the results obtained in Example 3 of adenovirus infectivity tested immediately after thawing as well as those of samples lyophilised after formulation with TMG (trimethylglycine) with or without sugars. Adenoviral activity stated as pfu/ml as assessed by counting cells positive for GFP expression. Error bars shown are the standard error of the mean (n=3).

The results of using TMG (Trimethylglycine) in the excipient are shown in FIG. 4. TMG appears to enhance recovery of adenoviral infectivity from lyophilised samples. However, the lowest concentration (0.07M) offers the greatest protection and increasing TMG concentration above this concentration reduces the protection offered. The 0.07M TMG treatment offered greater protection than sugars alone.

Example 4

Example 4 describes experimentation to elucidate the interaction between S-methyl-L-methionine (SMM), sucrose and raffinose as excipients in a freeze dried formulation of adenovirus.

Preparation and Lyophilisation of Virus

Recombinant adenovirus (Vector Biolabs) expressing enhanced GFP under a CMV promoter, and with a titre (pre-freeze) of $2\times10^6$ pfu/ml, was removed from storage at −80° C. and allowed to thaw. 50 µl aliquots of the virus were diluted to 300 µl in PBS containing a variable concentration of each of the excipients. A full list of excipient formulations tested can be seen in Table 5.

TABLE 5

Summary of excipient treatments, each treatment was made in triplicate

| Sucrose (M) | Raffinose (mM) | SMM (M) | Thermal Challenge |
|---|---|---|---|
| 0.0 | 0 | 0.000 | 37 |
| 0.0 | 0 | 0.007 | 37 |
| 0.0 | 0 | 0.023 | 37 |
| 0.0 | 0 | 0.070 | 37 |
| 0.0 | 0 | 0.230 | 37 |
| 0.0 | 0 | 0.700 | 37 |
| 0.0 | 0 | 1.000 | 37 |
| 0.1 | 10 | 0.000 | 37 |
| 0.1 | 10 | 0.007 | 37 |
| 0.1 | 10 | 0.023 | 37 |
| 0.1 | 10 | 0.070 | 37 |
| 0.1 | 10 | 0.230 | 37 |
| 0.1 | 10 | 0.700 | 37 |
| 0.1 | 10 | 1.000 | 37 |
| 1.0 | 100 | 0.000 | 37 |
| 1.0 | 100 | 0.007 | 37 |
| 1.0 | 100 | 0.023 | 37 |
| 1.0 | 100 | 0.070 | 37 |
| 1.0 | 100 | 0.230 | 37 |
| 1.0 | 100 | 0.700 | 37 |
| 1.0 | 100 | 1.000 | 37 |
| 0.0 | 0 | 0.000 | 4 |
| 0.0 | 0 | 0.007 | 4 |
| 0.0 | 0 | 0.023 | 4 |
| 0.0 | 0 | 0.070 | 4 |
| 0.0 | 0 | 0.230 | 4 |
| 0.0 | 0 | 0.700 | 4 |
| 0.0 | 0 | 1.000 | 4 |
| 0.1 | 10 | 0.000 | 4 |
| 0.1 | 10 | 0.007 | 4 |
| 0.1 | 10 | 0.023 | 4 |
| 0.1 | 10 | 0.070 | 4 |
| 0.1 | 10 | 0.230 | 4 |
| 0.1 | 10 | 0.700 | 4 |
| 0.1 | 10 | 1.000 | 4 |
| 1.0 | 100 | 0.000 | 4 |
| 1.0 | 100 | 0.007 | 4 |
| 1.0 | 100 | 0.023 | 4 |
| 1.0 | 100 | 0.070 | 4 |
| 1.0 | 100 | 0.230 | 4 |
| 1.0 | 100 | 0.700 | 4 |
| 1.0 | 100 | 1.000 | 4 |

Figure 5:
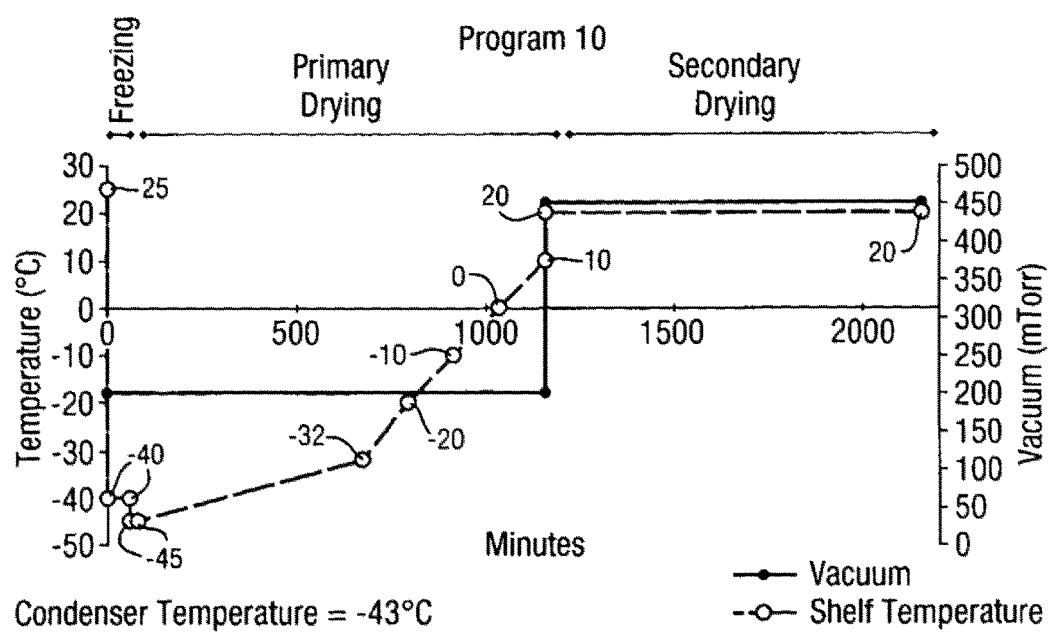
FIG. 5 demonstrates the lyophilisation conditions used in Example 4.

Each treatment was made up in 6 replicate vials. These samples were prepared in 5 ml glass vials, rubber bungs were partially inserted, and after vortexing were loaded onto the VirTis advantage and lyophilized under the conditions shown in FIG. 5.

Thermal Challenge of Lyophilised Adenovirus

After lyophilisation samples were immediately removed and 3 replicates of each treatment placed at 37° C. for thermal challenge whilst the other 3 were stored at 4° C. as post-lyophilisation controls. Thermal challenge was for 7 days, after which all the vials were returned to the control vials and all held at 4° C. until it was practical to assay them.

Assay of Recovered Infectious Virus from Rehydrated Cakes 96 flat bottomed cell culture dishes (VWR, UK) were seeded with HEK 293 (ECACC 85120602) cells at $10^5$ cells per ml (100 µl per well) and maintained at 37° C. with 5%

CO$_2$. After achieving 90% confluence vials containing the adenovirus plus excipient were reconstituted in 300 µl of PBS. The reconstituted samples were serially diluted 1:10 and 1:100 in DMEM plus 5% FBS. 100 µl of each of the resulting diluted virus samples were then added to individual wells of the plate. After a further 48 hours, the number of GFP cells per well were counted using fluorescent microscopy.

Protection of Adenoviral Infectivity During Lyophilisation (FIG. 6)

The samples were assayed 33 days after lyophilisation, and in the case of the heat challenged samples after 7 days at 37° C. followed by a further 26 days stored at 4° C. The results are shown in FIG. 6A.

S-methyl-L-methionine alone shows a concentration dependent protection of adenovirus during lyophilisation. Increased S-methyl-L-methionine in the formulation gave an increase in the recovered viral infectivity from reconstituted samples in this concentration range. Co-formulation of S-methyl-L-methionine with the low concentration treatment of sugars (0.1M Sucrose, 10 mM Raffinose) did not significantly alter this relationship. However, co-formulation of S-methyl-L-methionine with the high sugar treatment (1.0M Sucrose, 100 mM Raffinose) did significantly enhance the recovery of viral infectivity at low S-methyl-L-methionine concentrations.

On this evidence the optimum formulation for protection of viral infectivity during lyophilisation would appear to be either a high concentration of S-methyl-L-methionine (>0.07M) with no sugars or a concentration of less than 0.23M S-methyl-L-methionine in co-formulations with high sugar concentrations (1.0M Sucrose, 100 mM Raffinose).

Protection of Adenoviral Infectivity During Lyophilisation and Thermal Challenge at 37° C. (FIG. 6)

In the absence of any sugars in the formulation S-methyl-L-methionine offers only very limited retention of viral infectivity during lyophilisation and subsequent thermo-challenge (FIG. 6B). Even this limited protection is only seen at concentrations of 0.07M and above. Co-formulation with a low concentration of sugars (0.1M Sucrose, 10 mM Raffinose) similarly offers little protection although efficacy may be enhanced at low S-methyl-L-methionine concentrations.

Co-formulation of S-methyl-L-methionine with a high concentration of sugars (1M Sucrose, 100 mM Raffinose) demonstrates a clear enhancement of protection between 0.00M and 0.23M S-methyl-L-methionine, and this enhancement is well above an additive effect and could possibly therefore be considered true synergism at both 0.07M and 0.23M. The optimum concentrations appear to be S-methyl-L-methionine at between 0.05 and 0.1M formulated with high sugar concentrations (1M Sucrose, 100 mM Raffinose). However even in this range the recovery is around 2-3×10$^5$ pfu/ml which represents almost a log reduction over the assayed titre of the input virus.

Example 5

Recombinant adenovirus (Vector Biolabs) expressing enhanced GFP (Green Fluorescent Protein) under a CMV promoter was formulated with excipient mixtures so that, after lyophilisation, levels of recovered infectious adenovirus could easily be assayed. Each type of excipient plus virus (see Table 6 below) was made up as a stock in PBS and 300 µl added to appropriately labelled 5 ml glass vials. After vortexing, rubber bungs were partially inserted and vials were loaded onto the VirTis Advantage freeze dryer and freeze-dried (FD) as according to the freeze-drying protocol given above. Following freeze drying, samples virus titre was assessed in an adenovirus assay as described below.

TABLE 6

Final concentrations of excipient mixes in Example 5

| DMG (M) | Sucrose (M) | Raffinose (mM) | Virus |
|---|---|---|---|
| 0.7 | 1 | 100 | Y |
| 0.2 | 1 | 100 | Y |
| 0.07 | 1 | 100 | Y |
| 0.7 | 0 | 0 | Y |
| 0.2 | 0 | 0 | Y |
| 0.07 | 0 | 0 | Y |
| 0 | 1 | 100 | Y |
| 0 | 0 | 0 | Y |

Samples were freeze dried by the VirTis Advantage freeze dryer according to the protocol given in the general experimental techniques section above. Following freeze-drying, the samples were assayed in an adenovirus assay as described in Example 1.

Figure 7:
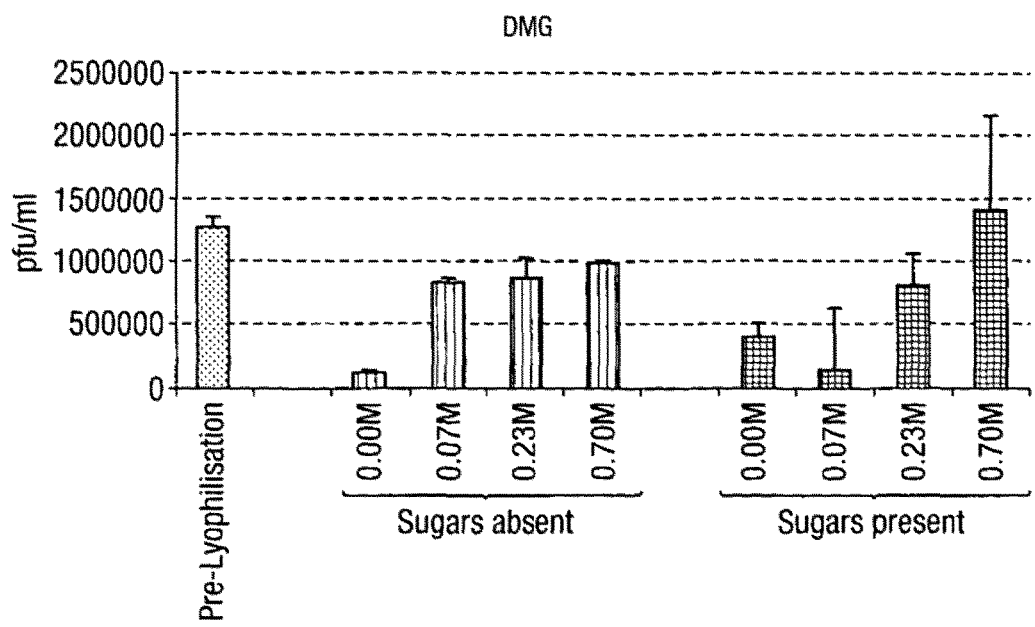
FIG. 7 shows the results obtained in Example 5 for adenovirus samples which were tested immediately after thawing ("Pre-Lyophilisation") as well as those of samples which were formulated in PBS (phosphate buffered saline) at DMG concentrations of 0.00M, 0.07M, 0.23M and 0.70M with and without sugars and which were subsequently lyophilised. Adenovirus activity stated as pfu/ml was assessed by counting cells positive for GFP (Green Fluorescent Protein) expression. The error bars shown are the standard error of the mean (n=3).

The results as shown in FIG. 7. Recovery of adenovirus lyophilised in PBS is typically low and this was reproduced in this experiment.

DMG alone provided protection of adenoviral infectivity during lyophilisation, and this compares favourably to sugars alone. The formulation of sugars and DMG demonstrated a dose-dependent protection. The highest concentration of DMG appears comparable to adenovirus pre-lyophilisation.

Example 6

The experiment in this Example expands on the capacity of DMG to protect adenovirus during lyophilisation in conjunction with raffinose and sucrose, by exploring the capability of DMG to protect adenovirus during thermal challenge. Two concentrations of each of the sugars at a static ratio to each other were tested (High sugars=1M Sucrose with 100 mM Raffinose, Low sugars=0.1M Sucrose with 10 mM Raffinose), whilst five concentrations of DMG were investigated (0.007M, 0.023M, 0.070M, 0.230M, 0.700M).

A strain of adenovirus expressing GFP was formulated with the excipient mixtures so that, after lyophilisation and thermal treatment, levels of recovered infectious adenovirus could easily be assayed. Adenovirus was formulated with the excipients and lyophilized before storage at +4° C. and +37° C. for one week. Samples were subsequently inoculated to HEK293 cells and recovered virus assessed by counting the number of GFP-expressing cells at 48 hours post-inoculation.

Materials and Methods

Preparation and Lyophilisation of Formulated Virus

Figure 8:
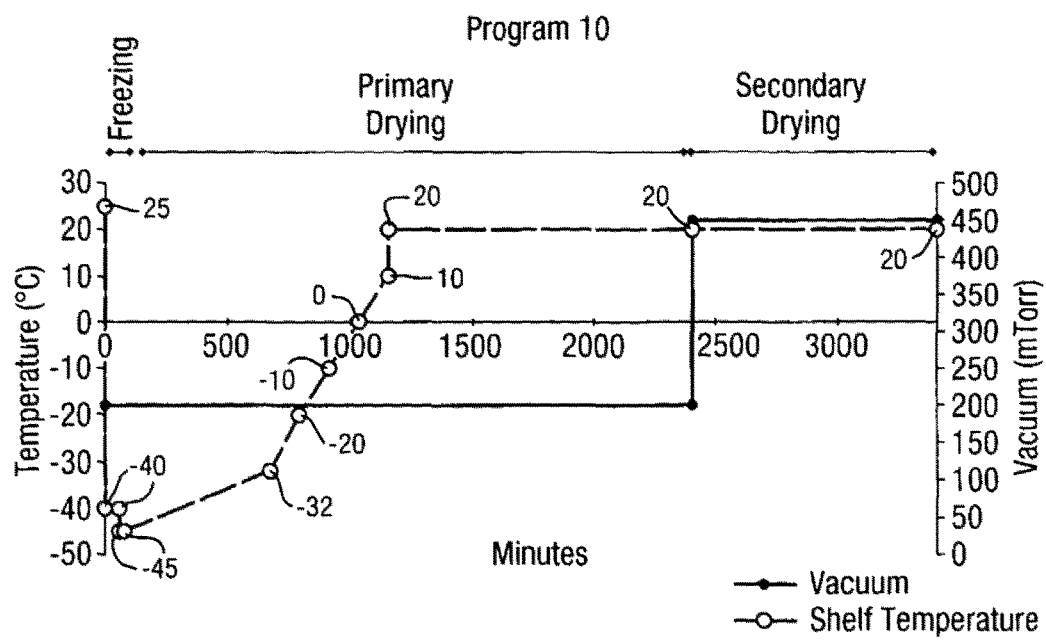
FIG. 8 shows the lyophilisation conditions used in Examples 5 and 6.

Recombinant adenovirus (Vector Biolabs) expressing enhanced GFP under a CMV promoter, and with a titre (pre-freeze) of 2×10$^6$ pfu/ml, was removed from storage at −80° C. and allowed to thaw. 50 µl aliquots of the virus were diluted to 300 µl in PBS containing a variable concentration of each of the excipients. A full list of excipient formulations tested can be seen in Table 7 below. Each treatment was made up in 6 replicate 5 ml vials. Rubber bungs were partially inserted, and after vortexing were loaded onto the VirTis Advantage freeze-dryer and lyophilised on program 10 (see FIG. 8).

TABLE 7

Summary of excipient treatments, each treatment was made in triplicate

| Sucrose (M) | Raffinose (mM) | DMG (M) | Thermal Challenge (° C.) |
|---|---|---|---|
| 0.0 | 0 | 0.000 | 37 |
| 0.0 | 0 | 0.007 | 37 |
| 0.0 | 0 | 0.023 | 37 |
| 0.0 | 0 | 0.070 | 37 |
| 0.0 | 0 | 0.230 | 37 |
| 0.0 | 0 | 0.700 | 37 |
| 0.1 | 10 | 0.000 | 37 |
| 0.1 | 10 | 0.007 | 37 |
| 0.1 | 10 | 0.023 | 37 |
| 0.1 | 10 | 0.070 | 37 |
| 0.1 | 10 | 0.230 | 37 |
| 0.1 | 10 | 0.700 | 37 |
| 1.0 | 100 | 0.000 | 37 |
| 1.0 | 100 | 0.007 | 37 |
| 1.0 | 100 | 0.023 | 37 |
| 1.0 | 100 | 0.070 | 37 |
| 1.0 | 100 | 0.230 | 37 |
| 1.0 | 100 | 0.700 | 37 |
| 0.0 | 0 | 0.000 | 4 |
| 0.0 | 0 | 0.007 | 4 |
| 0.0 | 0 | 0.023 | 4 |
| 0.0 | 0 | 0.070 | 4 |
| 0.0 | 0 | 0.230 | 4 |
| 0.0 | 0 | 0.700 | 4 |
| 0.1 | 10 | 0.000 | 4 |
| 0.1 | 10 | 0.007 | 4 |
| 0.1 | 10 | 0.023 | 4 |
| 0.1 | 10 | 0.070 | 4 |
| 0.1 | 10 | 0.230 | 4 |
| 0.1 | 10 | 0.700 | 4 |
| 1.0 | 100 | 0.000 | 4 |
| 1.0 | 100 | 0.007 | 4 |
| 1.0 | 100 | 0.023 | 4 |
| 1.0 | 100 | 0.070 | 4 |
| 1.0 | 100 | 0.230 | 4 |
| 1.0 | 100 | 0.700 | 4 |

Thermal Challenge of Lyophilised Adenovirus

After lyophilisation, samples were immediately removed and 3 replicates of each treatment placed at +37° C. for thermal challenge whilst the other 3 were stored at +4° C. as post-lyophilisation controls. Thermal challenge was for 7 days, after which all the vials were returned to the control vials and held at +4° C. until it was practical to assay them.

Assay of Recovered Infectious Virus from Rehydrated Cakes 96 flat bottomed cell culture dishes (VWR, UK) were seeded with HEK 293 (ECACC 85120602) cells at 105 cells per ml (100 µl per well) and maintained at 37° C. with 5% CO2. After achieving 90% confluence vials containing the adenovirus plus excipient were reconstituted in 300 ml of PBS. The reconstituted samples were serially diluted 1:10 and 1:100 in DMEM plus 5% FBS. 100 ml of each of the resulting diluted virus samples were then added to individual wells of the plate. After a further 48 hours, the number of GFP cells per well were counted using fluorescent microscopy. The results are shown in FIGS. 9A and 9B.

Results and Discussion

Figure 9A:
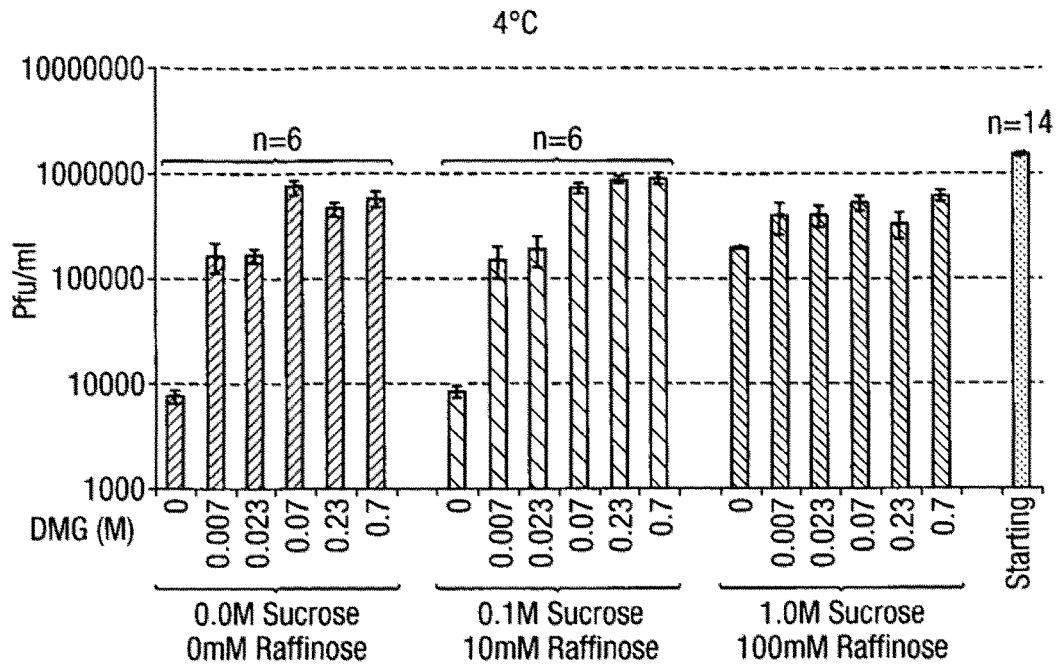
FIG. 9 shows the results obtained in Example 6 for adenovirus samples tested immediately after defrosting as well as those of samples lyophilised after formulation with DMG with or without sugars and subsequently thermochallenged. (A) Adenovirus activity after lyophilisation and storage at +4° C. for 7 days. (B) Adenovirus activity after lyophilisation and thermal challenge at +37° C. for 7 days. Error bars denote standard of mean; n=3 unless stated otherwise.
Figure 9B:
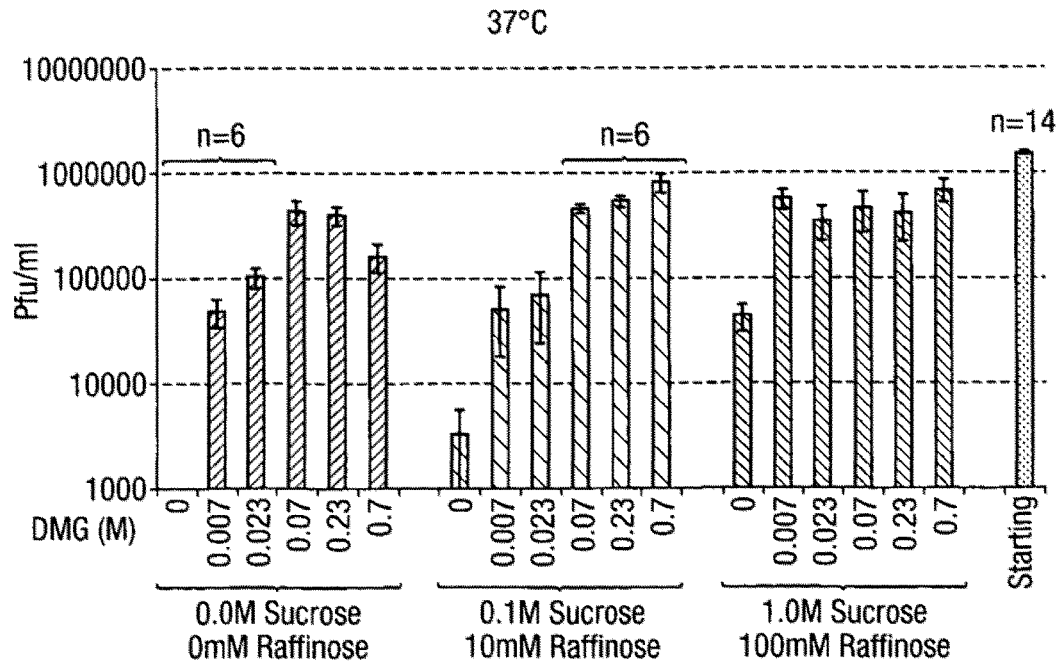

Protection of Adenoviral Infectivity During Lyophilisation (See FIG. 9a)

Samples stored at 4° C. for the duration of the test period after lyophilisation were assayed as a proxy for post-lyophilisation controls and also as negative controls for the thermal-challenge. In the absence of any excipients the lyophilisation of adenovirus during this experiment reduced infectivity of the sample from $1.5 \times 10^6$ pfu/ml to less than $1.0 \times 10^4$ pfu/ml.

Use of DMG as an excipient with adenovirus enhanced recovery of viral infectivity after reconstitution of the freeze dried cakes. The optimal concentration of DMG for the protection of adenovirus during lyophilisation in this experiment appears to be 0.07M or greater. Using the excipients, recovered titres of between $7.5-8.5 \times 10^5$ pfu/ml are readily achievable (compared to an input titre of $1.5 \times 10^6$ pfu/ml).

Protection of Adenoviral Infectivity During Lyophilisation and Following Thermal Challenge at +37° C. (see FIG. 9B)

No detectable recovery of viral infectivity was observed from vials containing no excipients (adenovirus in PBS) after thermal challenge at +37° C. This represents a very significant loss of viral infectivity over samples with an equivalent formulation held at +4° C.

It is possible to recover viral infectivity after thermal challenge from samples formulated with sugars alone (for example, 1.0M Sucrose, 100 mM Raffinose). Unfortunately, the recovered viral titre is only $4.3 \times 10^4$ pfu/ml compared to $1.9 \times 10^5$ pfu/ml from samples held at 4° C. for the duration of the test.

When DMG was used as the sole excipient, the optimum concentration of DMG appeared to be 0.07M or greater with recovery of around $7.5 \times 10^5$ pfu/ml. At DMG concentrations up to 0.07M (0.007-0.07M) there is a positive correlation between DMG concentration and recovered virus. Above 0.07M DMG its effect appears to be saturated.

Coformulation of adenovirus with the same lower concentration of sugars and DMG at 0.07M or above was at least as good as the equivalent DMG concentrations in the absence of any sugars and possibly gave a slight enhancement of the protective effect.

Coformulation of DMG at 0.023M or less, with the higher sugar concentration (1.0M Sucrose, 100 mM Raffinose), enhanced recovery to levels comparable to those treatments in which the DMG effect was thought saturated. However, at DMG concentrations of 0.07M or above the addition of the high sugar concentration has no obvious benefit. These findings suggest that the addition of sugars to DMG formulations at the higher concentration (1.0M Sucrose, 100 mM Raffinose) reduces the amount of DMG required to saturate its effect.

Example 7

Recombinant adenovirus (Vector Biolabs) expressing enhanced GFP under a CMV promoter was formulated with excipient mixtures so that, after lyophilisation, levels of recovered infectious adenovirus could easily be assayed. Each type of excipient (see Table 8 below) was made up as a stock and 250 µl added to appropriately labelled 2 ml glass vials. 50 µl of adenovirus was added to each vial from stocks. After vortexing, vials were loaded onto the VirTis Advantage freeze drier and freeze-dried.

TABLE 8

Final concentrations of excipient mixes for Example 7

| 0.7M DMG | 0.07M Mannitol | 0.7M DMG, 0.07M Mannitol |
|---|---|---|

Freeze Drying Protocol

Samples were freeze dried by the VirTis Advantage freeze dryer, using the pre-programmed protocol lasting for approximately 3 days. Samples were frozen at −40° C. for 1 hour before a vacuum was applied, initially at 300 milliTorre with a Thermo SAVANT™ VLP pump (Thermofisher, UK).

Shelf temperature and vacuum were adjusted throughout the process and the condenser was maintained at −80° C. Step 9 was extended until the samples were stoppered before releasing the vacuum. The drying cycle used is shown in Table 9 below:

TABLE 9

Freeze drier conditions

| Step | Shelf temp (° C.) | Time (mins) | Ramp/Hold | Vacuum (milliTorre) |
|---|---|---|---|---|
| 1 | −45 | 15 | H | 300 |
| 2 | −34 | 30 | R | 300 |
| 3 | −34 | 1200 | H | 300 |
| 4 | −20 | 120 | R | 300 |
| 5 | −10 | 120 | R | 300 |
| 6 | 0 | 120 | R | 300 |
| 7 | 10 | 120 | R | 80 |
| 8 | 20 | 1250 | H | 80 |
| 9 | 20 | 1250 | H | 80 |
| 10 | 20 | 1250 | H | 80 |

Figure 10:
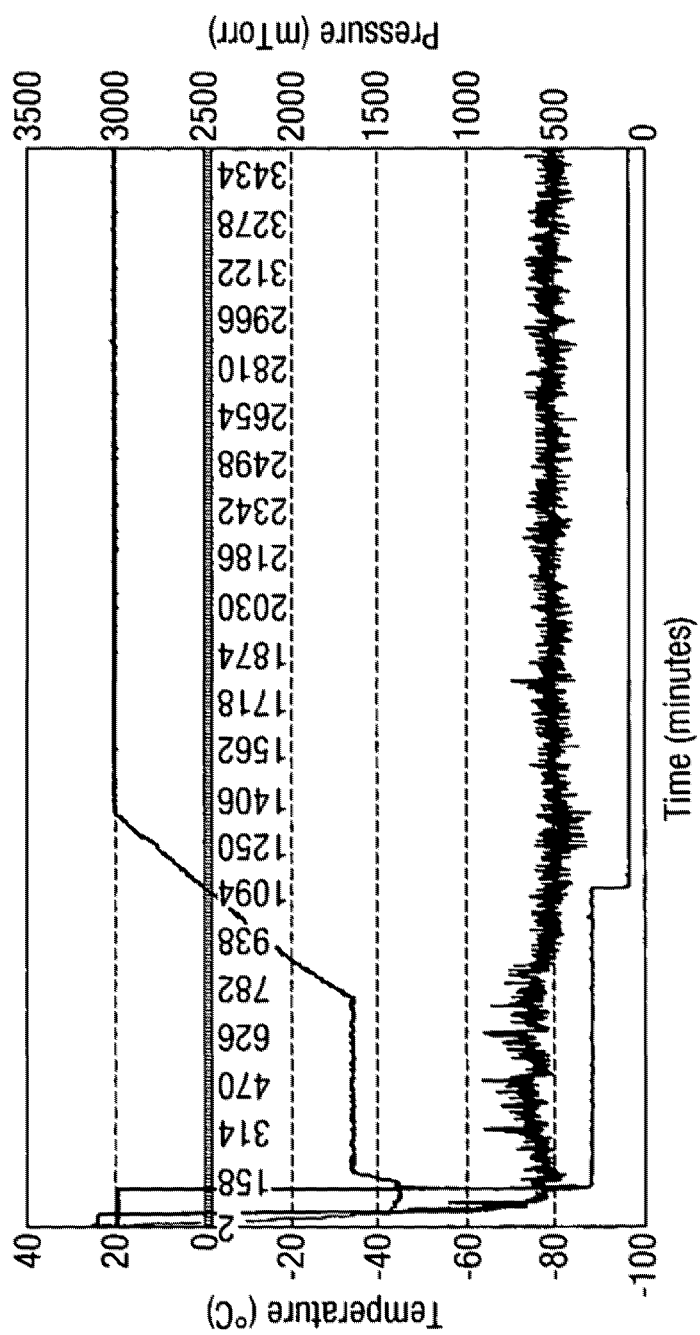
FIG. 10 shows the shelf temperatures, condenser temperatures and vacuum conditions during freeze drying in the VirTis Advantage freeze-dryer in Example 7.

In the primary drying phase, the shelf temperature is held at −34° C. The secondary drying phase included a ramp to +20° C. until the drying was completed. The condenser temperature was set to stay at a constant −80° C. Probes recorded shelf temperatures and condenser temperatures (see FIG. 10).

Adenovirus Assay 96 flat bottomed cell culture dishes (Jencons, UK) were seeded with REK 293 cells (ECACC 85120602) at $10^5$ cells per ml (100 µl per well) and maintained at 37° C. with 5% $CO_2$. After achieving 90% confluence, vials containing the adenovirus plus excipient were reconstituted in 1 ml of Dulbecco's Minimum Essential Medium (DMEM) plus 5% Foetal Bovine Serum (FBS). A 1:10 dilution step was carried out by taking 100 µl from the reconstituted vial and adding to 900 µl of DMEM. 100 µl of the resulting diluted virus was then added to the first row on the plate and a 1:2 dilution ran down the plate. The process was repeated with the next excipient. After a further 48 hours, the number of GFP cells per well were counted using fluorescent microscopy.

Statistical Analysis

A one way ANOVA test followed by a Bonferroni post test was performed to analyse significance between different excipients using PRISM Graphpad software version 4.00. The p value summaries are *=$p<0.05$; =$p<0.01$; *=$p<0.001$.

Results and Discussion

Figure 11:
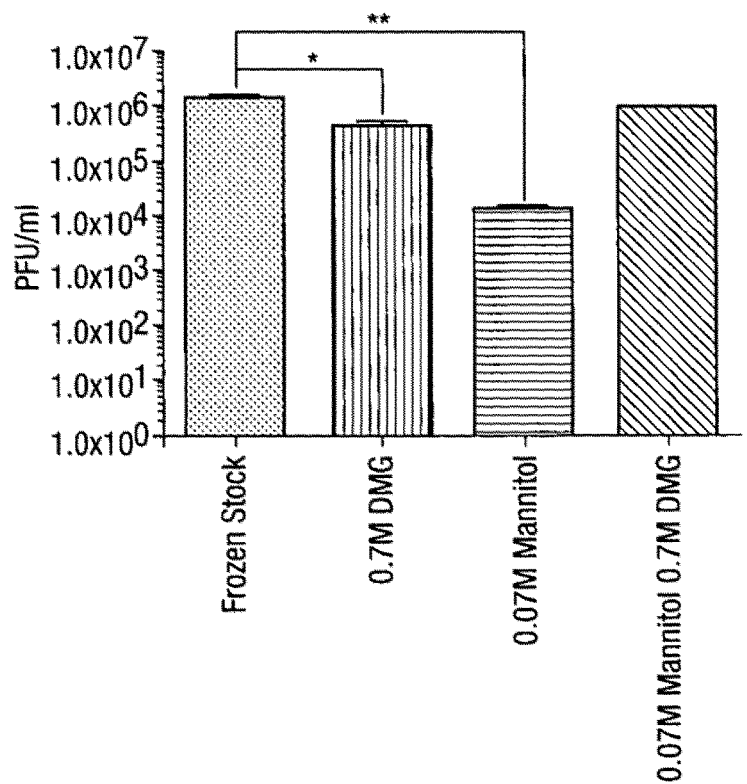
FIG. 11 shows the results obtained in Example 7. Adenovirus activity stated as pfu/ml was assessed by counting cells positive for GFP. Error bars denote standard of the mean (n=2). Significance was tested using a one way ANOVA followed by a bonferroni post test. The p value summaries are *=p<0.05 and **=p<0.01.

FIG. 11 shows the benefit of a combination of mannitol and DMG on the preservation of adenovirus titre following freeze drying. Following freeze drying there was approximately half a log drop in virus titre when DMG was used as an excipient on its own. When mannitol was the sole excipient the loss in titre was more significant than DMG with virus titre being reduced by 2 logs. When however both mannitol and DMG were used, there was no significant loss in titre and the appearance of freeze-dried cake improved.

Example 8

The aim of the experiment in this Example was to assess cake formation. Example 8 was conducted in the same manner as Example 7 except that a broader panel of excipients mixes were employed. Each type of excipient (see Table 10 below) was made up as a stock and 300 µl added to appropriately labelled 2 ml glass vials. After vortexing, vials were loaded onto the VirTis Advantage freeze drier which was nm according to the freeze drying protocol given in Table 9. Following freeze drying, samples were photographed and assessed for cake formation.

TABLE 10

Final concentrations of excipient mixes for Example 8

| 0.7M DMG, 0.018M Mannitol | 0.7M DMG, 0.03M Mannitol | 0.7M DMG, 0.07M Mannitol | 0.7M DMG, 0.15M Mannitol | 0.7M DMG, 0.29M Mannitol | 0.7M DMG, 0.58M Mannitol |
|---|---|---|---|---|---|

Figure 12:
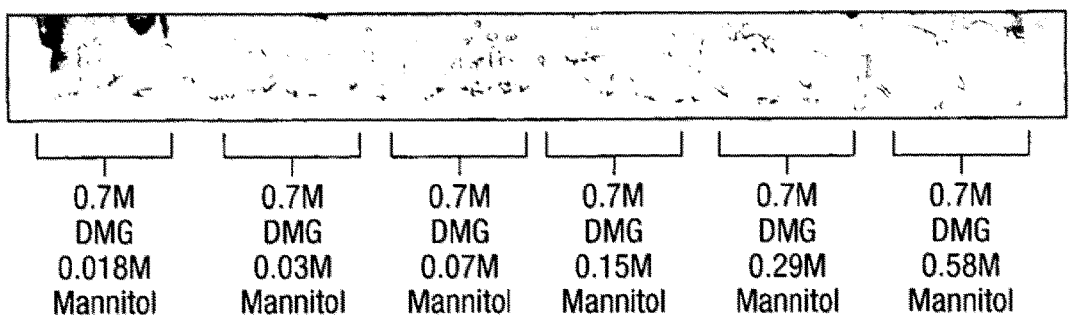
FIG. 12 shows the appearance of the freeze-dried cakes obtained in Example 8.

The appearance of the lyophilised cakes following freeze drying was examined. The results are shown in FIG. 12. Various concentrations of mannitol were used in the presence of 0.7M DMG. The highest mannitol concentration was 0.58M and the lowest was 0.018M. At the highest concentration of mannitol (0.58M), a white opaque cake was formed. As the concentration decreased, a less desirable transparent clear foam was formed.

Example 9

Example 9 was conducted in the same manner as Example 7 except that only two types of excipients were prepared. The first excipient was the adenovirus in PBS made up to a final volume of 300u1. The second excipient was mannitol (0.58M) and DMG (0.7M) with the adenovirus in 2 ml glass vials. After vortexing, vials were loaded onto the VirTis Advantage freeze drier and freeze-dried according to the freeze drying protocol given in Table 9. Following freeze drying, samples were either assayed for virus titre or heat treated for one week at +37° C. and then assayed.

Figure 13:
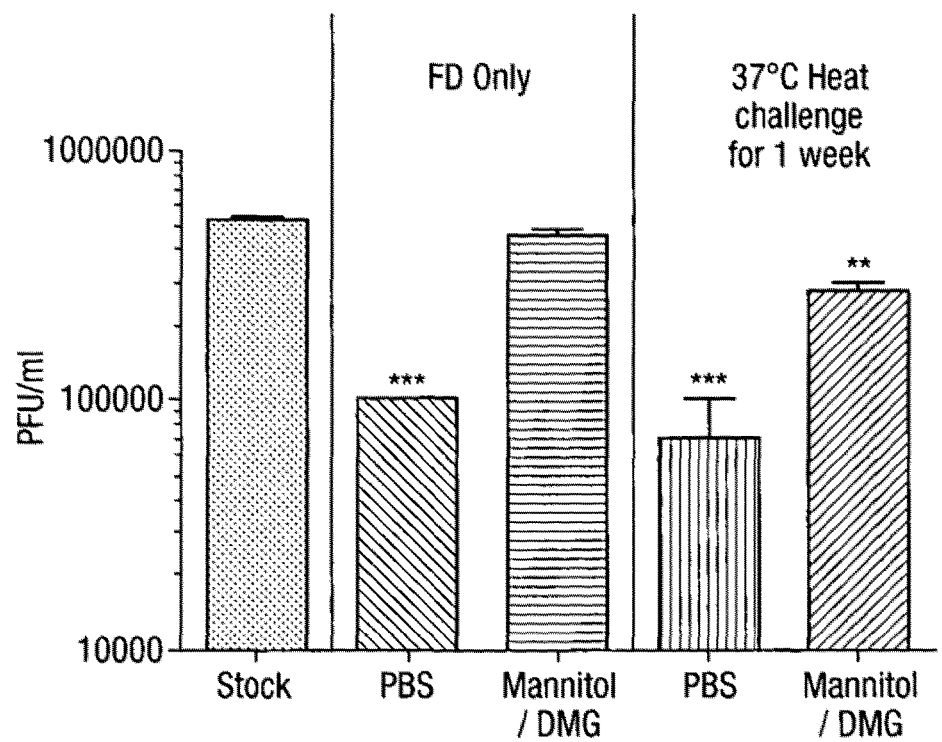
FIG. 13 reports the results obtained in Example 9. FD denotes freeze drying. Vials containing adenovirus and PBS only showed a much greater loss of virus titre compared to the vials containing adenovirus, mannitol and DMG. Error bars shown are the standard error of the mean (n=2). Significance was tested using a one way ANOVA followed by a bonferroni post test. All values were compared to stock titre. The p value summaries are =p<0.01 and *=p<0.001.

The results are shown in FIG. 13. After freeze drying, there was a drop in virus titre of greater than half a log in the PBS controls. No significant loss in virus titre was seen in samples containing DMG and mannitol compared to the original virus stock. After heat treatment at +37° C., there was again a drop in virus titre of greater than half a log in the PBS controls. The virus titre in the samples containing DMG and mannitol declined by approximately 0.3 log compared to the original stock titre.

Example 10: Stablisation of Adenovirus

Preparation and Lyophilisation of Virus

Recombinant human adenovirus Ad5 (Vector Biolabs) expressing enhanced GFP (Green Fluorescent Protein) under a CMV promoter, and with a titre (pre-freeze) of $6.7 \times 10^5$ pfu/ml in SSC, was removed from storage at −80° C. and allowed to thaw. 50 µl aliquots were added to 2 ml freeze-drying vials. To these 50 µl virus samples was added 250 µl of a formulation mixture composed of DMG, MSM and optionally sucrose. Each formulation mixture was made up in SSC. The concentration of DMG, MSM and sucrose in each formulation after addition to the virus sample is shown in Table 11:

TABLE 11

Tested formulations

| Formulation | Sucrose (M) | MSM (M) | DMG (M) |
|---|---|---|---|
| 1 | 0.00 | 0.10 | 0.10 |
| 2 | 0.15 | 0.10 | 0.10 |

TABLE 11-continued

Tested formulations

| Formulation | Sucrose (M) | MSM (M) | DMG (M) |
|---|---|---|---|
| 3 | 0.00 | 1.00 | 0.10 |
| 4 | 0.15 | 1.00 | 0.10 |
| 5 | 0.08 | 0.55 | 0.55 |
| 6 | 0.08 | 0.55 | 0.55 |
| 7 | 0.08 | 0.55 | 0.55 |
| 8 | 0.00 | 0.10 | 1.00 |
| 9 | 0.15 | 0.10 | 1.00 |
| 10 | 0.00 | 1.00 | 1.00 |
| 11 | 0.15 | 1.00 | 1.00 |

Rubber bungs were partially inserted. After vortexing, the vials were loaded onto a Virtis Advantage Plus EL85 freeze-dryer and lyophilised on program 4. Thus, samples were freeze dried using the drying cycles shown in Table 12 below. Samples were frozen at −45° C. for 1 hour before a vacuum was applied, initially at 300 milliTorre with a Thermo SAVANT™ VLP pump (Thermofisher, UK). Shelf temperature and vacuum were adjusted throughout the process and the condenser was maintained at −42° C. Step 11 was extended until the samples were stoppered before releasing the vacuum.

TABLE 12

Drying Cycles

| Step | Shelf temp (° C.) | Time (mins) | Ramp-Hold | Vacuum (milliTorre) |
|---|---|---|---|---|
| 1 | −45 | 30 | H | 300 |
| 2 | −34 | 30 | R | 300 |
| 3 | −34 | 1200 | H | 300 |
| 4 | −20 | 120 | H | 300 |
| 5 | −10 | 120 | H | 300 |
| 6 | 0 | 120 | H | 300 |
| 7 | 10 | 120 | H | 80 |
| 8 | 20 | 120 | H | 80 |
| 9 | 30 | 1255 | H | 80 |
| 10 | 30 | 905 | H | 80 |
| 11 | 4 | 1255 | H | 80 |

In the thermal treatment, the shelf temperature was dropped to −40° C.

Thermal Challenge of Lyophilised Virus

After lyophilisation, vials were immediately capped, removed, crimped and then placed at 37° C. for thermal challenge. Thermal challenge was for 7 days, after which all the vials were returned to 4° C. until it was practical to assay them.

Assay of Recovered Infectious Adenovirus from Rehydrated Cakes 96 flat bottomed cell culture dishes (VWR, UK) were seeded with HEK 293 (ECACC 85120602) cells at $10^5$ cells per nil (100 μl per well) and maintained at 37° C. with 5% $CO_2$. After achieving 90% confluence, cells were inoculated.

Vials containing adenovirus plus excipient were reconstituted in 300 μl SSC. A 1 in 10 dilution step was then taken by taking 20 μl from the reconstituted vial and adding to 180 μl of Dulbecco's Modified Eagle Medium (DMEM). A further 1 in 100 dilution (of the original sample) was performed by taking 20 μl of the 1 in 10 dilution and adding it to 180 μl of DMEM. 100 μl of each of the resultant dilution (1 in 10 and 1 in 100) was then added to wells of the plate containing HEK 293 cells.

Additionally, a further sample of adenovirus, from the same source and with the same titre (on storage at −80° C.) used in the excipient treatments, was thawed and used to produce a 1 in 10 dilution series (in DMEM+10% FBS). Dilutions ranging from 1 in 10 to 1 in $10^6$ were also added to individual wells containing HEK 293s. At 48 hours post inoculation, the number GFP (Green Fluorescent Protein) cells per well were counted using fluorescent microscopy, and this was subsequently converted to pfu/ml of the treated samples taking into account the volume applied and dilution of the inoculum.

Results

The results as shown in FIG. 14. When the data was analysed by multiple linear regression (MLR) analysis using the MODDE 9.0 programme (Umetrics, Sweden), a synergistic effect was observed when MSM and DMG were used in combination and when DMG and sucrose were used in combination.

Example 11: Stablisation of MVA

Preparation and Lyophilisation of Virus

MVA was recovered from storage at −80° C. and thawed. 50 μl aliquots were added to 2 ml freeze-drying vials. To these virus samples was added 250 μl of a formulation mixture listed in Table 11 above. Rubber bungs were partially inserted. After vortexing, the vials were loaded onto a Virtis Advantage Plus EL85 freeze-dryer and lyophilised on program 4 as described in Example 10.

Thermal Challenge of Lyophilised Virus

After lyophilisation, vials were immediately capped, removed, crimped and then placed at 37° C. for thermal challenge. Thermal challenge was for 7 days, after which all the vials were returned to 4° C. until it was practical to assay them.

Assay of Infectious MVA Recovered from Rehydrated Cakes

MVA plus excipient were reconstituted in 300 ml of SSC. The reconstituted samples were diluted and assayed.

Assay plates (96 wells) were seeded with BHK-21 cells (100 μl per well, $10^5$ cells/ml). Cells were diluted in DMEM supplemented with 10% FBS, and 1% PS. The plates were placed at +37° C., +5% $CO_2$ for 1 to 2 hours.

Meanwhile, a dilution series of the formulated MVA samples was prepared (in the same growth media) ranging from $10^{-1}$ to $10^{-4}$. Each dilution series was prepared 4 times. 35 μl of each dilution was applied to individual wells containing BHK-21 cells and the wells were topped up with a further 65 μl of media.

On day 6 after inoculation, the wells were scored for presence or absence of cytopathic effect (CPE) and $TCID_{50}$ calculated. These were then used to estimate the concentration of infectious MVA per ml in the thermo-challenged vials.

Results

The results are shown in FIG. 15. The range of responses in this screening to study was from 0.6-60.5% of starting titre (see FIG. 15). This was assessed relative to a second aliquot of the virus held at −80° C. until assay. FIG. 15 shows the response to each formulation treatment as percentage of a positive control. The best performing formulation comprised 0.15M sucrose, 1M DMG, 1M MSM. Overall, the results strongly suggest that this combination of excipients has significant potential for the stabilisation of viruses in a freeze-dried setting.

Example 12

Materials

| Chemical | Supplier | Product Code | Lot No. |
|---|---|---|---|
| 20x SSC | Sigma | S6639 | 020M8404 |
| Betaine | Sigma | B2629 | 069K1514 |
| Dimethyl glycine | Sigma | D1156 | 077K1856 |
| Dimethyl sulfone | Sigma | M81705 | 0001452516 |
| Dulbeccos Modified Eagles Medium | Sigma | D5796 | RNBB1139 |
| Foetal Bovine Serum | Sigma | F7524 | 109K3395 |
| Penicillin Streptomycin | Sigma | P4458 | 0409M0093 |
| Raffinose | Sigma | R0250 | 050M0053 |
| S-Methyl methionine | Sigma | 64382 | |
| Sucrose | Sigma | 16104 | SZB90120 |
| Water | Sigma | W3500 | 8M0411 |
| X-Gen 500 P-Lin | Fermentas | R0521 | 00064973 |

| Biological | Supplier | Product Code |
|---|---|---|
| Adenovirus | Vector Biolabs | Ad-CMV-GFP |
| BHK-21 cell line | ECACC | CB2857 |
| HEK 293 | ECACC | 85120602 |

| Other | Manufacturer | Product Code |
|---|---|---|
| 5 ml glass vials | Adelphi Tubes | VCD005 |
| 14 mm freeze drying stoppers | Adelphi Tubes | FDIA14WG/B |
| 14 mm caps | Adelphi Tubes | CWPP14 |
| 2 ml glass vials | Adelphi Tubes | VCDIN2R |
| 13 mm freeze drying stoppers | Adelphi Tubes | FDW13 |
| Crimps | Adelphi Tubes | COTW13 |

Equipment

| | Manufacturer | Equipment No. |
|---|---|---|
| Virtis Advantage Plus EL85 Freeze Dryer | Virtis | EQP#084 |
| HERASAFE ™ class II | Thermo Fisher | EQP# 011 & 012 cabinet |
| DMIL LED Inverted Microscope | Leica | EQP#062 |
| Binder $CO_2$ Incubator | Binder | EQP#014 |
| Forma 900 series −80° C. freezer | Thermofisher | EQP#015 |
| ATL-84-1 Atlion Balance | Acculab | EQP#088 |
| IP250 37° C. Incubator | LTE | EQP#016 |

Methods

Design of Experiment

Figure 16:
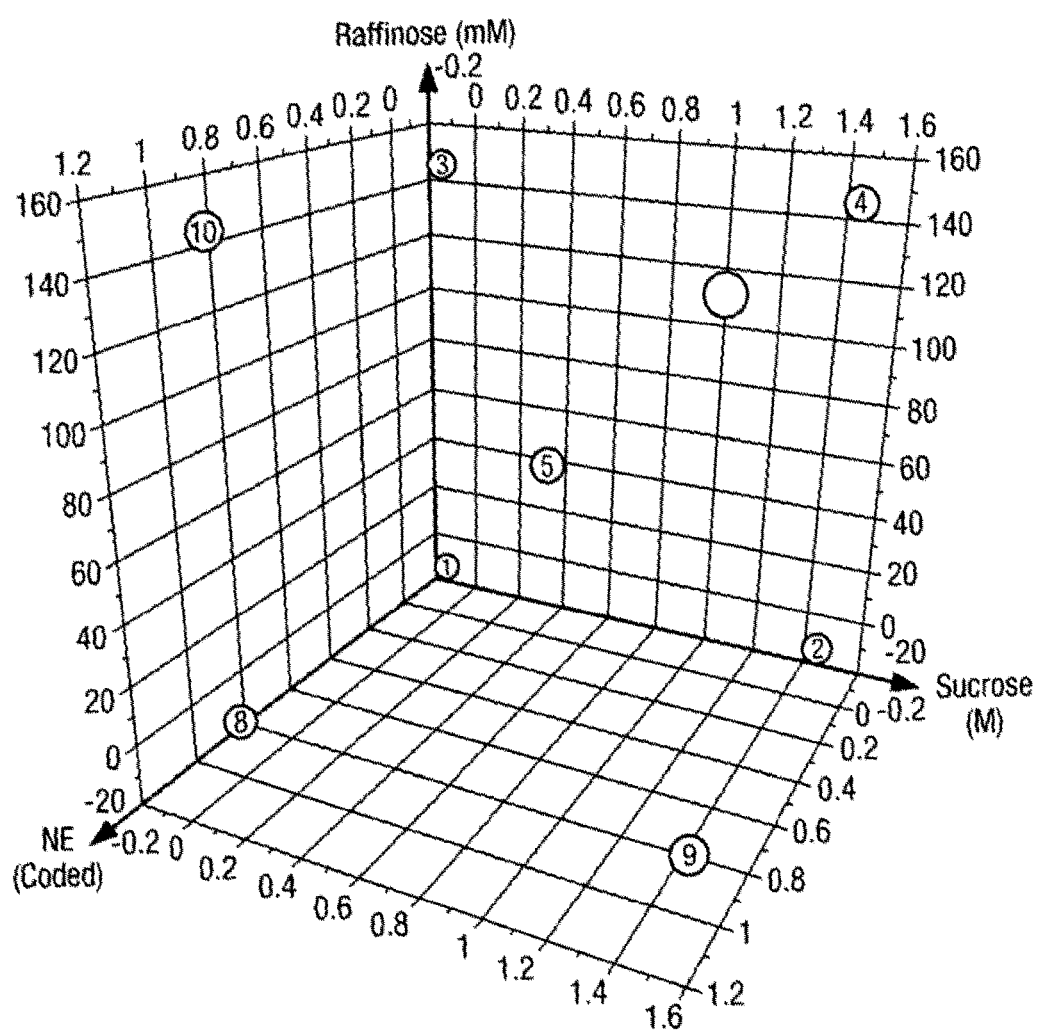
FIG. 16 shows a 3D representation of the design space in Example 12. Balls represent formulations within the design space that were tested. This design is a three factor, full factorial screening design.
Figure 18:
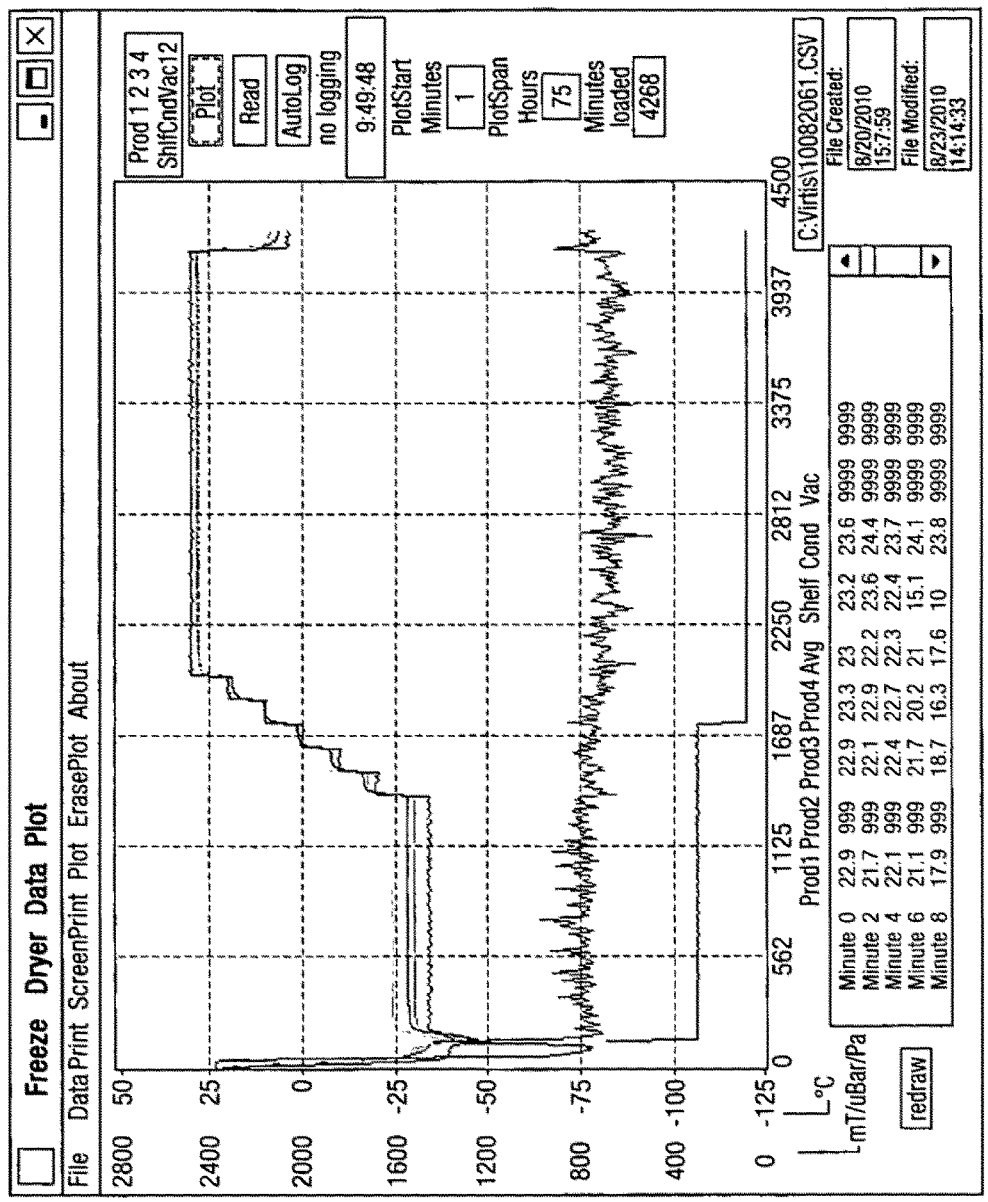

MODDE 9.0 was used to generate a three factor, two level full factorial screening design (see FIG. 16 showing coded values, and Table 13 showing actual concentrations applied). This design involves testing combinations of the excipients at the high and low levels of the tested range as well as replicated centre points. The replicated centre points give an indication of error in the experiment.

The design can model $1^{st}$ order effects of each tested factor (excipient) and interactions between them, that is, determine the impact of the presence of the exipients to the formulation. It cannot model $2^{nd}$ order of higher effects but can give an indication of whether they are present (curvature in the data). Second order effects result from covariance within the data, that is, two or more variables are dependent upon one another. Though $2^{nd}$ order effects are expected, the intent is to use this simple screening study, with minimal treatments, in order to detect any effect of the excipient and then take forward any excipient that have an effect into a more sophisticated study that can model the effects more accurately.

Stability of Adenovirus in a Lyophilised Setting

Preparation of and Thermal Challenge of Formulated Adenovirus in a Freeze-Dried Setting Recombinant Adenovirus expressing enhanced GFP under a CMV promoter, with a titre (pre-freeze) of $6.7 \times 10^5$ pfu/ml in saline sodium citrate (SSC), was removed from storage at −80° C. and allowed to thaw at room temperature. Subsequently, 50 μl aliquots of virus were added to 15 individual 2 ml glass freeze-drying vials. To each vial 250 μl of an excipient blend was admixed. The excipient blend formulations once mixed with virus are described in Table 13 and were made up in SSC.

TABLE 13

| Sample ID | Sucrose (M) | Raffinose (mM) | Excipient (M) | Titre (pfu/ml) DMG | SMM | TMG |
|---|---|---|---|---|---|---|
| 1 | 0.15 | 15.0 | 0.10 | 3.6E+3 | 6.0E+2* | 4.8E+3 |
| 2 | 1.50 | 15.0 | 0.10 | 6.0E+4 | 1.6E+5 | 1.0E+5 |
| 3 | 0.15 | 150.0 | 0.10 | 2.4E+3 | 6.0E+2* | 5.4E+3 |
| 4 | 1.50 | 150.0 | 0.10 | 9.0E+4 | 2.3E+5 | 9.0E+4 |
| 5 | 0.83 | 82.5 | 0.55 | 1.4E+5 | 1.7E+5 | 5.3E+4 |
| 6 | 0.83 | 82.5 | 0.55 | 1.6E+5 | 2.1E+5 | 1.2E+4 |
| 7 | 0.83 | 82.5 | 0.55 | 1.1E+5 | 2.7E+5** | 7.8E+4 |
| 8 | 0.15 | 15.0 | 1.00 | 1.9E+5 | 4.0E+4 | 2.9E+5 |
| 9 | 1.50 | 15.0 | 1.00 | 2.2E+5 | 9.0E+4 | 1.1E+5 |
| 10 | 0.15 | 150.0 | 1.00 | 1.9E+5 | 1.1E+5 | 3.1E+5 |
| 11 | 1.50 | 150.0 | 1.00 | 8.4E+4** | 1.7E+5 | 6.6E+3 |

*= count below detectable levels\assigned value of detection limit for ease of data transformation.
= datapoint excluded during model fine tuning as an apparent outler Rubber bungs were partially inserted, and after vortexing were loaded onto a VirTis Advantage Freeze Dryer and lyophilised on program 4 (see FIG. 17**). After lyophilisation samples were immediately capped under vacuum, removed, crimped and placed at 37° C. for thermal challenge. Thermal challenge was for 7 days, after which all the vials were held at 4° C. until it was practical to assay them. Freeze-dried samples were reconstituted in 300 μl SSC immediately prior to assay.

Assay of Adenovirus

HEK 293 cells were prepared in 96 well flat bottomed cell culture dishes for inoculation by seeding at $10^5$ cells per ml (100 μl per well) and maintained at 37° C. with 5% $CO_2$. After 2 hours cells were inoculated as follows.

Thermo-challenged virus samples were diluted 1 in 10, and 1 in 100 in DMEM+10% FBS. 100 μl of each of the resulting diluted virus samples were then added to individual wells of the assay plate. Additionally, a second aliquot of the original adenovirus in SSC was thawed from −80° C. and a 10 fold dilution series (from 1 in 10 to 1 in 100,000) also prepared in DMEM+10% FBS. Two repeats of this positive control dilution series was inoculated to each 96 well plate used. After a further 48 hours, the number of GFP cells per well were counted using fluorescent microscopy.

Results

General

A good range of responses was observed in each experiment. Most yielded a range of recovered viral activity of between just a few percent and 32-46% (see Table 14).

TABLE 14 model assessment parameters and range
of responses for each excipient tested

| | Model Assessment Parameters | | | | Data Spread (% Recovered Activity) | |
|---|---|---|---|---|---|---|
| | $R^2$ | $Q^2$ | MV | Rep. | Low | High |
| DMG | 0.95 | 0.88 | 0.94 | 0.89 | 0.36 | 32.84 |
| SMM | 0.5 | 0.4 | 0.71 | 0.88 | 0.09* | 40.30 |
| TMG | 0.75 | 0.54 | 0.88 | 0.60 | 0.72 | 46.27 |

*= below detectable limit there for assigned threshold value to allow easier data transformation This spread of responses was sufficient to permit a suitable model to be applied. It is also indicative of a protective effect of the formulations.

In several models the lowest response was below the detection threshold of the assay. For ease of transforming datasets (log transformations) the response in these cases was assigned the level of the detection threshold, which in this case (taking to account the countable level and then allowing for dilution factors etc.) is $6 \times 10^2$ pfu/ml.

Further modelling analyses are set out in Table 15 to 17.

TABLE 15 model assessment parameters from models where
a non-specific 2nd order interaction is allowed

| | $R^2$ | $Q^2$ | MV | Rep. |
|---|---|---|---|---|
| DMG | | No curvature | | |
| SMM | 0.95 | 0.66 | 0.89 | 0.88 |
| TMG | | No improved model | | |

TABLE 16 coefficients retained in the model after fine tuning

| | Factors/Interactions | | | | | | |
|---|---|---|---|---|---|---|---|
| | NE | Suc | Raff | NE x S | NE x R | S x R | Curvature |
| DMG | ✓ | ✓ | | | | | No |
| SMM | * | ✓ | * | * | | • | Yes |
| TMG | ✓ | * | • | ✓ | | • | Yes |

The following abbreviations/columns are present in Table 16
NE=novel excipient, Suc=sucrose, Raff=raffinose (all $1^{st}$ order effects).
NExS=interaction between NE and sucrose.
NExR=interaction between NE and raffinose.
SxR=interaction between sucrose and raffinose.
Curvature=indication of $2^{nd}$ order effect.
*=non-significant term retained in model for model stability.

TABLE 17 coefficients retained in the model after fine tuning
and inclusion of a hypothetical 2nd order effect

| | Factors/Interactions | | | | | | |
|---|---|---|---|---|---|---|---|
| | NE | Suc | Raff | NE x S | NE x R | S x R | 2nd order term |
| DMG | | | | No curvature | | | |
| SMM | • | ✓ | ✓ | ✓ | • | | ✓ |
| TMG | | | | No improved model | | | |

The following abbreviations/columns are present in Table 17
NE=novel excipient, Suc=sucrose, Raff=raffinose (all 1st order effects).
NExS=interaction between NE and sucrose.
NExR=interaction between NE and raffinose.
SxR=interaction between sucrose and raffinose.
Curvature=indication of 2nd order effect.
2nd order term=a 2nd order effect predicted by curvature in the data, that strengthens the models. The experimental design is unable to identify specific 2nd order effects.

DMG

Figure 19:
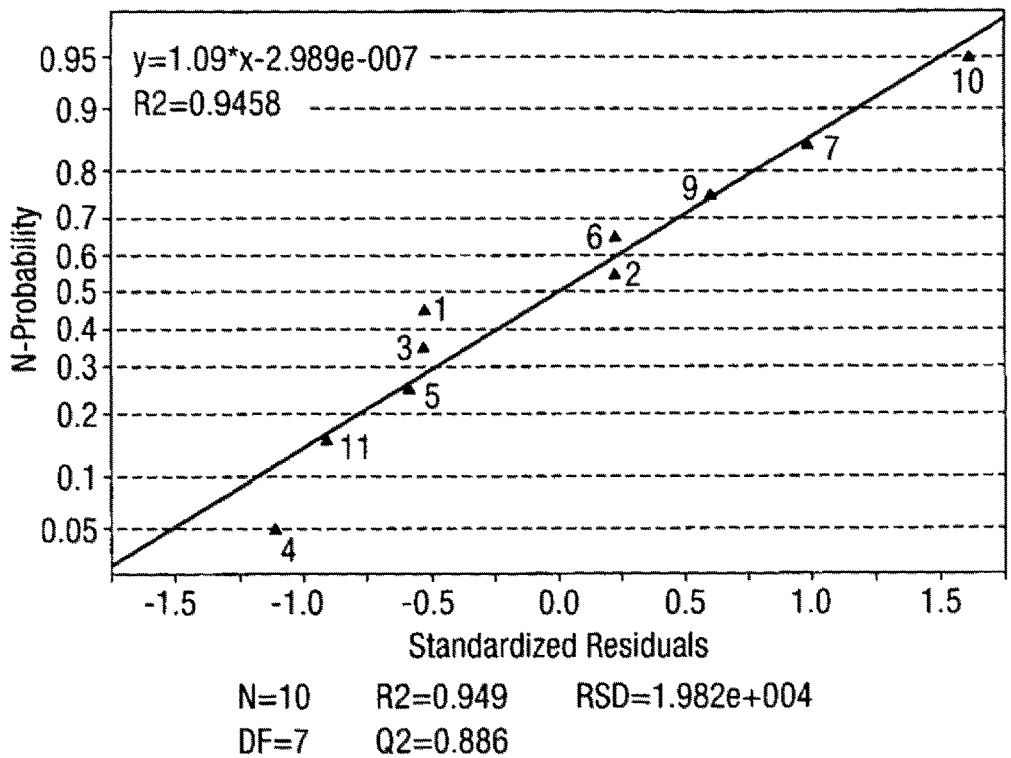
FIG. 19 shows a residual normal probability plot for data from formulations containing DMG in Example 12.
Figure 20:
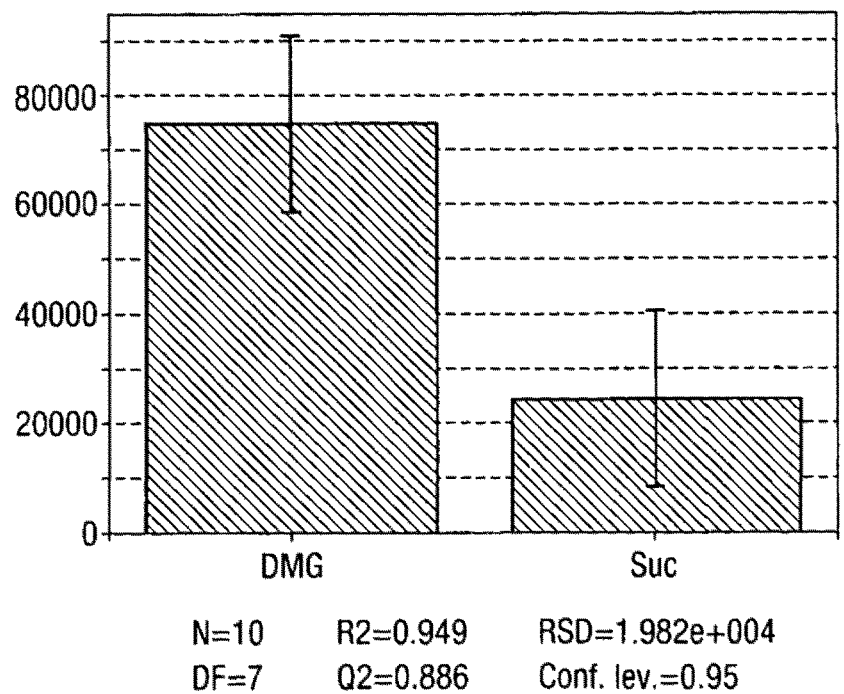
FIG. 20 shows retained coefficients (effects) of the modelled data from formulations containing DMG in Example 12. Error bars indicate significance if not crossing the origin.

A good spread of responses was found in this dataset (0.36-32.84% recovery) and notably the lowest response is above the detection limit (see Table 14). One data point, sample ID 11 (see Table 13) was eliminated from the analysis after being flagged as an obvious outlier during fine tuning of the model. The reason for this outlier is unknown but is presumed to be operator error. All four indicators of model strength are high (see Table 14), and no curvature was observed in the data (see FIG. 19). Only two critical factors were identified by the model, DMG and sucrose were each found to be significant positive $1^{st}$ order effects (see Table 16 and FIG. 20). No other effects or interactions were observed. Raffinose was not indicated as having an effect on the model and hence viral recovery in the range tested.

SMM

Figure 21:
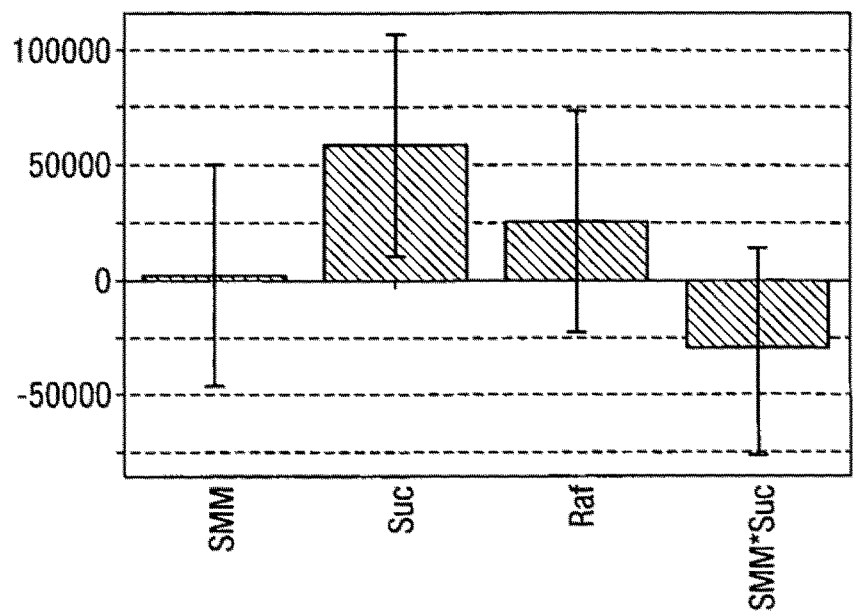
FIG. 21 shows retained coefficients (effects) of the modelled data from formulations containing SMM in Example 12. Error bars indicate significance if not crossing the origin.

A good range of responses was observed in this dataset (0.09-40.30% recovery) (see Table 14), although, the lowest in this range was below the detection threshold. During model fine tuning one data point (sample ID 7) was eliminated from the analysis as an obvious outlier (see Table 13). The first model generated identified only sucrose as a critical factor (see FIG. 21), however, it was necessary to retain non-significant factors (SMM, raffinose, and SMM*sucrose) within the model to achieve any sort of meaningful significance.

Figure 22:
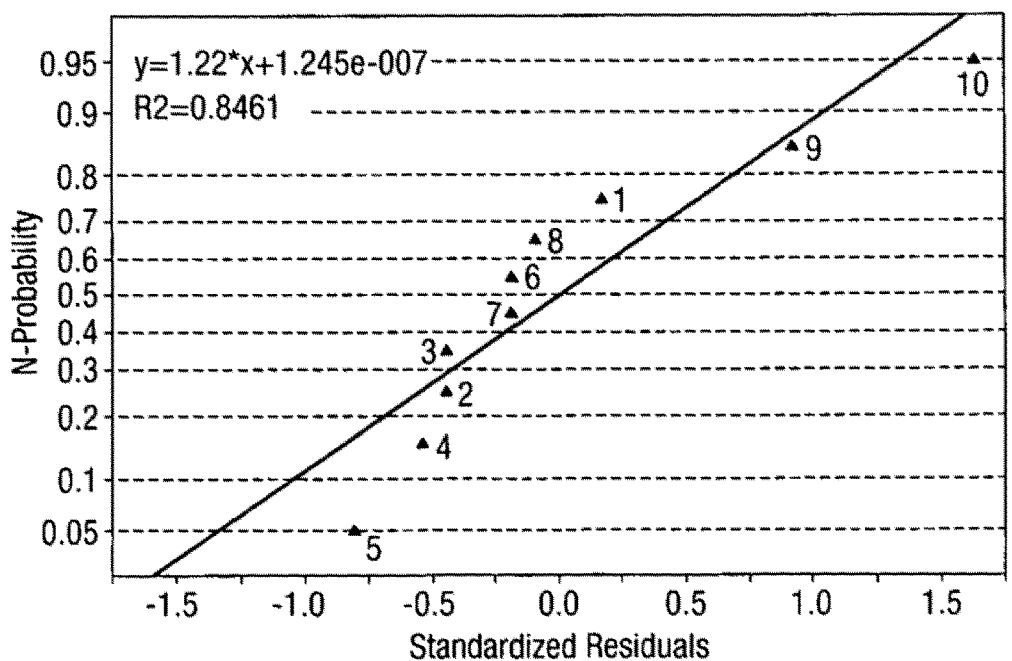
FIG. 22 shows a residual normal probability plot for data from formulations containing SMM in Example 12.
Figure 23:
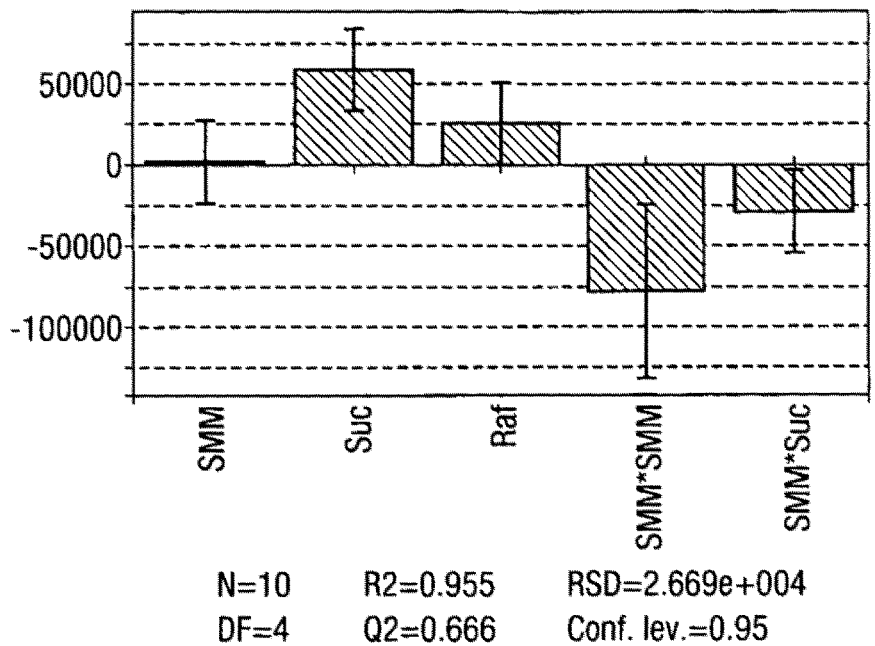
FIG. 23 shows retained coefficients (effects) of the modelled data from formulations containing SMM in Example 12 after inclusion of a non-specific $2^{nd}$ order term. Error bars indicate significance if not crossing the origin.
Figure 24:
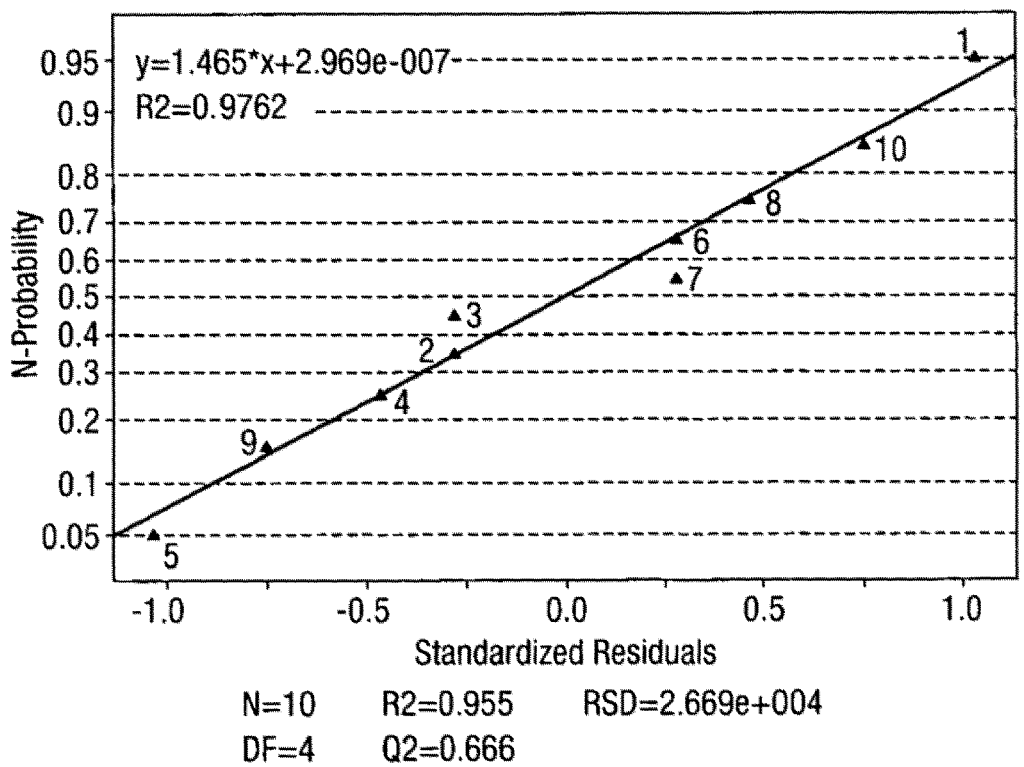
FIG. 24 shows a residual normal probability plot for data from formulations containing SMM in Example 12.

Even so, the model scores relatively poorly on $R^2$ and $Q^2$ (0.5 and 0.4 respectively). FIG. 22 shows evidence of curvature in the model. Following this observation a new model was developed with the inclusion of a $2^{nd}$ order effect. As in previous examples the specific $2^{nd}$ order effect cannot be identified with this experimental design. The new model scored more highly on all four model assessment parameters. This model identified sucrose, and raffinose as 1st order effects as well as an interaction between SMM and sucrose and the putative $2^{nd}$ order effect of one excipient. (see FIG. 23). This new model showed no evidence of curvature within the model (see FIG. 24).

TMG

Figure 25:
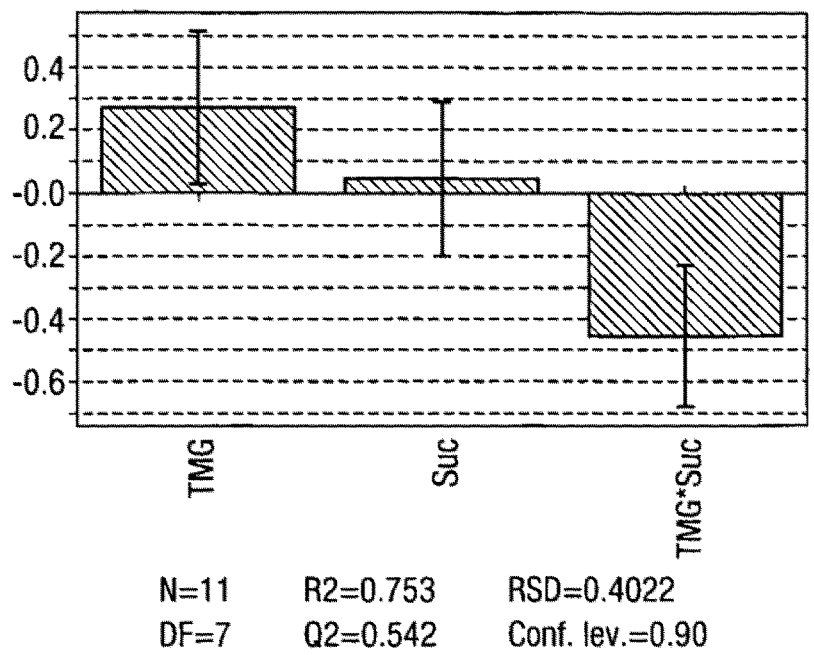
FIG. 25 shows retained coefficients (effects) of the modelled data from formulations containing TMG in Example 12. Error bars indicate significance if not crossing the origin.
Figure 26:
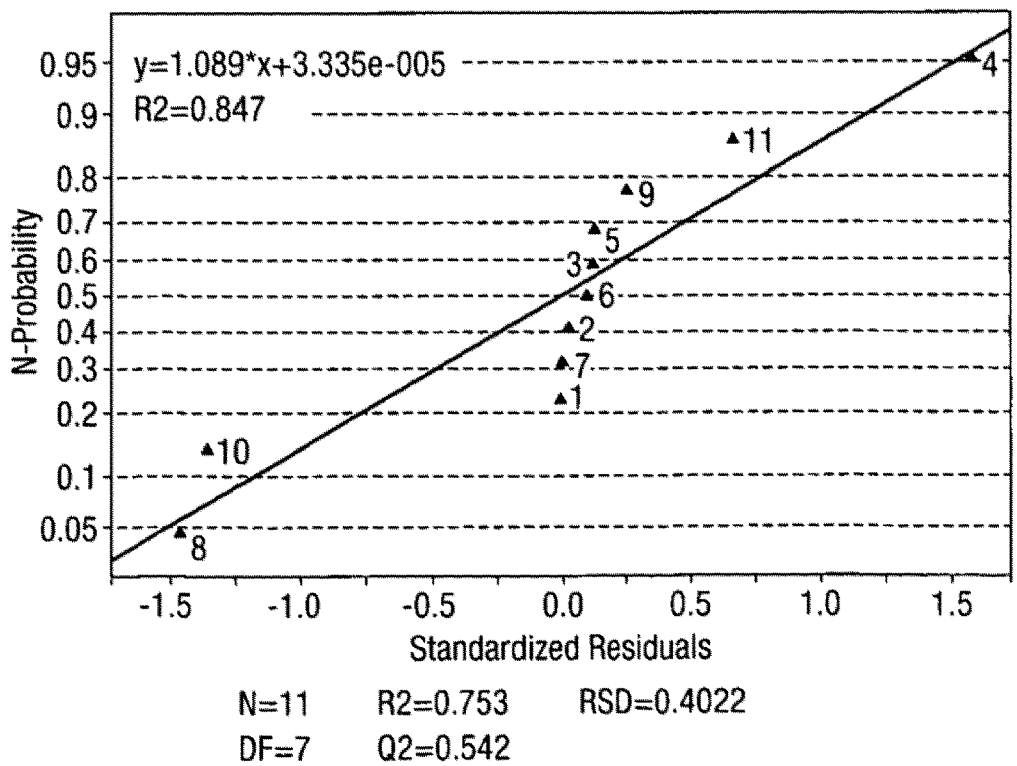
FIG. 26 shows a residual normal probability plot for data from formulations containing TMG in Example 12.

A good spread of responses was observed in this dataset (0.72-46.27%) and all the data points were above the detectable threshold (see Table 13). Acceptable scores were generated for all four model assessment parameters (see Table 14). The model identifies a $1^{st}$ order effect of TMG and an interaction between TMG and sucrose (see Table 16). Raffinose and sucrose are identified as non significant factors but sucrose is retained in the model to preserve the hierarchical model (see FIG. 25). FIG. 26 suggests curvature in the model; however, the model was not improved by the inclusion of a $2^{nd}$ order interaction suggesting some other cause for the curvature.

Example 13

Materials

| Chemical | Supplier | Product Code | Lot No. |
|---|---|---|---|
| 20x SSC | Sigma | S6639 | 020M8404 |
| Dimethyl glycine | Sigma | D1156 | 077K1856 |
| Dulbeccos Modified Eagles Medium | Sigma | D5796 | RNBB1139 |
| Foetal Bovine Serum | Sigma | F7524 | 109K3395 |
| Penicillin Streptomycin | Sigma | P4458 | 0409M0093 |
| Raffinose | Sigma | R0250 | 050M0053 |
| Sucrose | Sigma | 16104 | SZB90120 |
| Water | Sigma | W3500 | 8M0411 |

| Biological | Supplier | Product Code |
|---|---|---|
| Adenovirus | Vector Biolabs | Ad-CMV-GFP |
| HEK 293 | ECACC | 85120602 |

| Other | Manufacturer | Product Code |
|---|---|---|
| 2 ml glass vials | Adelphi Tubes | VCDIN2R |
| 13 mm freeze drying stoppers | Adelphi Tubes | FDW13 |
| Crimps | Adelphi Tubes | COTW13 |

Equipment

| | Manufacturer | Equipment No. |
|---|---|---|
| Virtis Advantage Plus EL85 Freeze Dryer | Virtis | EQP#084 |
| HERASAFE ™ class II | Thermo Fisher | EQP# 011 & 012 cabinet |
| DMIL LED Inverted Microscope | Leica | EQP#062 |
| Binder CO$_2$ Incubator | Binder | EQP#014 |
| Forma 900 series −80° C. freezer | Thermofisher | EQP#015 |
| ATL-84-1 Atlion Balance | Acculab | EQP#088 |
| IP250 37° C. Incubator | LTE | EQP#016 |

Methods
Design of Experiment

Figure 27:
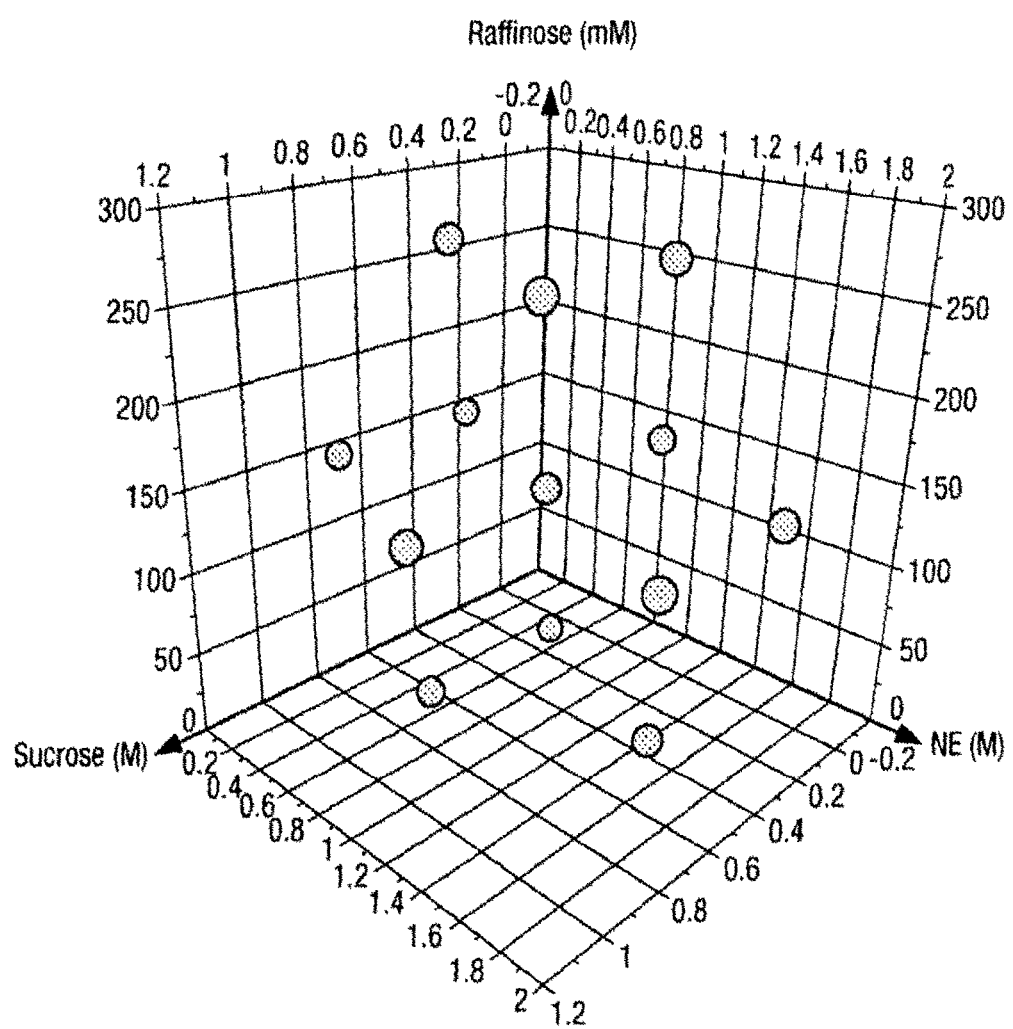
FIG. 27 shows a 3D representation of the design space in Example 13. Spheres represent formulations within the design space that were tested. This design is a Doehlert RSM design.

MODDE 9.0 (Umetrics) was used to generate a Doehlert experimental design (see FIG. 27). Doehlert designs are response surface modelling designs constructed from regular simplexes. They are easily extendable in different directions and new factors can be added to an existing design. Unlike regular formulation designs non-significant factors can be eliminated from the analysis and so do not become a confounding factor. Furthermore, different factors within the design are tested at a different number of levels, so it is possible to allocate more test levels to factors that are suspected of greater importance. Thus the excipients were tested at 7 levels, whilst sucrose was tested at 5 levels and raffinose at only 3 levels. This model retains the ability to model for second order effects and interactions. The design included 3 factors and 3 replicate centre-points resulting in 15 test samples.

Sucrose was tested between 0 and 1M. The upper level of sucrose was set at 1M because it has proved close to the limit for acceptable freeze-drying. It has also proved to be a highly successful level in prior studies, and in general higher sucrose concentrations are undesirable in parenterals. The lowest level of Sucrose was set at 0 M Raffinose was tested over a range of 0 to 300 mM although the nature of the Doehlert design meant that tested levels did not include 0 mM, instead the following concentrations were tested; 27.5, 150.0, and 272.5 mM.

DMG was tested over a linear range of 0 to 2M. It was possible to limit this range based on previous experiments in which the optimum concentration was frequently between 0.5 and 1.5M in a freeze-dried setting.

Stability of Adenovirus in a Freeze-Dried Setting
Preparation of and Thermal Challenge of Formulated Adenovirus in a Freeze-Dried Setting Recombinant Adenovirus expressing enhanced GFP under a CMV promoter, with a titre (pre-freeze) of $6.7 \times 10^5$ pfu/ml in SSC, was removed from storage at −80° C. and allowed to thaw. Subsequently, 50 μl aliquots of virus were added to 15, 2 ml, glass freeze-drying vials. To each vial 250 μl of an excipient blend was admixed. The excipient blend formulations once mixed with virus are described in Table 18 and were made up in SSC.

TABLE 18

| Formulation No. | Sucrose (M) | Raffinose (mM) | DMG (M) | Titre (pfu/ml) |
|---|---|---|---|---|
| 1 | 0.25 | 150.0 | 0.13 | 4.8E+04 |
| 2 | 0.75 | 150.0 | 0.13 | 1.3E+05 |
| 3 | 0.5 | 272.5 | 0.42 | 3.0E+05 |
| 4 | 0.25 | 27.5 | 0.71 | 2.2E+05 |
| 5 | 0.75 | 27.5 | 0.71 | 3.1E+05 |
| 6 | 0 | 150.0 | 1.00 | 3.1E+05 |
| 7 | 0.5 | 150.0 | 1.00 | 5.2E+05 |
| 8 | 0.5 | 150.0 | 1.00 | 3.7E+05 |
| 9 | 0.5 | 150.0 | 1.00 | 4.6E+05 |
| 10 | 1 | 150.0 | 1.00 | 4.7E+05 |
| 11 | 0.25 | 272.5 | 1.29 | 3.1E+05 |
| 12 | 0.75 | 272.5 | 1.29 | 3.3E+05 |
| 13 | 0.5 | 27.5 | 1.58 | 4.4E+05 |
| 14 | 0.25 | 150.0 | 1.87 | 1.4E+05 |
| 15 | 0.75 | 150.0 | 1.87 | 2.5E+05 |

Rubber bungs were partially inserted, and after vortexing were loaded onto a Virtis advantage freeze-dryer and lyophilised on program 4 (see FIG. 28). After lyophilisation samples were immediately capped under vacuum, removed, crimped and placed at 37° C. for thermal challenge. Thermal challenge was for 7 days, after which all the vials were held at 4° C. until it was practical to assay them. Freeze-dried samples were reconstituted in 300 μl SSC immediately prior to assay.

Assay of Adenovirus

HEK 293 cells were prepared in 96 well flat bottomed cell culture dishes for inoculation by seeding at $10^5$ cells per ml (100 μl per well) and maintained at 37° C. with 5% CO$_2$. After 2 hours cells were inoculated as follows.

Thermo-challenged virus samples were diluted 1 in 10, and 1 in 100 in DMEM +10% FBS. 100 μl of each of the resulting diluted virus samples were then added to individual wells of the assay plate. Additionally, a second aliquot of the original Adenovirus in SSC was thawed from −80° C. and a 10 fold dilution series (from 1 in 10 to 1 in 100,000) also prepared in DMEM+10% FBS. Two repeats of this positive control dilution series was inoculated to each 96 well plate used. After a further 48 hours, the number of GFP cells per well were counted using fluorescent microscopy.

Results

Figure 29:
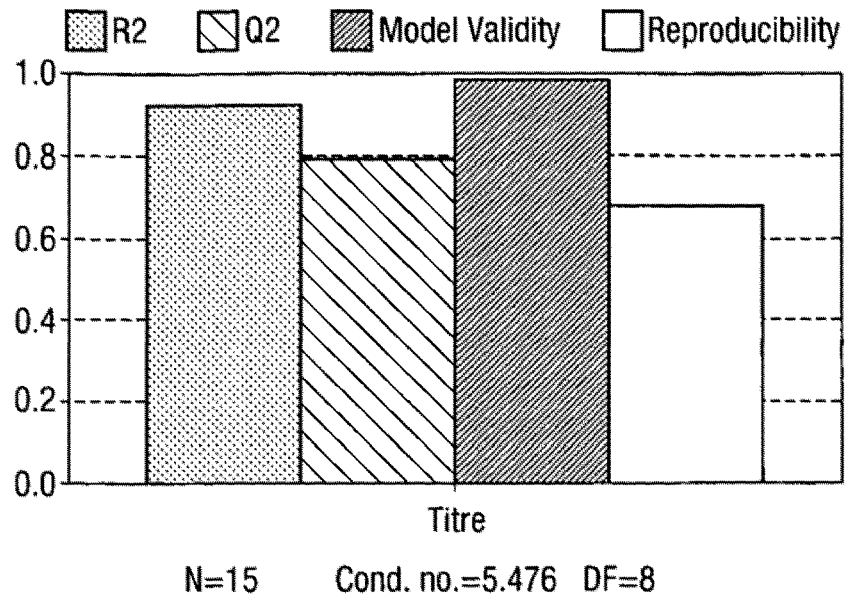
FIG. 29 summarises various statistics for the model derived from the data in Example 13.

A strong model was produced in which all four indicators suggested good significance (R2=0.93, Q2=0.79, Model Validity=0.98, Reproducability=0.68) (see FIG. 29). Of these the figure for reproducibility is the only one that is slightly low, although it is well above 0.5. The reason for this value being slightly lower than has been customary could be the slightly higher variation between the replicated centrepoints or rather the level of variation between these is proportionally larger compared to the overall variation in the assay.

Figure 30:
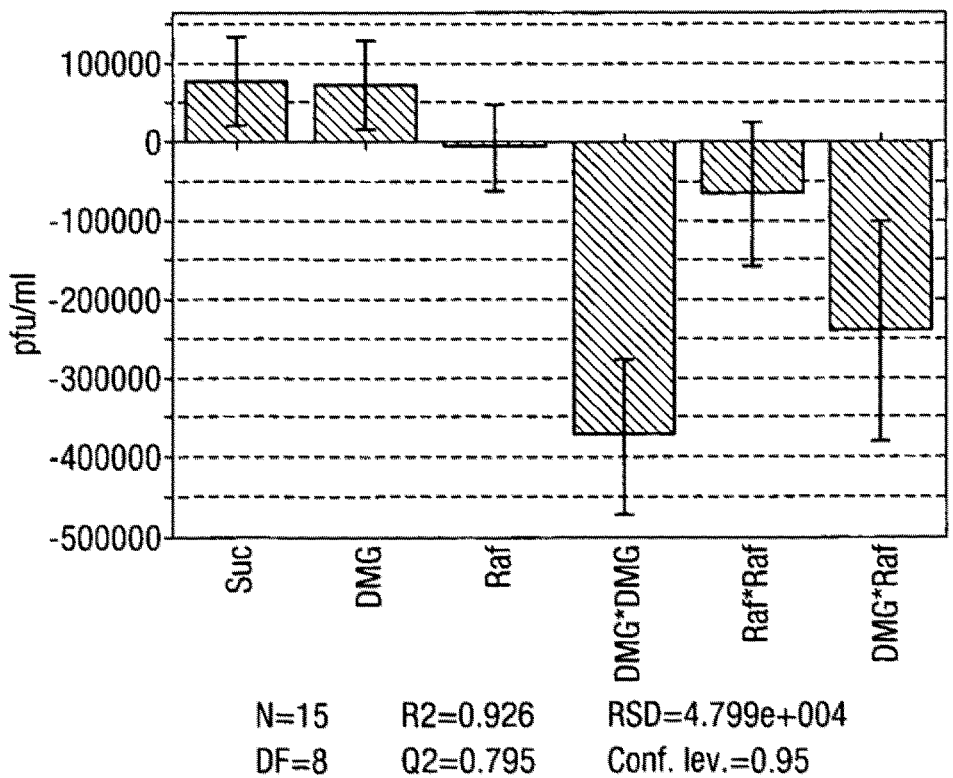
FIG. 30 shows terms retained in the model in Example 13 after fine tuning. Error bars not crossing the origin indicate a significant factor at the 95% C.I.

The model identified (see FIG. 30) 1st order effects of both sucrose and DMG as well as a 2nd order effect of DMG. No 1st or 2nd order effects of raffinose were observed. However, raffinose does have an interaction with DMG and thus the 1st order raffinose coefficient must be retained in the model to preserve the models hierarchical structure. Furthermore, the 2nd order raffinose effect was retained as it resulted in a stronger model (as assessed by the indicators shown in FIG. 29 and discussed above). In any case the 2nd order raffinose effect was close to significance at the 90% C.I. and may be a genuine effect that simply cannot be conclusively detected over the range tested.

Figure 31:
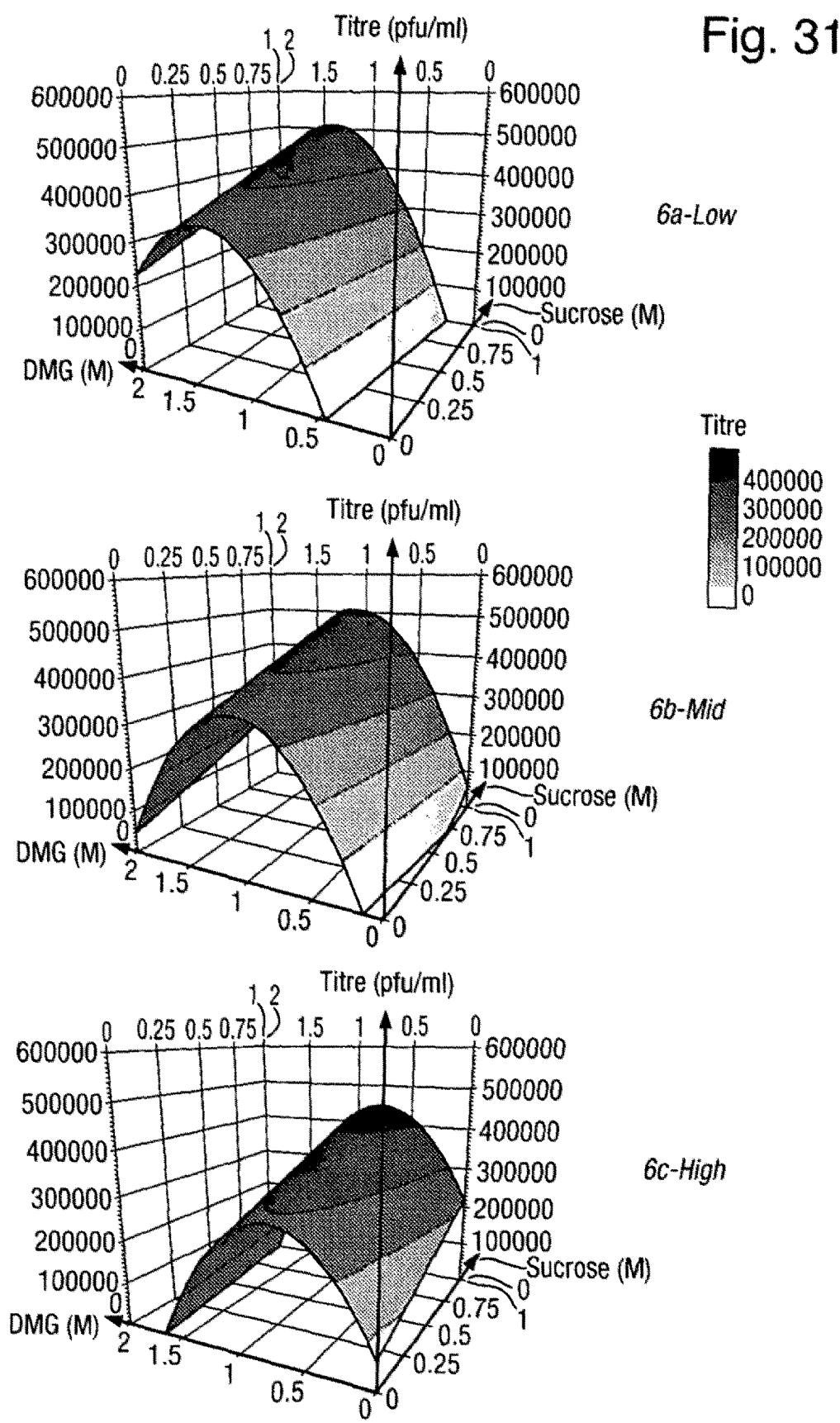
FIG. 31 shows a surface response plot of predicted viral titre in formulations of DMG and sucrose using the model in Example 13 at three different levels of raffinose—"Low"=raffinose at 0 mM, "Mid"=raffinose at 150 mM, "High"=raffinose at 300 mM.

FIG. 31 shows a series of 3D plots of recovered virus activity (Y-Axis) against varied sucrose (X-axis) and DMG (Z-axis) concentrations. "Low" denotes a raffinose concentration of 0 mM, "Mid" denotes a raffinose concentration of 150 mM and "High" denotes a raffinose concentration of 300 mM.

Each plot shows the model at a different and static raffinose concentration. Improved preservation of adenovirus is achieved by increasing sucrose concentration. This trend continues beyond the tested range the experiment is unable to identify a true sucrose optimum. In contrast, the optimum DMG concentration is clearly within the tested range. Increasing Raffinose concentration appears to decrease the optimum DMG concentration.

Figure 32:
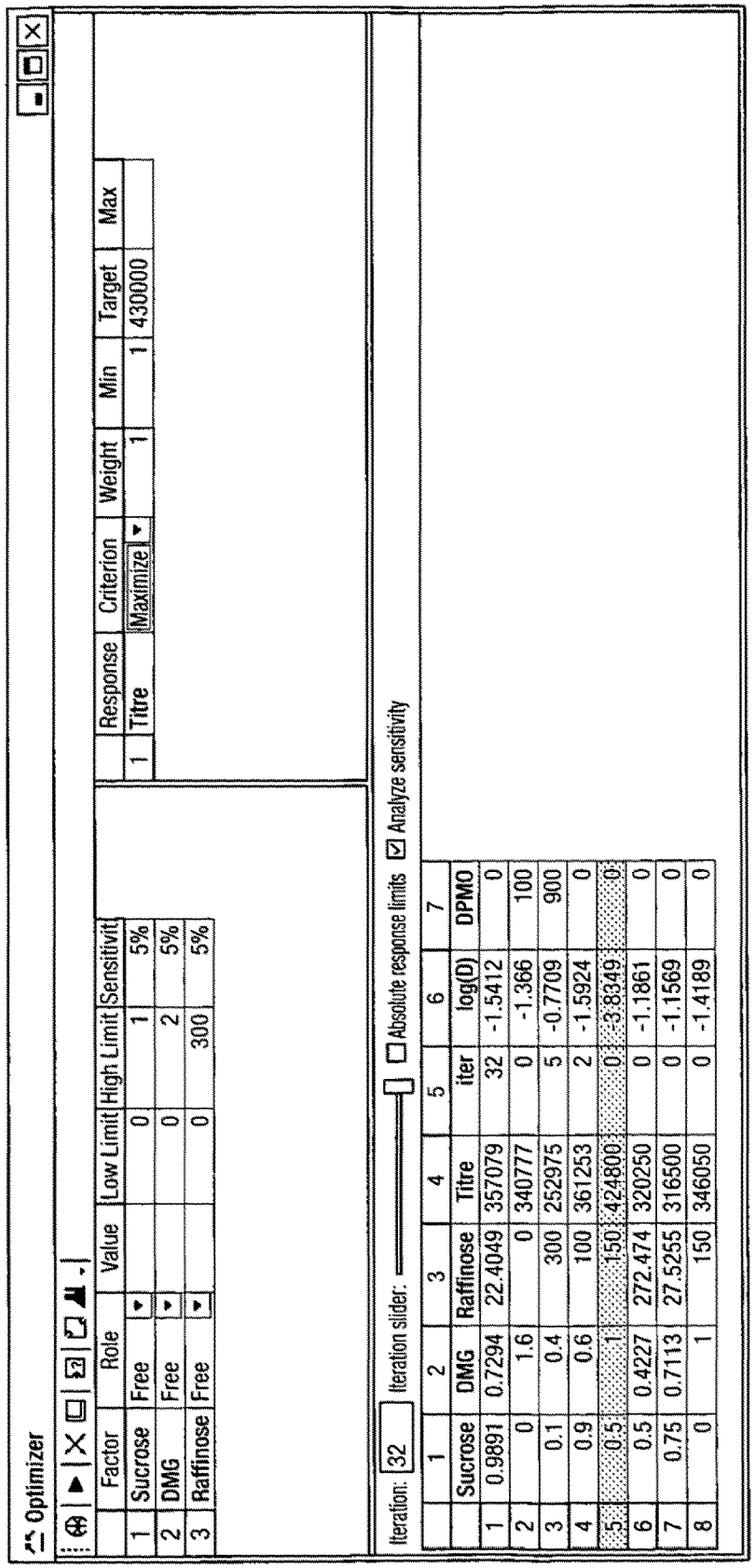
FIG. 32 shows the settings and outputs from an optimum prediction based on the model of the data in Example 13 generated using Monte-Carlo simulations. The predicted optima highlighted in this model are concentrations of sucrose=0.5M, DMG=1M, raffinose=150 mM.

Monte-Carlo simulations were used to predict an optimal formulation (see FIG. 32). An optimum of 0.5M Sucrose, 1M DMG, 150 mM Raffinose was predicted to yield a recovered virus titre of $4.2 \times 10^5$ pfu/ml or 98% of that input before thermal challenge (based on a positive control which had a titre of $4.3 \times 10^5$ pfu/ml).

Figure 33A:
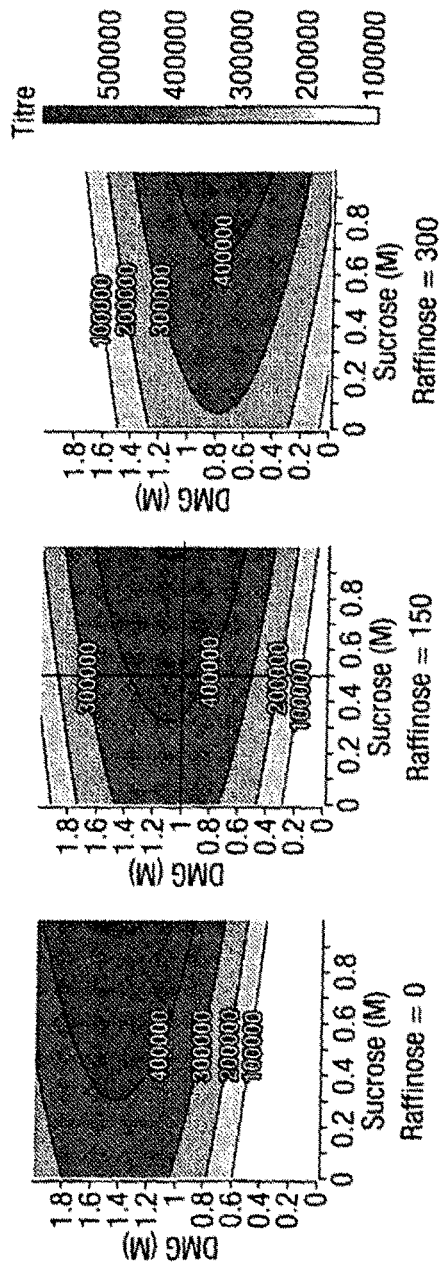
FIGS. 33A and 33B show an optimum region plot from the Example 13 data. The plots are at static raffinose levels=0, 150, 272, 300 mM. The variable plotted is recovered titre (pfu/ml).
Figure 33B:
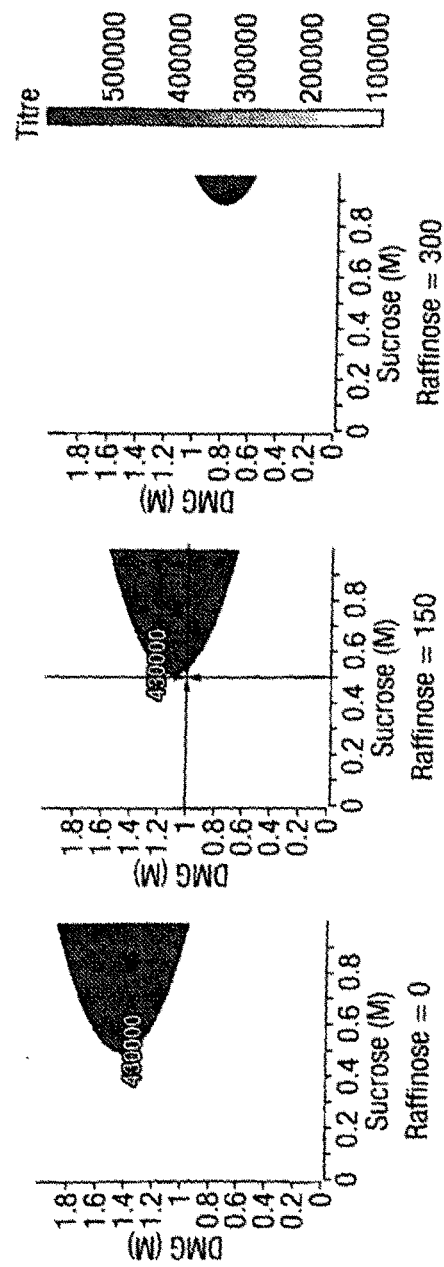

The predicted optimum is shown on a contour plot (FIG. 33a) which puts the optimum into context. The model predicts whole regions of the design space in which formulations would yield 100% or greater recovered virus activity. This region needs to be viewed as a plateau in the data within which close to zero loss of virus activity would be expected. FIG. 33b highlights this region. The figure shows that as raffinose concentration is increased the region moves down the Y-axis (DMG concentration) and up the X-axis (sucrose concentration).

Conclusions

A formulation of DMG, sucrose and raffinose has been identified with significant potential for the preservation of adenovirus through lyophilisation and heat challenge. Models based on the data predict that recovery of 100% of viral activity is possible. This model, an optimum DMG concentration of between 0.5 and 1.5M was identified. The optimum sucrose concentration is beyond the tested range and also likely beyond other constraints of sucrose concentration. Raffinose does not appear to be a critical factor in this model.

Example 14

Materials

| Chemical | Supplier | Product Code | Lot No. |
|---|---|---|---|
| 20x SSC | Sigma | S6639 | 020M8404 |
| Dimethyl glycine | Sigma | D1156 | 077K1856 |
| Dulbeccos Modified Eagles Medium | Sigma | D5796 | RNBB1139 |
| Foetal Bovine Serum | Sigma | F7524 | 109K3395 |
| Penicillin Streptomycin | Sigma | P4458 | 0409M0093 |
| Raffinose | Sigma | R0250 | 050M0053 |
| Sucrose | Sigma | 16104 | SZB90120 |
| Water | Sigma | W3500 | 8M0411 |

| Biological | | |
|---|---|---|
| | Supplier | Product Code |
| Adenovirus | Vector Biolabs | Ad-CMV-GFP |
| HEK 293 | ECACC | 85120602 |

| Other | | |
|---|---|---|
| | Manufacturer | Product Code |
| 2 ml glass vials | Adelphi Tubes | VCDIN2R |
| 13 mm freeze drying stoppers | Adelphi Tubes | FDW13 |
| Crimps | Adelphi Tubes | COTW13 |

Equipment

| | Manufacturer | Equipment No. |
|---|---|---|
| Virtis Advantage Plus EL85 Freeze Dryer | Virtis | EQP#084 |
| HERASAFE ™ class II | Thermo Fisher | EQP# 011 & 012 cabinet |
| DMIL LED Inverted Microscope | Leica | EQP#062 |
| Binder $CO_2$ Incubator | Binder | EQP#014 |
| Forma 900 series −80° C. freezer | Thermofisher | EQP#015 |
| ATL-84-1 Atlion Balance | Acculab | EQP#088 |
| IP250 +37° C. Incubator | LTE | EQP#016 |
| +4° C. long term sample fridge | LEC | EQP#090 |
| KB115 +25° C. incubator | Binder | EQP#008 |

Design of Experiment

A long term stability study was planned to test putative optimal formulation of DMG, sucrose and raffinose for adenovirus in a lyophilised setting. Three formulations were tested:

Adenovirus in SSC buffer alone;

Adenovirus in 0.5M sucrose and 150 mM raffinose in SSC; and

Adenovirus in 0.5M sucrose, 150 mM raffinose and 1M DMG also in SSC.

A long-term stability testing temperature of +4° C.±3 was selected. This is broadly consistent with standard industry guidelines for long-term testing of products intended for refrigerated storage (+5° C.±3). An accelerated stability temperature of +25° C. was adopted and a thermal challenge of +37° C. was adopted to represent a stress testing temperature, or a further elevated accelerated thermal stability temperature.

The samples at 25° C. and 37° C. were tested 1, 2, 5 and 15 weeks post lyophilisation. The samples at +4° C. were tested at 15 weeks post lyophilisation.

Preparation of and Thermal Challenge of Formulated Adenovirus in a Freeze-Dried Setting Recombinant adenovirus expressing enhanced GFP under a CMV promoter, with a titre (pre-freeze) of $6.7 \times 10^5$ pfu/ml in SSC, was removed from storage at −80° C. and allowed to thaw. Subsequently, 50 μl aliquots of virus were added to 2 ml glass freeze-drying vials. To each vial 250 μl of an excipient blend was admixed. The excipient blend formulations used were as described above, namely (i) buffer alone (SSC), (ii) sugars (0.5M Sucrose, 150 mM Raffinose in SSC), and (iii) a putative optimal formulation (0.5M Sucrose, 150 mM Raffinose, 1M DMG, also in SSC).

Rubber bungs were partially inserted, and after vortexing were loaded onto a VirTis Advantage Freeze Dryer and lyophilised on program 1 (see FIG. 34). After lyophilisation samples were immediately capped under vacuum, removed, crimped, and divided between the three thermal treatments. Subsequently, at each time point 2 vials of each formulation were recovered according to the schedule above and reconstituted in 300 µl SSC immediately prior to assay.

Assay of Adenovirus

HEK 293 cells were prepared in 96 well flat bottomed cell culture dishes for inoculation by seeding at $10^5$ cells per ml (100 µl per well) and maintained at 37° C. with 5% $CO_2$. After 2 hours cells were inoculated as follows.

Thermo-challenged virus samples were recovered from thermo challenge as described above diluted 1 in 10, and 1 in 100 in DMEM+10% FBS. 100 µl of each of the resulting diluted virus samples were then added to individual wells of the assay plate.

Additionally, a second aliquot of the original adenovirus in SSC was thawed from −80° C. and a 10 fold dilution series (from 1 in 10 to 1 in 100,000) also prepared in DMEM+10% FBS. Two repeats of this positive control dilution series was inoculated to each 96 well plate used. After a further 48 hours, the number of GFP cells per well were counted using fluorescent microscopy.

Results

Figure 35:
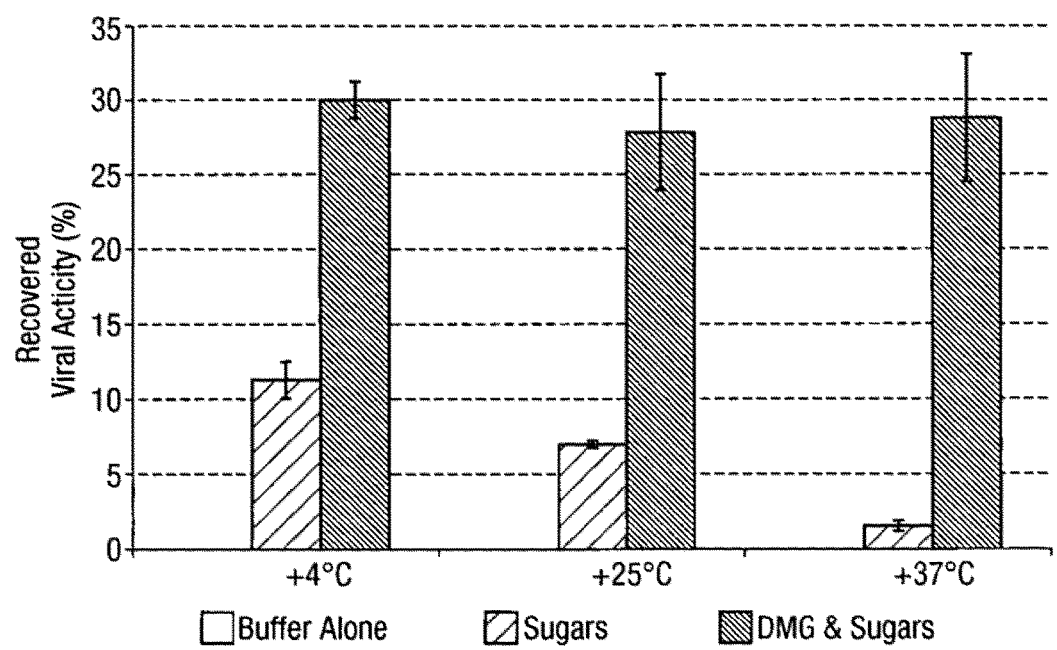
FIG. 35 shows recovered virus activity in Example 14 as a percentage of starting titre at week 15 post lyophilisation. Error bars are standard error of the mean (n=2).

At 15 weeks, (see FIG. 35) no virus activity was recovered from samples formulated in buffer alone (SSC). Formulation with sugars prevents some of this loss. However, only in those samples stored at +4° C. are losses less than a full log drop i.e, recovered activities over 10% of starting titre. In this treatment at this time point losses are progressively worse with increasing temperature. Since elevated temperature is a standard mode of simulating longer thermal stability studies (accelerated stability) it is suggested that the losses in sugars have not reached endpoint at +4° C. and that further losses over time can be expected.

Using the putative optimum formulation losses are further reduced. In fact at all three storage temperatures losses are around a half log loss (33% recovered activity). The responses at all three temperatures are between 27.84 and 30.00% recovery which represent a loss of 0.52-0.54 Logs. There does not appear to be significant differences between the three temperatures (+4° C., 25° C. and +37° C.) with this formulation. This implies that either (a) the degradation has reached end-point and no further degradation over time can be expected, or (b) that the rate of decline has become so slow that the difference in the accelerated temperature studies cannot be detected.

Figure 36:
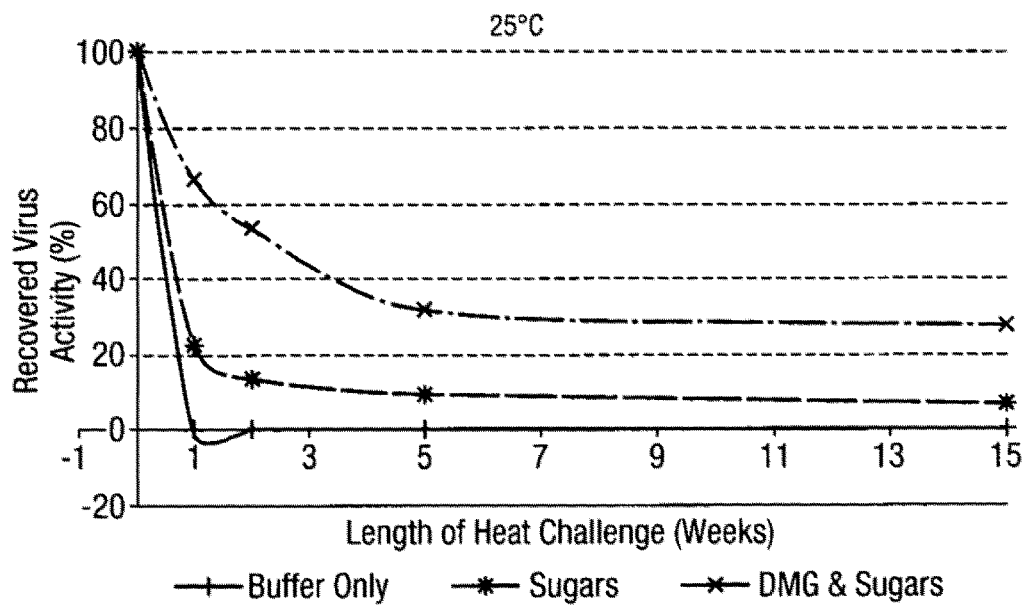
FIG. 36 shows recovered virus activity over time at the accelerated stability temperature (+25° C.) in Example 14.
Figure 37:
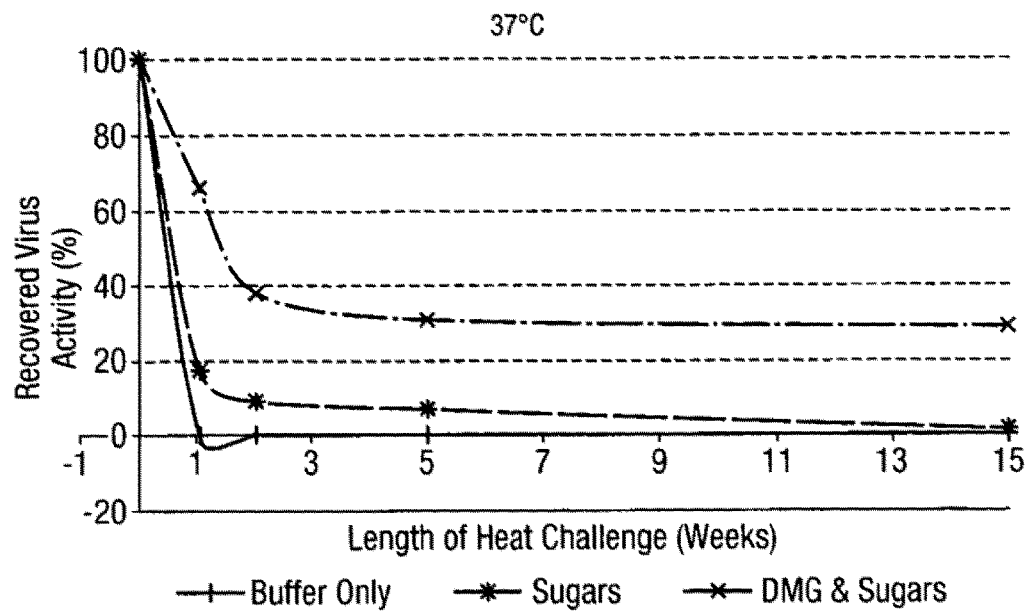
FIG. 37 shows recovered virus activity over time at the stress testing temperature (+37° C.) in Example 14.

FIGS. 36 and 37 further support these findings. At both, +25° C. and +37° C., no virus activity is recovered from samples stored in buffer alone at any time-point. Those formulated in sugars alone retain some activity throughout. Their activity declines by a slightly greater degree and slightly more rapidly at the higher temperature (+37° C.). In the putative optimal formulation there is a steeper decline in viral activity at +37° C. but both temperatures decline to similar levels over time.

At both +25° C. and +37° C. with all the formulations tested the majority of the decline in virus activity occurs between t=0 and t=5 weeks. In fact, in the case of buffer alone and sugar formulations the vast majority of degradation occurs between t=0 and t=1 week. The value of the response used as t=0 was the titre of the virus prior to lyophilisation and thermal challenge whereas the time-points are plotted as weeks post thermal challenge. Consequently, the observed differences between and t=1 week are the sum of degradation during lyophilisation and during the first week of thermal challenge.

Example 15

Materials

| Chemical | | | |
|---|---|---|---|
| | Supplier | Product Code | Lot No. |
| 20x SSC | Sigma | S6639 | 020M8404 |
| Dulbeccos Modified Eagles Medium | Sigma | D5796 | RNBB1139 |
| Foetal Bovine Serum | Sigma | F7524 | 109K3395 |
| Penicillin Streptomycin | Sigma | P4458 | 0409M0093 |
| Trimethyl glycine | Sigma | | |
| Water | Sigma | W3500 | 8M0411 |

| Biological | | |
|---|---|---|
| | Supplier | Product Code |
| BHK-21 cell line | ECACC | CB2857 |
| MVA | ATCC | VR-1508 |

| Other | | |
|---|---|---|
| | Manufacturer | Product Code |
| 2 ml glass vials | Adelphi Tubes | VCDIN2R |
| 13 mm freeze drying stoppers | Adelphi Tubes | FDW13 |
| Crimps | Adelphi Tubes | COTW13 |

Equipment

| | Manufacturer | Equipment No. |
|---|---|---|
| Virtis Advantage Plus EL85 Freeze Dryer | Virtis | EQP#096 |
| HERASAFE ™ class II | Thermo Fisher | EQP# 011 & 012 cabinet |
| DMIL LED Inverted Microscope | Leica | EQP#062 |
| Binder $CO_2$ Incubator | Binder | EQP#014 |
| Forma 900 series −80° C. freezer | Thermofisher | EQP#015 |
| ATL-84-1 Atlion Balance | Acculab | EQP#088 |
| IP250 37° C. Incubator | LTE | EQP#016 |

Methods

Design of Experiment

Figure 38:
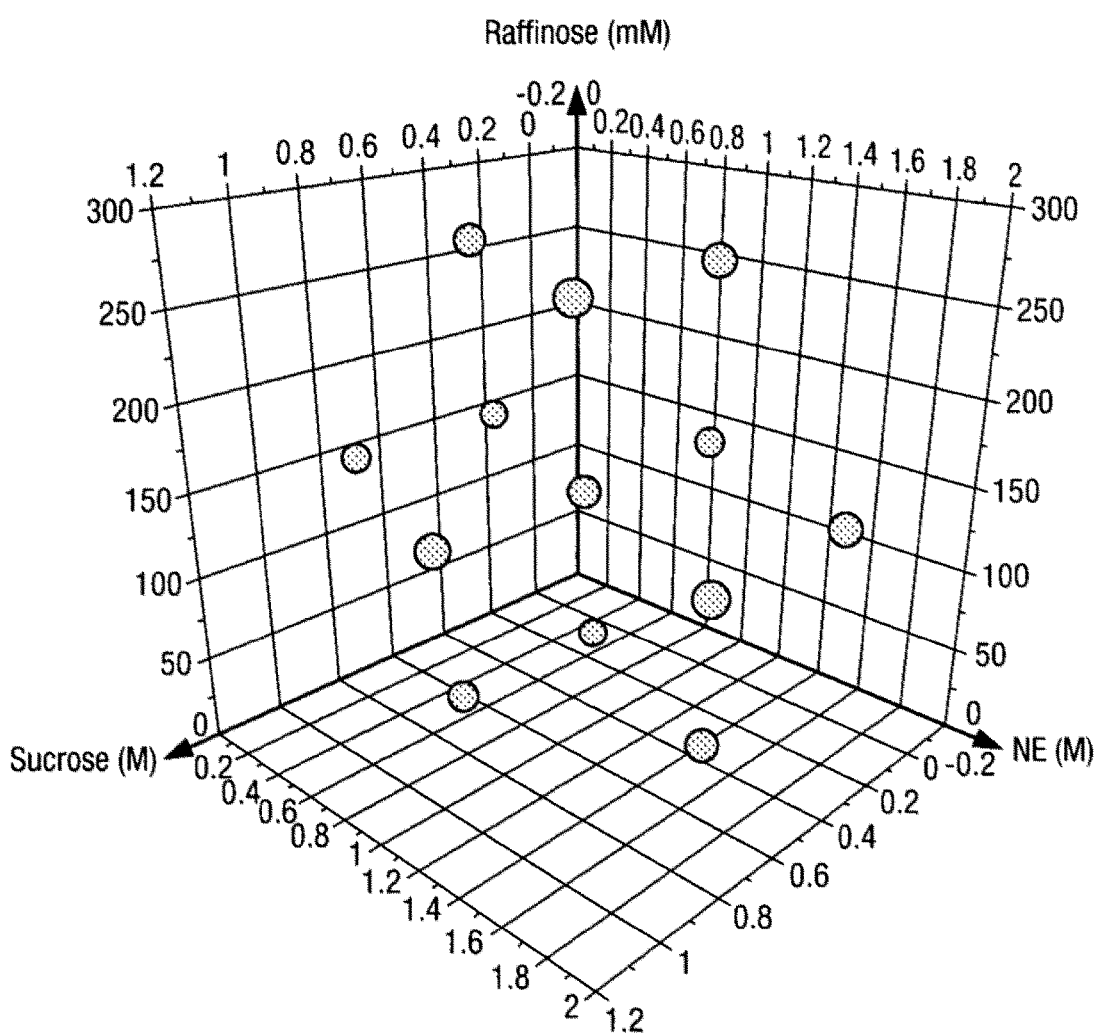
FIG. 38 shows a 3D representation of the design space in Example 15. Spheres represent formulations within the design space that are tested. This design is a Doehlert RSM design.

MODDE 9.0 (Umetrics) was used to generate a Doehlert experimental design (see FIG. 38), as described in Example 13. Thus, TMG was tested at seven levels, whilst sucrose was tested at five and raffinose three. This model retains the ability to model for second order effects and interactions. The design included three factors and three replicate centre-points resulting in fifteen test samples.

Sucrose was tested between 0 and 1M. Raffinose was tested over a range of 0 to 300 mM, although the nature of the Doehlert design meant that tested levels did not include 0 mM. Instead the following ranges were tested: 27.5, 150.0, and 272.5 mM. TMG was tested over a linear range of 0 to 2M.

Preparation of and Thermal Challenge of Formulated MVA in a Freeze-Dried Setting MVA was recovered from storage at −80° C. and thawed. 50 µl aliquots of the MVA were added to 2 ml, glass freeze-drying vials, subsequently 250 µl of an excipient blend was added to each vial. The excipient blend formulations once mixed with virus are described in Table 19 and were made up in SSC.

TABLE 19

| Formulation No. | Sucrose (M) | Raffinose (mM) | TMG (M) | Titre (pfu/ml) |
|---|---|---|---|---|
| 1 | 0.25 | 150.0 | 0.13 | 1.1E+05 |
| 2 | 0.75 | 150.0 | 0.13 | 7.6E+04 |
| 3 | 0.5 | 272.5 | 0.42 | 1.7E+05 |
| 4 | 0.25 | 27.5 | 0.71 | 4.8E+05 |
| 5 | 0.75 | 27.5 | 0.71 | 7.6E+05 |
| 6 | 0 | 150.0 | 1.00 | 4.8E+05 |
| 7 | 0.5 | 150.0 | 1.00 | 7.6E+05 |
| 8 | 0.5 | 150.0 | 1.00 | 7.6E+05 |
| 9 | 0.5 | 150.0 | 1.00 | 7.6E+05 |
| 10 | 1 | 150.0 | 1.00 | 1.2E+06 |
| 11 | 0.25 | 272.5 | 1.29 | 4.8E+05 |
| 12 | 0.75 | 272.5 | 1.29 | 7.6E+05 |
| 13 | 0.5 | 27.5 | 1.58 | 3.0E+05 |
| 14 | 0.25 | 150.0 | 1.87 | 7.6E+05* |
| 15 | 0.75 | 150.0 | 1.87 | 3.0E+05 |

*indicates an outlier eliminated from the model

Rubber bungs were partially inserted, and after vortexing were loaded onto a Virtis advantage freeze-dryer and lyophilised as described in FIG. 39. After lyophilisation samples were immediately capped under vacuum, removed, crimped and placed at 37° C. for thermal challenge. Thermal challenge was for 7 days, after which all the vials were returned to the control vials and held at 4° C. until it was practical to assay them. Freeze-dried samples were reconstituted in 300 µl SSC immediately prior to assay.

Assay of MVA

Assay plates (96 well) were seeded with BHK-21 cells (100 µl per well, $10^5$ cells/ml). Cells were diluted in DMEM supplemented with 10% FBS, and 1% PS. The plates were placed at +37° C., +5% $CO_2$ for 1-2 hours.

Meanwhile, a 10 fold dilution series of the formulated MVA samples was prepared (in the same growth media) ranging from 1 in 10 to 1 in 10,000. Each dilution series was prepared 5 times. 100 µl of each dilution was applied to individual wells containing BHK-21 cells (described above).

On 6 d p.i. the wells were scored for presence or absence of CPE and $TCID_{50}$ calculated. These were then used to estimate the concentration of infectious MVA per ml in the thermo-challenged vials.

Results

The data from this study is shown in Table 19. Responses varied from 6 to 92% of starting titre. During analysis, formulation number 14 was identified as an obvious outlier and excluded from this analysis. This enhanced model assessment parameters.

Figure 40:
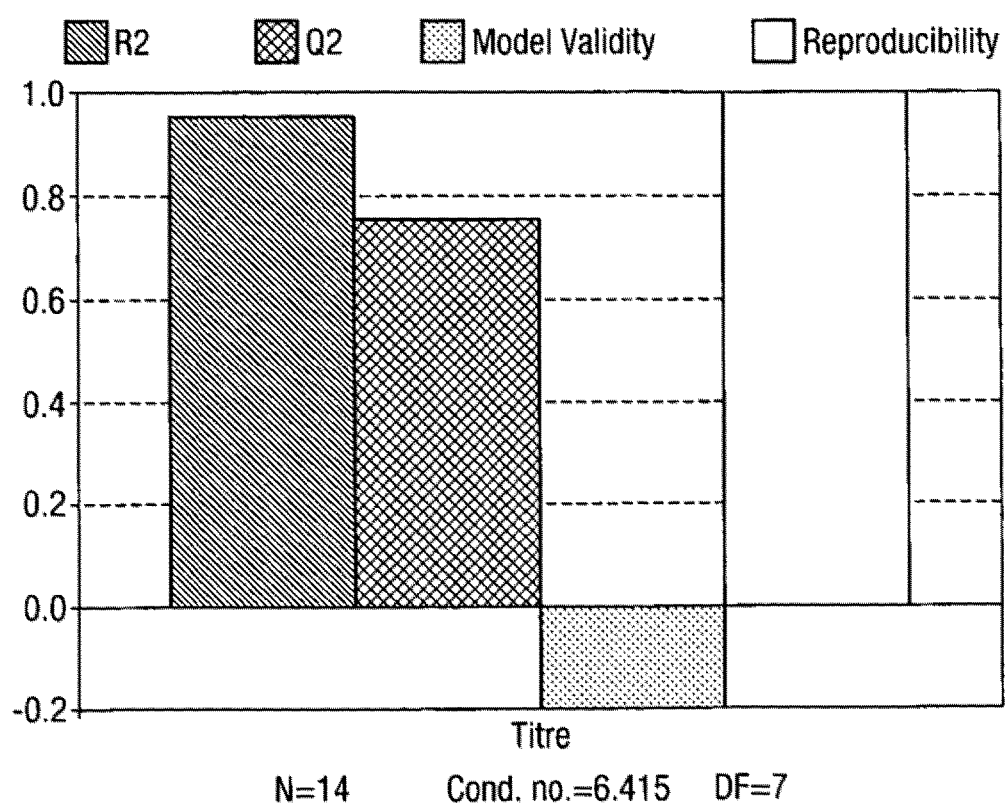
FIG. 40 summarises the statistics of the model in Example 15 used to represent the data.
Figure 41:
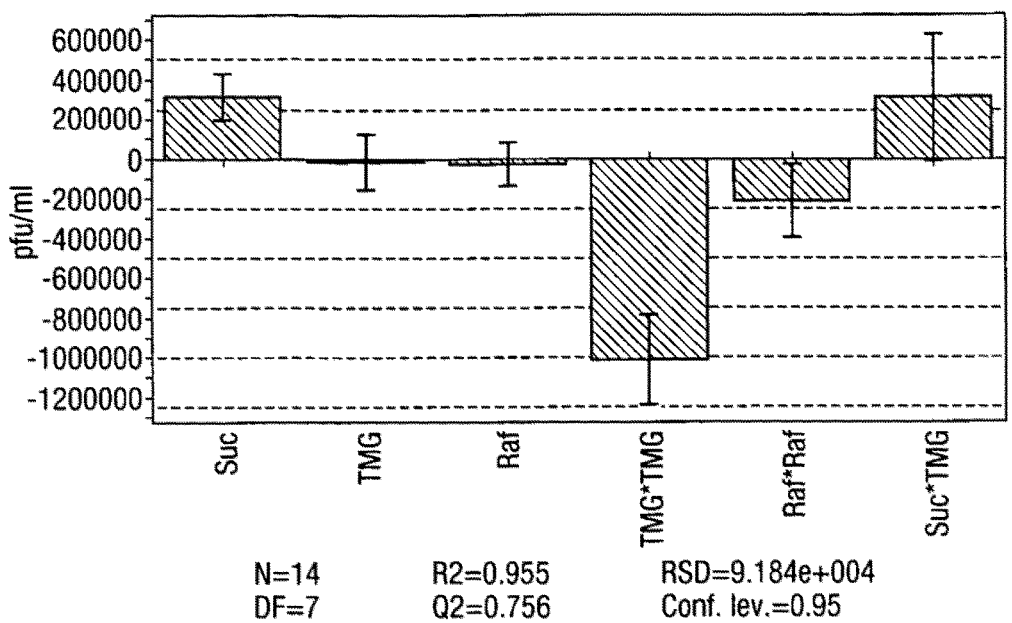
FIG. 41 shows terms retained in the model in Example 15 after fine tuning. Error bars not crossing the origin indicate a significant factor at the 95% C.I.

The model reported here (see FIGS. 40 and 41) demonstrates a $1^{st}$ order effect for sucrose. Raffinose was found to have no $1^{st}$ order effect but did demonstrate a $2^{nd}$ order interaction. TMG was not found to have a $1^{st}$ order effect in this study but a $2^{nd}$ order effect was identified. Finally, an interaction between sucrose and TMG was identified.

Figure 42:
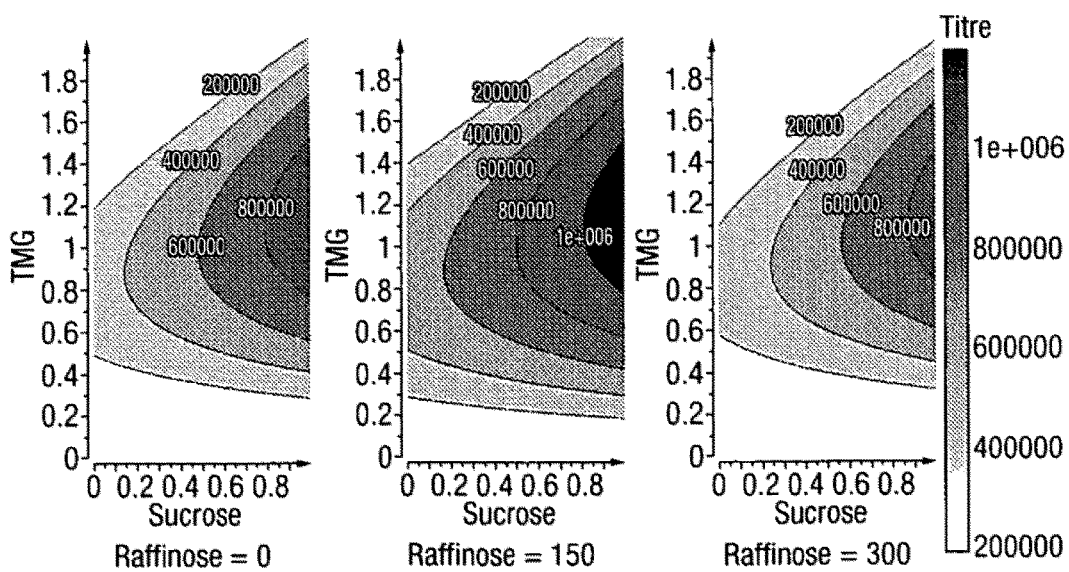
FIG. 42 shows contours plot of recovered viral titre (TCID50/ml) with varying formulations in Example 15.

FIG. 42 shows a contour plot of the model. The optimum TMG concentration is close to the centre of the model (around 1M), although this drifts slightly as you vary the other excipients. Raffinose also shows an optimum. Finally, as a general rule, the higher the sucrose concentration the better the preservation of MVA.

Monte-Carlo simulations identified an optimum of 1M sucrose, 1.14M TMG and 141.76 mM raffinose and gave a predicted recovery of $1.14 \times 10^6$ pfu/ml or 87.7% of starting titre.

Example 16

Materials

| Chemical | | | |
|---|---|---|---|
| | Supplier | Product Code | Lot No. |
| 20x SSC | Sigma | S6639 | 020M8404 |
| Dimethyl glycine | Sigma | D1156 | 077K1856 |
| Dulbeccos Modified Eagles Medium | Sigma | D5796 | RNBB1139 |
| Foetal Bovine Serum | Sigma | F7524 | 109K3395 |
| Penicillin Streptomycin | Sigma | P4458 | 0409M0093 |
| Water | Sigma | W3500 | 8M0411 |

| Biological | | |
|---|---|---|
| | Supplier | Product Code |
| BHK-21 cell line | ECACC | CB2857 |
| MVA | ATCC | VR-1508 |

| Other | | |
|---|---|---|
| | Manufacturer | Product Code |
| 2 ml glass vials | Adelphi Tubes | VCDIN2R |
| 13 mm freeze drying stoppers | Adelphi Tubes | FDW13 |
| Crimps | Adelphi Tubes | COTW13 |

Equipment

| | Manufacturer | Equipment No. |
|---|---|---|
| Virtis Advantage Plus EL85 Freeze Dryer | Virtis | EQP#096 |
| HERASAFE ™ class II | Thermo Fisher | EQP# 011 & 012 cabinet |
| DMIL LED Inverted Microscope | Leica | EQP#062 |
| Binder $CO_2$ Incubator | Binder | EQP#014 |
| Forma 900 series −80° C. freezer | Thermofisher | EQP#015 |
| ATL-84-1 Atlion Balance | Acculab | EQP#088 |
| IP250 37° C. Incubator | LTE | EQP#016 |

Methods

Figure 43:
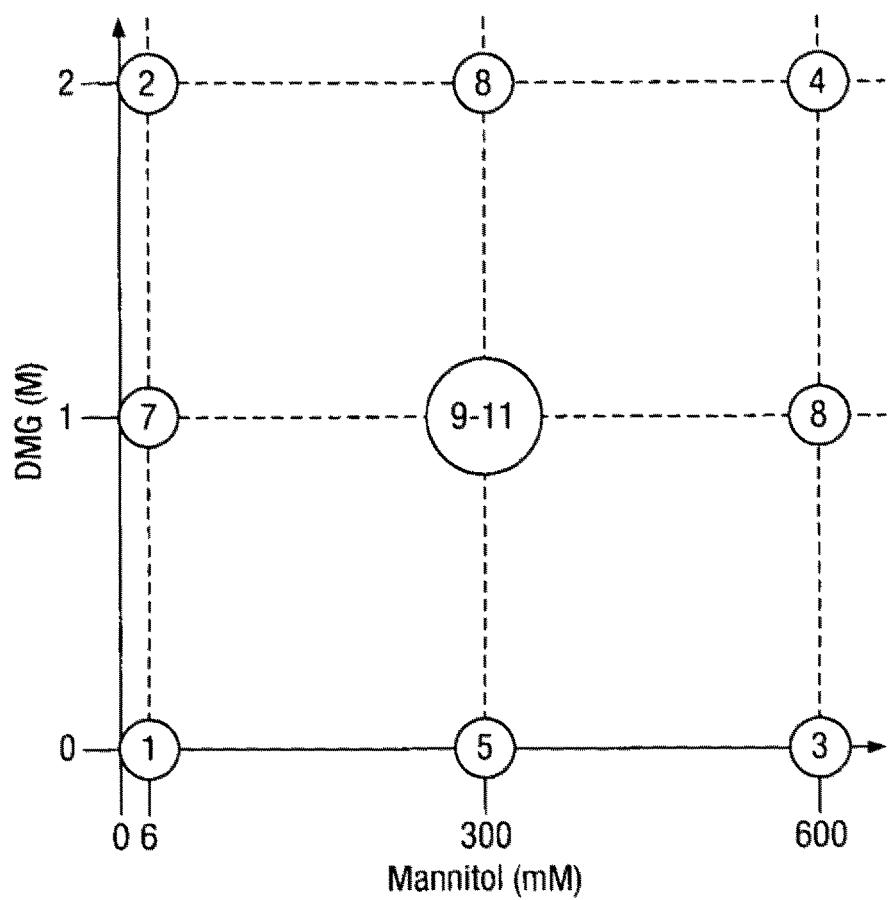
FIG. 43 shows a representation of the design space in Example 16. Numbered circles represent formulations within the design space that are tested.

MODDE 9.0 was used to generate a Central Composite Face-Centred (CCF) design (see FIG. 43). CCF designs are a form of Response Surface Modelling (RSM) design that tests only three levels of each factor but still supports a quadratic model. Unlike regular formulation designs, non-significant factors can be eliminated from the analysis and so do not become a confounding factor.

Preparation of and Thermal Challenge of Formulated MVA in a Freeze-Dried Setting MVA was recovered from storage at −80° C. and thawed. 50 µl aliquots of the MVA were added to 2 ml glass freeze-drying vials. Subsequently 250 µl of an excipient blend was added to each vial. The excipient blend formulations once mixed with virus are described in Table 20 and were made up in SSC.

TABLE 20

| Sample I.D. | DMG (M) | Mannitol (mM) | Titre (TCID50/ml) |
|---|---|---|---|
| 1 | 0 | 6 | 1.20E+5 |
| 2 | 2 | 6 | 3.00E+5 |
| 3 | 0 | 600 | 3.00E+5 |
| 4 | 2 | 600 | 1.90E+5 |
| 5 | 0 | 303 | 7.60E+5 |

TABLE 20-continued

| Sample I.D. | DMG (M) | Mannitol (mM) | Titre (TCID50/ml) |
|---|---|---|---|
| 6 | 2 | 303 | 1.90E+5 |
| 7 | 1 | 6 | 1.20E+6 |
| 8 | 1 | 600 | 1.20E+6 |
| 9 | 1 | 303 | 1.20E+6 |
| 10 | 1 | 303 | 1.20E+6 |
| 11 | 1 | 303 | 7.60E+5 |

Rubber bungs were partially inserted, and after vortexing were loaded onto a Virtis advantage freeze-dryer and lyophilised as described in FIG. 44. After lyophilisation samples were immediately capped under vacuum, removed, crimped and placed at 37° C. for thermal challenge. Thermal challenge was for 7 days, after which all the vials were returned to the control vials and held at 4° C. until it was practical to assay them. Freeze-dried samples were reconstituted in 300 μl SSC immediately prior to assay.

Assay of MVA

Assay plates (96 well) were seeded with BHK-21 cells (100 μl per well, $10^5$ cells/ml). Cells were diluted in DMEM supplemented with 10% FBS, and 1% PS. The plates were placed at +37° C., +5% $CO_2$ for 1-2 hours.

Meanwhile, a 10 fold dilution series of the formulated MVA samples was prepared in the same growth media ranging from 1 in 10 to 1 in 10,000. Each dilution series was prepared 5 times. 100 μl of each dilution was applied to individual wells containing BHK-21 cells (described above).

On 6 d p.i. the wells were scored for presence or absence of CPE and $TCID_{50}$ calculated. These were then used to estimate the concentration of infectious MVA per nil in the thermo-challenged vials.

Subsequently, a 2 fold dilution series of the formulated MVA samples was prepared ranging from 1 in 2,000 to 1 in 32,000. These dilutions were assayed separately but as before.

Results

The first pass of assaying these samples (LOG interval=1) yielded only five levels of response and one of these was below the detection threshold. More importantly, six of the eleven treatments were above the maximum detection threshold. These samples were re-assayed (LOG interval=0.3). The samples were held as liquid at +4° C. between the two assays. Some samples gave a meaningful value (between maximum and minimum thresholds) in both assays. This allowed determination of loss between the two assays.

After the second pass assay no treatments yielded a titre below the detection threshold. For ease of transformation this treatment was assigned a response equal to the minimum detection threshold.

Figure 45:
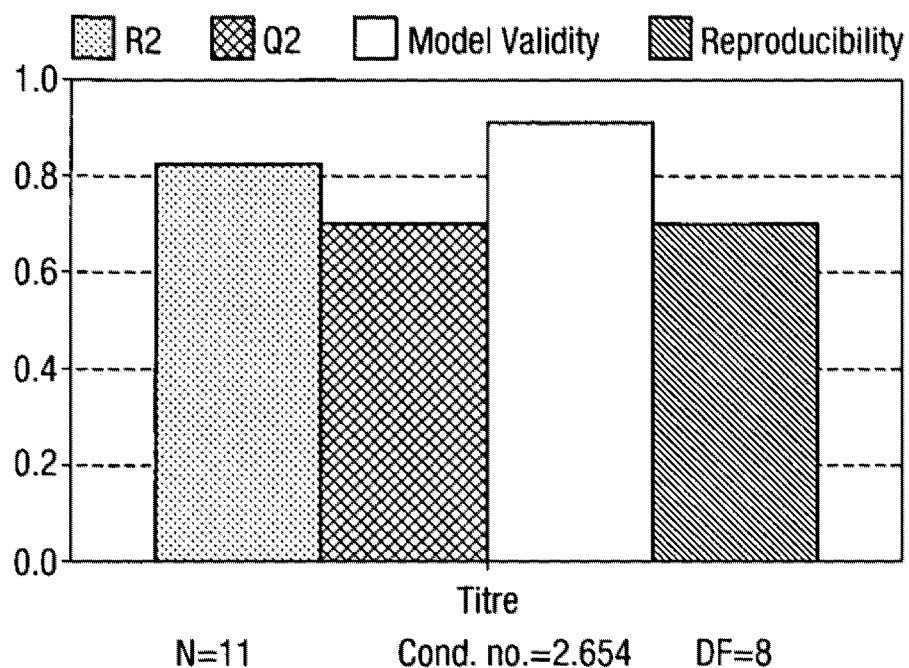
FIG. 45 summarises the statistics of the model in Example 16 used to represent the data.

The model generated from this data is relatively strong. Three of four parameters of model validity score over 0.9 (R2=0.82, Q2=0.70, Model Validity-0.91, Reproducibility=0.70) (see FIG. 45).

Figure 46:
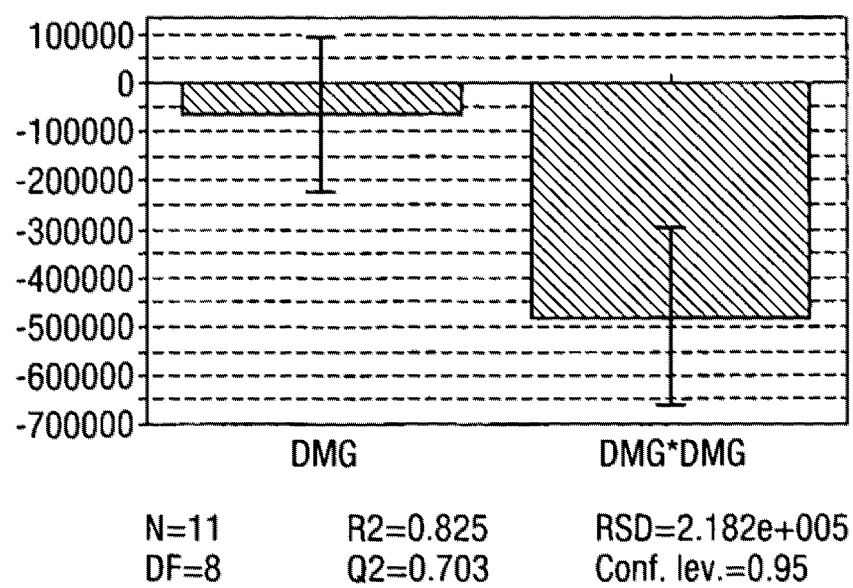
FIG. 46 shows terms retained in the model in Example 16 after fine tuning. Error bars not crossing the origin indicate a significant factor at the 95% C.I.

The model identified only one significant factor. DMG was found to have a second order (non-linear/quadratic) effect (see FIG. 46).

Figure 47:
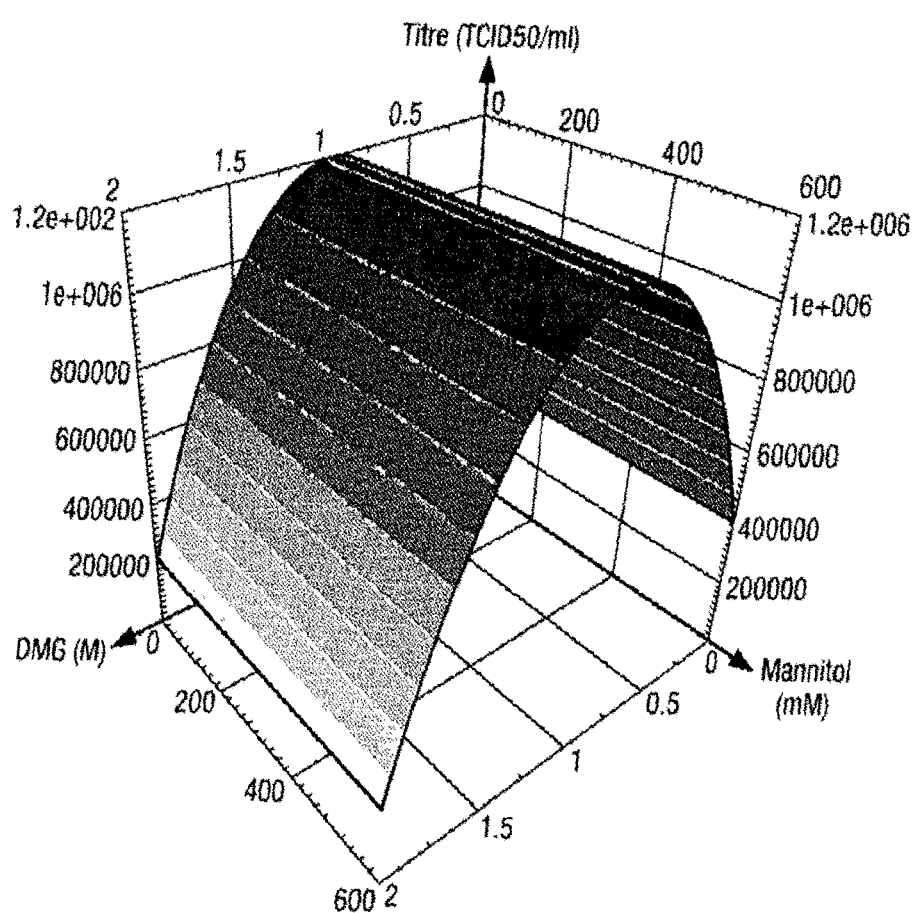
FIG. 47 shows a surface response plot of the predicted recovered viral titre in formulations of DMG and mannitol using the model of Example 16.
Figure 48:
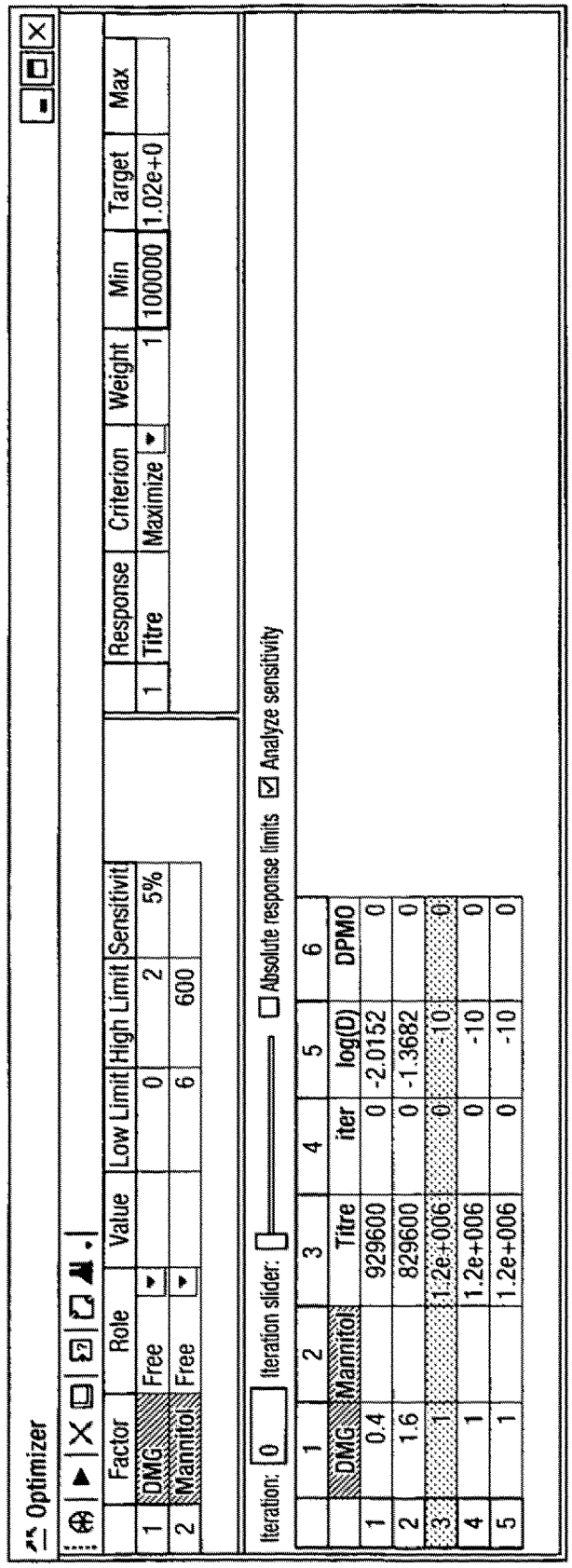
FIG. 48 shows a screen capture of the settings and outputs from the optimum predictions based on the model of the data in Example 16, generated using Monte-Carlo simulations. Iteration 48 highlighted in grey is the optimum formulation (1.0107M DMG).

FIG. 47 shows the RSM model generated. It is effectively a simple DMG dose response curve that is not altered by mannitol within the tested concentration range. The dose response curve identifies a clear optimum DMG concentration, as do monte-carlo simulations (see FIG. 48). The predicted optimum DMG concentration is 1.00M and predicted recovery of viral activity is 117% of starting titre.

The invention claimed is:

1. A method for preserving live viral particles during freeze-drying, the method comprising:
   (a) preparing an aqueous solution, which is optionally buffered, the solution comprising:
      (i) live viral particles selected from Adenoviridae, Orthomyxoviridae, Paramyxoviridae, Parvoviridae, Picornaviridae, Poxviridae, Calciviridae, Coronaviridae, Filoviridae, Flaviviridae, Hepadnaviridae, Herpesviridae, Papillomaviridae, Reoviridae, Retroviridae, and Toqaviridae, and
      (ii) as the sole excipients one or more sugars at a total sugar concentration of 0.1 M to 3M, 0.1 to 1.5M of N,N-dimethylglycine or a physiologically acceptable salt or ester thereof, and 0.1 to 1.5M of methylsulfonylmethane;
   and
   (b) freeze-drying the solution prepared in step (a) to form a composition incorporating said live viral particles.

2. The method according to claim 1 in which the sugar concentration of the aqueous solution is 0.2M to 2M.

3. The method according to claim 1 wherein aqueous solution comprises sucrose and one or more other sugar(s), and the ratio of the concentration of sucrose relative to the other sugar(s) is from 1:1 to 20:1 and/or the other sugar is raffinose.

4. The method according to claim 1 wherein one sugar is present which is mannitol.

5. A method of preparing a vaccine which incorporates live viral particles that are preserved during freeze-drying, which method comprises:
   (a) preparing an aqueous solution, which is optionally buffered, the solution comprising:
      (i) live viral particles selected from Adenoviridae, Orthomyxoviridae, Paramyxoviridae, Parvoviridae, Picornaviridae, Poxviridae, Calciviridae, Coronaviridae, Filoviridae, Flaviviridae, Hepadnaviridae, Herpesviridae, Papillomaviridae, Reoviridae, Retroviridae, and Togaviridae, and
      (ii) as the sole excipients one or more sugars at a total sugar concentration of 0.1 M to 3M, 0.1 to 1.5M of N,N-dimethylglycine or a physiologically acceptable salt or ester thereof, and 0.1 to 1.5M of methylsulfonylmethane;
   and
   (b) optionally adding an adjuvant, buffer, antibiotic and/or additive to the aqueous solution of (a); and
   (c) freeze-drying the solution prepared in step (a) or (b) to form a solid composition incorporating said live viral particles.

6. A method for preserving live viral particles during freeze-drying, the method comprising:
   (a) preparing an aqueous solution which consists of:
      (i) live viral particles selected from Adenoviridae, Orthornyxoviridae, Paramyxoviridae, Parvoviridae, Picornaviridae, Poxviridae, Calciviridae, Coronaviridae, Filoviridae, Flaviviridae, Hepadnaviridae, Herpesviridae, Papillomaviridae, Reoviridae, Retroviridae, and Togaviridae,
      (ii) one or more sugars at a total sugar concentration of 0.1M to 3M,
      (iii) 0.1 to 1.5M of N,N-dimethylglycine or a physiologically acceptable salt or ester thereof,
      (iv) 0.1 to 1.5M of methylsulfonylmethane;
      (iv) optionally one or more buffers;
   and
   (b) freeze-drying the solution prepared in step (a) to form a composition incorporating said live viral particles.

7. A method of preparing a vaccine which incorporates live viral particles that are preserved during freeze-drying, which method comprises:
(a) preparing an aqueous solution, which is optionally buffered, and consists of (i) live viral particles selected from Adenoviridae, Orthomyxoviridae, Paramyxoviridae, Parvoviridae, Picornaviridae, Poxviridae, Caliciviridae, Coronaviridae, Filoviridae, Flaviviridae, Hepadnaviridae, Herpesviridae, Papillornaviridae, Reoviridae, Retroviridae, and Toqaviridae, (ii) one or more sugars at a total sugar concentration of 0.1M to 3M, (iii) 0.1 to 1.5M of N,N-dimethylglycine or a physiologically acceptable salt or ester thereof, and (iv) 0.1 to 1.5M of methylsulfonylmethane; and
(b) optionally adding an adjuvant, buffer, antibiotic and/or additive to the aqueous solution of (a); and
(c) freeze-drying the solution prepared in step (a) or (b) to form a composition or solid composition incorporating said live viral particles.

8. The method according to claim 1 in which two sugars are present which are sucrose and raffinose.

9. The method according to claim 8 in which the ratio of the concentration of sucrose relative to raffinose is from 1:1 to 20:1.

10. The method according to claim 1 in which the viral particles are composed of a live virus which is a whole virus or live-attenuated virus.

11. The method according to claim 1 in which the aqueous solution comprises viral particles selected from Adenoviridae, Orthomyxoviridae, Paramyxoviridae, Parvoviridae, Picornoviridae and Poxviridae.

12. The method according to claim 11 in which the aqueous solution comprises viral particles selected from an adenovirus, vaccinia virus, influenza virus and measles virus.

13. The method according to claim 1 in which the aqueous solution comprises viral particles from Adenoviridae.

* * * * *